US010512739B2

(12) United States Patent
Allosery et al.

(10) Patent No.: US 10,512,739 B2
(45) Date of Patent: Dec. 24, 2019

(54) INHALATION DEVICE FOR USE IN AEROSOL THERAPY OF RESPIRATORY DISEASES

(71) Applicants: ABLYNX N.V., Ghent-Zwijnaarde (BE); VECTURA GMBH, Gauting (DE)

(72) Inventors: Koen Allosery, Ostend (BE); Martin Huber, Gauting (DE); Tobias Kolb, Gauting (DE); Bernhard Müllinger, Gauting (DE); Juliane Schick, Gauting (DE); Erik Depla, Destelbergen (BE)

(73) Assignees: VECTURA GMBH, Gauting (DE); ABLYNX N.V., Ghent-Zwijnaarde (BE)

( * ) Notice: Subject to any disclaimer, the term of this patent is extended or adjusted under 35 U.S.C. 154(b) by 299 days.

(21) Appl. No.: 15/517,579

(22) PCT Filed: Oct. 9, 2015

(86) PCT No.: PCT/EP2015/073486
§ 371 (c)(1),
(2) Date: Apr. 7, 2017

(87) PCT Pub. No.: WO2016/055655
PCT Pub. Date: Apr. 14, 2016

(65) Prior Publication Data
US 2017/0304565 A1    Oct. 26, 2017

Related U.S. Application Data

(60) Provisional application No. 62/074,842, filed on Nov. 4, 2014, provisional application No. 62/067,096, filed (Continued)

(30) Foreign Application Priority Data

Nov. 13, 2014    (EP) ..................................... 14193094

(51) Int. Cl.
*A61M 15/00*    (2006.01)
*A61M 15/02*    (2006.01)
(Continued)

(52) U.S. Cl.
CPC ......... *A61M 15/002* (2014.02); *A61K 9/0078* (2013.01); *A61K 39/395* (2013.01);
(Continued)

(58) Field of Classification Search
CPC .. A61M 11/00; A61M 11/005; A61M 11/042; A61M 15/00; A61M 15/002;
(Continued)

(56) References Cited

U.S. PATENT DOCUMENTS 4,430,995 A * 2/1984 Hilton ............... A61M 16/0057
128/204.21
6,598,602 B1 * 7/2003 Sjoholm .............. A61M 11/005
128/200.14
(Continued)

FOREIGN PATENT DOCUMENTS

EP    0368684    3/1994
EP    1908489    4/2008
(Continued)

OTHER PUBLICATIONS

DeVincenzo et al., "Evaluation of the safety, tolerability and pharmacokinetics of ALN-RSV01, a novel RNAi antiviral therapeutic directed against respiratory syncytial virus (RSV)," Antiviral Research, vol. 77, Issue 3, 2008, pp. 225-231, https://doi.org/10.1016/j.antiviral.2007.11.009 (Year: 2008).*
(Continued)

*Primary Examiner* — Joseph D. Boecker
(74) *Attorney, Agent, or Firm* — Matthew S. Gibson; Ryan P. Cox; Reed Smith LLP

(57) ABSTRACT

An inhalation device, assembly or system can include a kit and a pharmaceutical composition. The device can be adapted for administering therapeutic aerosols to pediatric patients, including neonates, infants or toddlers. The device can further include a vibrating mesh aerosol generator that
(Continued)

can be insertable into a flow channel of the inhalation device through a lateral opening, and a valved face mask. The device can be connectable to a gas source through which a gas, such as oxygen, can be received into the flow channel at a low flow rate.

22 Claims, 4 Drawing Sheets

Specification includes a Sequence Listing.

Related U.S. Application Data on Oct. 22, 2014, provisional application No. 62/062,469, filed on Oct. 10, 2014.

(51) Int. Cl.

| | | |
|---|---|---|
| *C07K 16/10* | (2006.01) | |
| *A61K 39/395* | (2006.01) | |
| *A61K 47/10* | (2017.01) | |
| *A61K 9/00* | (2006.01) | |
| *A61K 47/26* | (2006.01) | |
| *A61M 11/00* | (2006.01) | |
| *A61M 15/06* | (2006.01) | |
| *A61M 16/20* | (2006.01) | |
| *A61M 11/04* | (2006.01) | |
| *A61M 16/00* | (2006.01) | |
| *A61K 39/42* | (2006.01) | |
| *A61K 45/06* | (2006.01) | |
| *A61K 39/00* | (2006.01) | |

(52) U.S. Cl.
CPC .............. *A61K 39/42* (2013.01); *A61K 45/06* (2013.01); *A61K 47/10* (2013.01); *A61K 47/26* (2013.01); *A61M 11/005* (2013.01); *A61M 11/042* (2014.02); *A61M 15/00* (2013.01); *A61M 15/009* (2013.01); *A61M 15/0021* (2014.02); *A61M 15/0085* (2013.01); *A61M 15/0091* (2013.01); *A61M 15/025* (2014.02); *A61M 15/06* (2013.01); *A61M 16/0003* (2014.02); *A61M 16/204* (2014.02); *A61M 16/205* (2014.02); *A61M 16/208* (2013.01); *C07K 16/10* (2013.01); *C07K 16/1027* (2013.01); *A61K 2039/505* (2013.01); *A61K 2039/54* (2013.01); *A61K 2039/545* (2013.01); *A61M 2202/025* (2013.01); *A61M 2202/0208* (2013.01); *A61M 2202/0266* (2013.01); *A61M 2206/10* (2013.01); *A61M 2206/11* (2013.01); *A61M 2240/00* (2013.01); *C07K 2317/56* (2013.01); *C07K 2317/565* (2013.01); *C07K 2317/567* (2013.01); *C07K 2317/569* (2013.01); *C07K 2317/76* (2013.01); *C07K 2317/92* (2013.01)

(58) Field of Classification Search
CPC .......... A61M 15/0021; A61M 15/0085; A61M 15/0086; A61M 15/009; A61M 15/0091; A61M 15/025; A61M 15/06; A61M 16/00; A61M 16/0003; A61M 16/06; A61M 16/14; A61M 16/204; A61M 16/205; A61M 16/208; A61M 2202/0417; A61M 2202/0419; A61M 2206/11; A61M 2240/00; A61K 39/395; A61K 39/42; A61K 9/0078; C07K 16/10; C07K 16/1027

See application file for complete search history.

(56) References Cited

U.S. PATENT DOCUMENTS

| | | | |
|---|---|---|---|
| 9,956,360 B2* | 5/2018 | Germinario | A61M 15/00 128/202.15 |
| 2006/0191537 A1* | 8/2006 | Muellinger | A61M 15/00 128/205.24 |
| 2008/0000470 A1* | 1/2008 | Minocchieri | A61M 11/005 128/200.21 |
| 2008/0078383 A1* | 4/2008 | Richards | A61M 16/08 128/203.12 |
| 2009/0050137 A1* | 2/2009 | Wissink | A61M 11/06 128/200.14 |
| 2009/0223513 A1* | 9/2009 | Papania | A61M 15/0065 128/200.16 |
| 2009/0260628 A1* | 10/2009 | Flynn, Sr. | A61M 16/0078 128/203.28 |
| 2011/0146670 A1* | 6/2011 | Gallem | A61M 11/005 128/200.14 |
| 2012/0085344 A1* | 4/2012 | Luber | A61M 15/0085 128/200.16 |
| 2012/0167878 A1* | 7/2012 | Belson | A61F 7/12 128/200.16 |
| 2012/0318265 A1* | 12/2012 | Amirav | A61M 15/00 128/203.29 |
| 2013/0008436 A1 | 1/2013 | Von Hollen et al. | |
| 2013/0019860 A1 | 1/2013 | Depla et al. | |
| 2013/0104887 A1 | 5/2013 | Smutney et al. | |
| 2013/0118485 A1* | 5/2013 | Shahaf | A61M 15/00 128/202.15 |
| 2014/0020680 A1 | 1/2014 | Fink et al. | |
| 2017/0304566 A1* | 10/2017 | Allosery | A61K 39/395 |
| 2019/0127447 A1* | 5/2019 | Sargentini-Maier | C07K 16/1027 |

FOREIGN PATENT DOCUMENTS

| | | |
|---|---|---|
| EP | 2724741 | 4/2014 |
| JP | 2007531577 | 11/2007 |
| WO | 1994004678 | 3/1994 |
| WO | 1999042077 | 8/1999 |
| WO | 2004068820 | 8/2004 |
| WO | 2005018629 | 3/2005 |
| WO | 2005025540 | 3/2005 |
| WO | 2006003388 | 1/2006 |
| WO | 2006006963 | 1/2006 |
| WO | 2006030220 | 3/2006 |
| WO | 2006059108 | 6/2006 |
| WO | 2007049017 | 5/2007 |
| WO | 2007085815 | 8/2007 |
| WO | 2008101985 | 8/2008 |
| WO | 2008116165 | 9/2008 |
| WO | 2008142164 | 11/2008 |
| WO | 2010139808 | 12/2010 |
| WO | 2011098552 | 8/2011 |
| WO | 2013067164 | 5/2013 |
| WO | 2013098334 | 7/2013 |
| WO | 2013132056 | 9/2013 |
| WO | 2014159822 | 10/2014 |

OTHER PUBLICATIONS

Arzu Ari, "Performance Comparisons of Jet and Mesh Nebulizers with Mouthpiece, Aerosol Mask, and Valved Mask in Simulated Spontaneously Breathing Adults and Children." Journal of Aerosol Medicine and Pulmonary Drug Delivery, vol. 28, No. 0, 2014, pp. 1-9.

Aerogen Solo System Instruction Manual [www.aerogen.com] dated 2014.

Arzu Ari, "Performance Comparisons of Jet and Mesh Nebulizers with Mouthpiece, Aerosol Mask, and Valved Mask in Simulated Spontaneously Breathing Adults" Chest 2014.

Knoch, Martin and Keller, Manfred. "The customised electronic nebuliser: a new category of liquid aerosol drug delivery systems," Expert opinion on drug delivery, vol. 2(2), 2005, p. 377-390.

(56) References Cited

OTHER PUBLICATIONS

International Search Report and Written Opinion of PCT/EP15/73486 dated Dec. 10, 2015.
International Preliminary Report on Patentability of PCT/EP15/73486 dated Dec. 19, 2016.
Ward et al. 1989 (Nature 341:544-546).
Holt et al. 2003 (Trends Biotechnol. 21:484-490).
Muyldermans 2001 (Reviews in Molecular Biotechnology 74:277-302).
Davies and Riechmann 1994 (FEBS 339:285-290).
1995 (Biotechnol. 13:475-479).
1996 (Prot. Eng. 9:531-537).
Reichmann and Muyldermans 1999 (J. Immunol. Methods 231:25-38).
Janssens et al.; J Aerosol Med. 2001 Winter; 14(4):433-41.
Totapally et al.; Critical Care 2002, 6:160-165.
Nahata MC., et al., Management of bronchiolitis, Clin. Pharm. May-Jun. 1985; 4(3):297-303, abstract.
English translation of Search Report, Russian Application No. 2017115670, search completed May 12, 2019.
English translation of Official Action, Russian Application No. 2017115670, dated May 16, 2019.
Search Report, Russian Application No. 2017115845, search completed Apr. 12, 2019.
English translation of Official Action, Russian Application No. 2017115845, dated Apr. 12, 2019.
Notice of Reasons for Rejection, Japanese Patent Office, Application No. 2017-538457, dated Mar. 4, 2019, English Translation.
Depla, "Development of ALX-0171, an inhaled Nanobody for the treatment of respiratory syncytial virus infection in infants." Human Antibodies and Hybridomas Mar. 31-Apr. 2, 2014. Vienna, Austria.
Ottevaere, "Population PK of ALX-0171, an inhaled Respiratory Syncytial Virus (RSV) neutralizing Nanobody." Ablynx nv, Technologiepark 21, B-9052 Zwijnaarde, Belgium, Jun. 11, 2014.

* cited by examiner

INHALATION DEVICE FOR USE IN AEROSOL THERAPY OF RESPIRATORY DISEASES

CROSS-SECTION TO RELATED APPLICATIONS

This application is a United States national stage of International Application No. PCT/EP2015/073486, filed Oct. 9, 2015, which was published as International Publication No. WO 2016/055655, and which claims benefit of U.S. Provisional Patent Application No. 62/062,469, filed Oct. 10, 2014, U.S. Provisional Patent Application No. 62/067,096, filed Oct. 22, 2014, U.S. Provisional Patent Application No. 62/074,842, filed Nov. 4, 2014, and European Patent Application No. 14193094.1, filed Nov. 13, 2014, the entire contents of which are hereby expressly incorporated herein by reference in their entirety.

BACKGROUND

Diseases of the respiratory system such as asthma, bronchitis, cystic fibrosis, pulmonary infections with viruses or bacteria, and a number of other respiratory diseases may be treated with various therapeutic agents which are administered to the patient either systemically, i.e. by parenteral or oral administration, or by inhalation. While the concept of inhalation treatment is intriguing in that it involves the direct delivery of the active agent to the affected target site of the body, it is also challenging to achieve effective drug delivery to the lungs as this not only requires a particular aerosol quality to be generated and delivered to the patient, but often also the collaboration of the patient who may have to perform a particular breathing manoeuvre.

Various types of inhalation devices are available that are, in principle, capable of converting solid or liquid pharmaceutical formulations into inhalable aerosol, including dry powder inhalers, metered-dose inhalers and nebulisers. Nebulisers have in common that they convert a non-pressurised liquid formulation into respirable aerosolised droplets. Depending on the mechanism by which the aerosol droplets are generated, various different types of nebulisers may be distinguished, such as jet nebulisers, ultrasonic nebulisers, and vibrating-mesh nebulisers.

Some patient groups present a particular challenge for inhalation treatment. Such patients include those that have special anatomical or physiological characteristics that require particular aerosol parameters, for example small children; or patients that are not capable of performing specific manoeuvres, such as an inspiratory manoeuvre coordinated with manually triggering the release of a drug dose, as is required in the case of some metered-dose inhalers and powder inhalers. Patients with difficulties in this respect include those patients that are severely ill, that are under sedation, or suffer from a mental disability.

For some of these special patients, in particular children, it is therefore rather difficult to make an effective use of inhalation therapy, using the inhalation devices and the pharmaceutical drugs and formulations that are available today. Nevertheless, there is a pronounced need to allow such patients to benefit from inhalation therapy. For example, there are respiratory diseases which affect in particular young children such as neonates, infants and toddlers, while rarely occurring in adults or older children. An example is infection with respiratory syncytial virus (RSV), more specifically the human respiratory syncytial virus (hRSV). RSV is a recurrent cause of severe respiratory tract infections in infants and very young children. It causes annual epidemics, especially during the winter months. RSV infection may affect the upper respiratory system, which typically involves mild and transient symptoms, or constitute a severe lower respiratory tract infection (LRTIs) involving more serious symptoms such as bronchopneumonia and bronchiolitis.

With children, the challenges of effective therapeutic aerosol delivery increase with decreasing age of the child. Typically, neonates, infants and toddlers cannot yet generate the inspiratory flow required for using breath-triggered inhalation devices or powder-inhalers. At the same time, they are not able to use the mouthpiece of a nebuliser appropriately. In fact, infants up to the age of 18 months may not even be capable of any controlled oral inhalation manoeuvre.

Moreover, the airways of young children are several times smaller than those of adults, with narrow airways, high breath resistance and thus increased risk of impaction of aerosols in the upper airways. Also the tidal volume of young children is far lower than for adults and more variable, which further increases the challenges of paediatric inhalation therapy. Hence, there is a substantial need for improved therapies for paediatric patients affected with a respiratory disease. Similarly, there is a need for improved therapies for other patients with special limitations that are affected by respiratory diseases or conditions.

With respect to RSV therapy, the only approved drug product currently available in the market is Synagis®, a humanized monoclonal antibody administered by parenteral administration. With no other adequate treatment options at hand, the standard of care for infected infants is mainly supportive (e.g., fluid/feed supplementation, observation, and respiratory support as needed). Thus, there is clearly a need for an improved therapy for patients suffering from this disease, in particular paediatric patients.

WO 2010/139808 discloses immunoglobulin single variable domains directed against the fusion protein of the human respiratory syncytial virus as potential new therapies for RSV patients. For example, the document describes certain polypeptides including SEQ ID NOs: 65-85 along with some of their characteristics in vitro and in vivo. These polypeptides comprise 3 anti-hRSV immunoglobulin single variable domains that are recombinantly linked by a flexible linker. The effectiveness of the polypeptides was shown in rats. However, it is known that biological effects observed in rat studies cannot be easily extrapolated to humans, in particular not to specific human patient populations.

Moreover, formulations of these polypeptides in the form of nebuliser solutions have been described in WO 2011/098552. However, there remains a need for devices and methods to deliver such formulations effectively to patients in need thereof.

It is an object of the invention to improve the delivery of a therapeutic aerosol to a patient who cannot easily perform breathing manoeuvres required for conventional inhalation therapy, such as a paediatric patient.

It is a further object of the invention to improve the therapy of respiratory diseases, in particular respiratory infections such as RSV infections.

A further object is to overcome any of the disadvantages of the inhalation therapies of the art.

Further objects will become clear on the basis of the patent claims and the description.

SUMMARY OF THE INVENTION

Objects of the invention are met by an inhalation device according to claim 1, an assembly according to claim 8, a combination or kit comprising the inventive inhalation device, or the assembly, and a pharmaceutical composition for inhalation use according to claim 9, as well as a method of delivering a nebulised aerosol to a patient according to claim 13. The invention further provides the inhalation device, the assembly, and/or the combination or kit for use in the treatment of a patient suffering from a disease affecting the respiratory system according to claim 14. Advantageous embodiments are provided in the dependent claims.

In particular, an inhalation device is provided for delivering a nebulised aerosol to a patient, comprising (a) an aerosol generator with a vibratable mesh; (b) a reservoir for a liquid to be nebulised, said reservoir being in fluid connection with the vibratable mesh; (c) a gas inlet opening; (d) a face mask, having a casing, an aerosol inlet opening, a patient contacting surface, and a one-way exhalation valve or a two-way inhalation/exhalation valve in the casing having an exhalation resistance selected in the range from 0.5 to 5 mbar; (e) a flow channel extending from the gas inlet opening to the aerosol inlet opening of the face mask, the flow channel having a lateral opening through which the aerosol generator is at least partially inserted into the flow channel, and a constant flow resistance between the gas inlet opening and the aerosol inlet opening of the face mask at a flow rate of 1 to 20 L/min.

Upstream of the lateral opening, the flow channel may be shaped such as to effect a laminar flow when a gas is conducted through the flow channel at a flow rate of 1 to 20 L/min. Further, the flow channel may be sized and shaped to achieve, at a position immediately upstream of the lateral opening, a high velocity at a flow rate of 2 L/min.

In one embodiment, the flow channel exhibits no further inlet opening for receiving a gas. The gas inlet opening may be shaped as a tube fitting.

The aerosol generator of the inhalation device may be oriented such as to emit nebulised aerosol into the flow channel at an angle of approx. 90° to the longitudinal axis of the flow channel. In one embodiment of the invention, the inhalation device of the invention may comprise a switch for starting and stopping the operation of the aerosol generator and the operation of the aerosol generator may comprise the continuous vibration of the vibratable mesh.

The vibratable mesh of the inhalation device may comprise from 1,000 to 4,000 openings whose smallest diameter is predominantly in the range from 1.5 to 3.0 µm.

In one embodiment, the inhalation device may be connected to a gas source that provides a gas at a constant flow rate in the range from 1 to 5 L/min; said gas source being connected to the inhalation device such that the gas enters the flow channel through the gas inlet opening. Accordingly, an assembly comprising the inhalation device of the present invention and such a gas source is also considered to be falling under the scope of the invention. The gas provided by said gas source may be selected from oxygen, air, oxygen-enriched air, a mixture of oxygen and nitrogen, and a mixture of helium and oxygen. For the purpose of connecting the inhalation device to the gas source, the gas inlet opening may be shaped as a tube fitting as mentioned above.

In an optional embodiment—or as an alternative to a gas source providing gas at a constant flow rate in the range from 1 to 5 L/min—the inhalation device may comprise a flow restrictor capable of restricting the flow of gas through the flow channel to a constant flow rate in the range from 1 to 5 L/min when connecting the gas inlet opening with a pressurised gas source.

In a specific embodiment, the inhalation device may comprise: a) a base unit comprising an electronic controller for controlling the aerosol generator, and an upstream portion of the flow channel including the gas inlet opening; and b) a mixing channel unit, comprising a downstream portion of the flow channel including the lateral opening, wherein the downstream portion comprises a segment where the flow channel widens in the downstream direction, said segment being positioned downstream of the lateral opening.

In a further aspect of the invention, an assembly—or inhalation system—is provided comprising the inhalation device and a gas source providing a gas at a constant flow rate in the range from 1 to 5 L/min. The gas source is connected to the inhalation device such that the gas enters the flow channel through the gas inlet opening. The gas is preferably selected from oxygen, air, oxygen-enriched air, a mixture of oxygen and nitrogen, and a mixture of helium and oxygen. Optionally, the constant gas flow is in the range from about 1 to 3 L/min, such as about 2 L/min.

A further aspect of the invention is directed to a combination or kit comprising (a) the inhalation device or the assembly, and (b) a pharmaceutical composition for inhalation use. The pharmaceutical composition may comprise an active agent selected from antibiotics, antiviral agents, bronchodilators, anticholinergics, corticosteroids, hypertonic saline, antibodies, antibody fragments, and immunoglobulin single variable domains.

In a particular embodiment, pharmaceutical composition may comprise an anti-RSV agent, such as a polypeptide comprising or essentially consisting of one or more anti-RSV immunoglobulin single variable domains. The anti-RSV immunoglobulin single variable domain may comprise a CDR1 having the amino acid sequence of SEQ ID NO: 46, a CDR2 having the amino acid sequence of one of SEQ ID NOs: 49-50, and a CDR3 having the amino acid sequence of SEQ ID NO: 61. In particular, the anti-RSV immunoglobulin single variable domain may be selected from one of the amino acid sequences of SEQ ID NOs: 1-34. Suitable polypeptides which act as anti-RSV agents are the polypeptide selected from one of the amino acid sequences of SEQ ID NOs: 65-85.

Optionally, the combination or kit comprising a pharmaceutical composition for inhalation use incorporating an anti-RSV agent further comprise a bronchodilator, either within the same composition which also contains the anti-RSV agent or in a separate, additional pharmaceutical composition. The bronchodilator may belong to the class of beta2-mimetics; including long-acting beta2-mimetics, such as a bronchodilator selected from formoterol or a solvate thereof, salmeterol or a salt thereof, and mixtures thereof; or short-acting beta2-mimetics, such as a bronchodilator selected from salbutamol, terbutaline, pirbuterol, fenoterol, tulobuterol, levosabutamol and mixtures thereof. In a specific embodiment, the bronchodilator is salbutamol and may be administered at a dose of 200 micrograms. Alternatively, the bronchodilator may belong to the class of anticholinergics, such as a bronchodilator selected from tiotropium, oxitropium, ipratropium bromide and mixtures thereof.

In a yet further aspect of the invention, a method of delivering a nebulised aerosol to a patient is provided, comprising the steps of (a) providing the inhalation device, or the combination or kit, according to this invention; (b) providing a gas source; and (c) connecting the gas source to the inhalation device such that the gas enters the flow channel through the gas inlet opening at a constant flow rate in the range from 1 to 5 L/min.

The invention further provides the use of the inhalation device, or of the assembly, or of the kit or combination, for inhalation treatment of a patient in need thereof. The patient may be a paediatric patient such as a neonate, an infant, a toddler, or a school child. Alternatively, the patient is an adult patient for whom controlled oral inhalation is not possible or considerably impeded, such as a patient with dementia, other mental impairment, COPD, severe asthma, cystic fibrosis, amyotrophic lateral sclerosis, emphysema, or heart failure, or a patient under sedation or anaesthesia.

Optionally, the patient is suffering from a disease affecting the respiratory system. For example, the patient may suffer from a respiratory infection. In a particular embodiment, the patient is infected with RSV, such as with RSV lower respiratory tract infection, and the use involves the delivery of an anti-RSV agent to the patient via the inhalation route.

Further advantageous embodiments, features, beneficial effects and uses of the device are described below in more detail.

DEFINITIONS

The following expressions as used herein should normally be interpreted as outlined in this section, unless the description provides a different meaning in a specific context.

An "aerosol" is a dispersion of small, typically inhalable solid particles or liquid droplets in a continuous gas phase such as air. Herein, the term "aerosol" may refer either to the nascent aerosol as it is emitted from an aerosol generator within an inhalation device; or to aerosol resulting from the dispersion of such nascent aerosol in an inhalable gas, as it is emitted from the inhalation device and made available for inhalation. The exact meaning is derivable from the context.

An "aerosol generator" is a device or device component capable of generating an aerosol from a liquid formulation; e.g. a pharmaceutical composition for inhalation use. Synonymously, the terms "nebuliser" or "nebulising means" may be employed.

Unless specified otherwise, a "gas" refers to any gas or mixture of gases suitable for inhalation.

Unless specified otherwise, "young children" refers to children of 6 years age or younger. "Neonates" means children up to 1 month of age, "infants" means an age from 1 to 12 months, and "toddlers" means an age from 1 to 3 years. For practical reasons, though, the attribution to these groups should be based on the physiological and cognitive development stage of the child rather than solely its age.

"Lateral", or "laterally", means away from the middle, centre, or centre axis of a device or device component.

All terms designating a position, orientation or direction, such as left, right, front, rear, back, top, bottom, up, down and the like, should be understood with reference to the orientation of the inhalation device or its components under normal operational conditions, and typically from the perspective of the user. For the avoidance of any misunderstandings, it is clear that a user may also hold the device in such a way that there is some deviation from a normal operational orientation. For example, while the device is designed to be held in an approximately horizontal orientation with respect to the axis along which the air flow within the device occurs, the user may also hold the device at an angle of up to 45° deviating from the horizontal orientation, without negative impact on the device function. Similarly, a user may, to some degree, rotate the device around said axis, again without any substantial deterioration of device performance.

"Comprise" or "comprising" with reference to any feature means that the respective feature must be present, but without excluding the presence of other features.

"A" or "an" does not exclude a plurality.

"Essentially", "about", "approximately" and the like in connection with an attribute or value include the exact attribute or the precise value, as well as any attribute or value typically considered to fall within a normal range or variability accepted in the technical field concerned.

A polypeptide (such as an immunoglobulin, an antibody, an immunoglobulin single variable domain, or generally an antigen binding molecule or a fragment thereof) that can "bind to" or "specifically bind to", that "has affinity for" and/or that "has specificity for" a certain epitope, antigen or protein (or for at least one part, fragment or epitope thereof) is understood to be "against" or "directed against" said epitope, antigen or protein or is a "binding" molecule with respect to such epitope, antigen or protein, or is said to be "anti"-epitope, "anti"-antigen or "anti"-protein (e.g., "anti"-hRSV).

Any reference signs in the claims should not be construed as a limitation to the embodiments represented in any of the drawings.

A single unit may fulfil the functions of several features recited in the claims.

LIST OF NUMERICAL REFERENCES USED IN THE FIGURES

Figure 1:
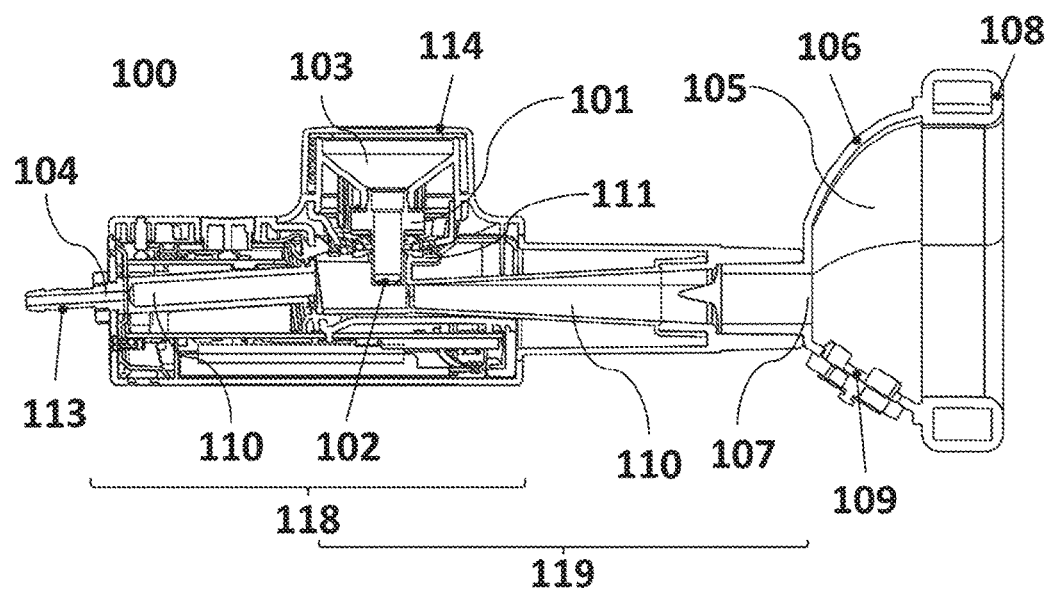
FIG. 1 shows a cross-sectional side view of a specific embodiment of the inhalation device according to the invention

100 Inhalation device
101 Aerosol generator
102 Vibratable Mesh
103 Reservoir
104 Gas inlet opening
105 Face mask
106 Casing
107 Aerosol inlet opening
108 Patient contacting surface
109 Valve (one-way exhalation or two-way inhalation/exhalation valve)
110 Flow channel
111 Lateral opening
112 Switch
113 Tube fitting
114 Lid
115 Key lock
116 USB-Port
117 Holes
118 Base unit
119 Mixing channel unit
200 SAINT model
201 Face/throat portion of the SAINT model
202 Nasal portion of the SAINT model
300 Glass fibre filter assembly

DETAILED DESCRIPTION OF THE INVENTION

In a first aspect of the invention, an inhalation device is provided for delivering a nebulised aerosol to a patient, comprising (a) an aerosol generator with a vibratable mesh; (b) a reservoir for a liquid to be nebulised, said reservoir being in fluid connection with the vibratable mesh; (c) a gas inlet opening; (d) a face mask, having a casing, an aerosol inlet opening, a patient contacting surface, and a one-way exhalation valve or a two-way inhalation/exhalation valve in the casing having an exhalation resistance selected in the range from 0.5 to 5 mbar; and (e) a flow channel extending from the gas inlet opening to the aerosol inlet opening of the face mask, the flow channel having a lateral opening through which the aerosol generator is at least partially inserted into the flow channel, and a constant flow resistance between the gas inlet opening and the aerosol inlet opening of the face mask at a flow rate of 1 to 20 L/min.

A cross-sectional side view of one exemplary embodiment of such an inhalation device can be seen in FIG. 1. FIG. 1 depicts an inhalation device (100); an aerosol generator (101) with a vibratable mesh (102); a reservoir (103) in fluid connection with the vibratable mesh (102); a gas inlet opening (104); a face mask (105) with a casing (106), an aerosol inlet opening (107), a patient contacting surface (108), and a one-way exhalation valve or a two-way inhalation/exhalation valve (109); and a flow channel (110) leading from the gas inlet opening (104) to the aerosol inlet opening (107) of the face mask (105). The flow channel (110) has a lateral opening (111) through which the aerosol generator (101) is partially inserted with its downstream end. In the depicted embodiment, the reservoir is covered by a screw-on lid (114) and the gas inlet opening (104) is shaped as, or equipped with, a tube fitting (113).

Figure 2:
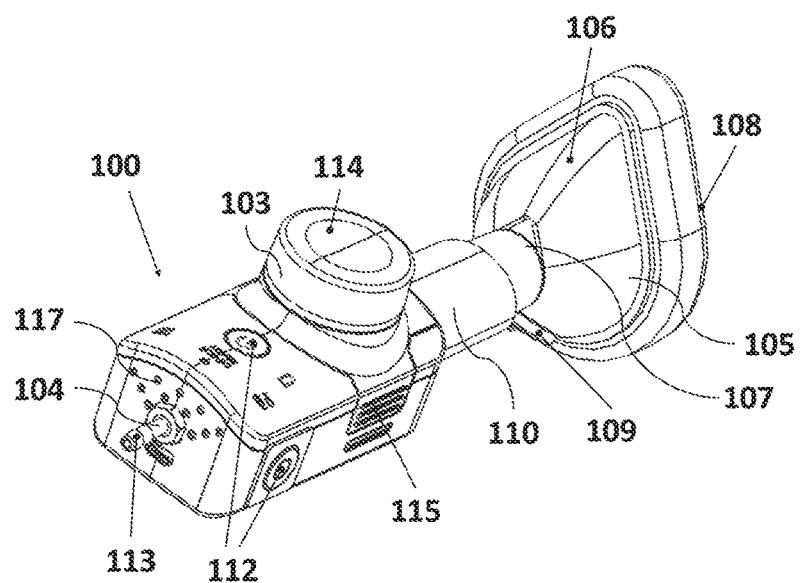
FIG. 2 shows a perspective view of a specific embodiment of the inhalation device according to the invention.
Figure 3:
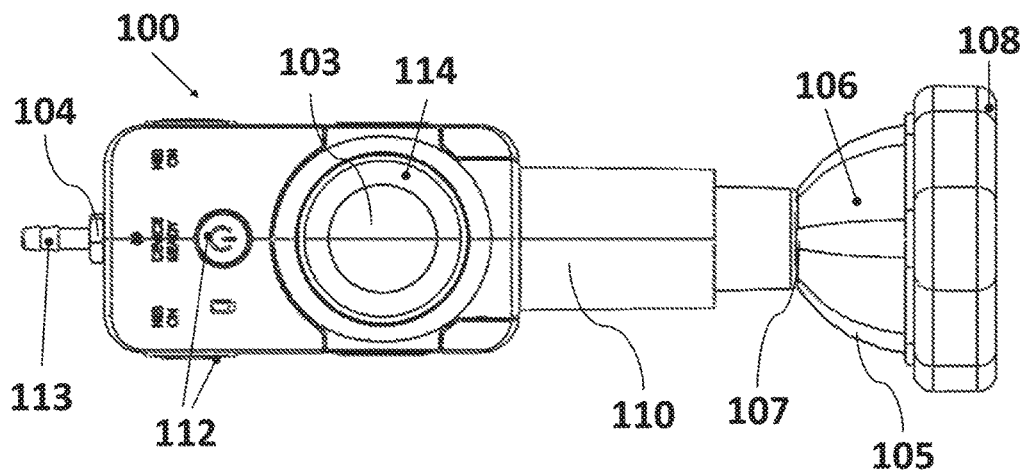
FIG. 3 shows a top view of a specific embodiment of the inhalation device according to the invention.
Figure 4:
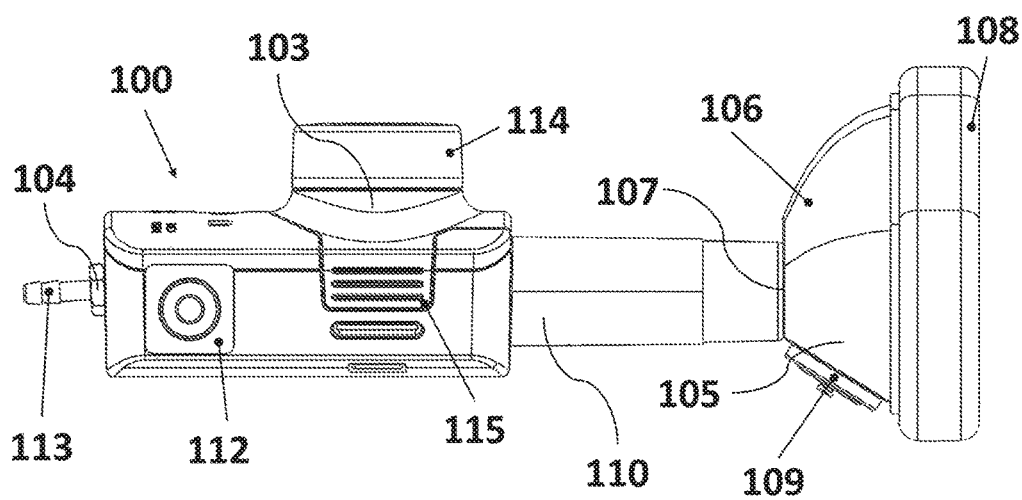
FIG. 4 shows a side view of a specific embodiment of the inhalation device according to the invention.
Figure 5:
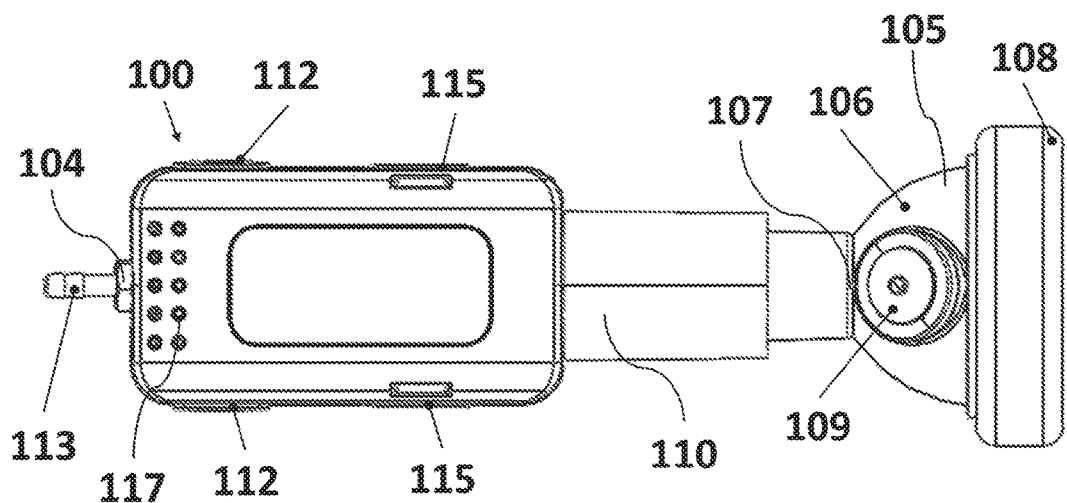
FIG. 5 shows a bottom view of a specific embodiment of the inhalation device according to the invention.
Figure 6:
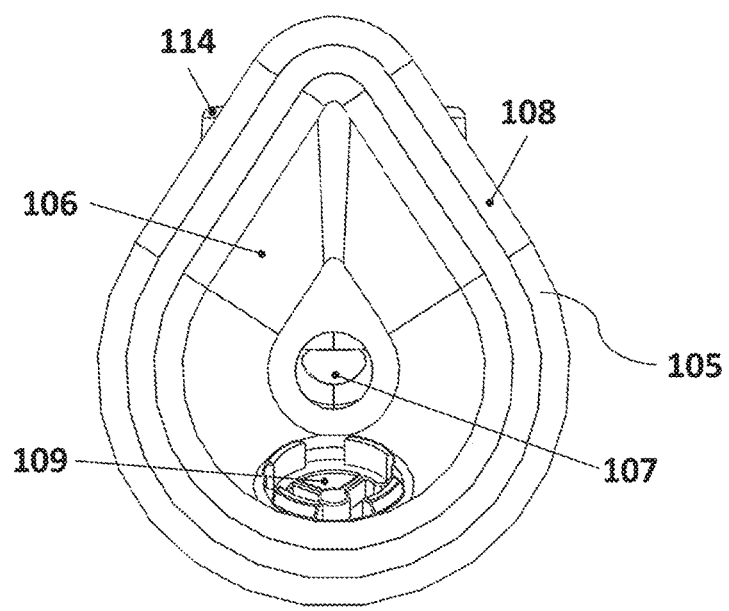
FIG. 6 shows a front view of a specific embodiment of the inhalation device according to the invention.

The exemplary inhalation device of FIG. 1 is further depicted in a perspective side view in FIG. 2 and in top, side and bottom views in FIGS. 3 to 5, respectively. The front and rear views of this exemplary inhalation device are provided in FIGS. 6 and 7, respectively. The referenced features will be dealt with in depth below. If a reference sign is used in the context of the general description of a feature below, this should be understood as an illustrative reference to an exemplary embodiment of the feature, and not as a limitation of the invention to that embodiment.

The inventors have unexpectedly found that the inventive inhalation device with a face mask and a flow channel having a constant flow resistance in combination with a vibrating mesh aerosol generator as defined in claim 1 is particularly effective for delivering a therapeutic aerosol to certain types of patients, such as patients having a low tidal volume, paediatric patients, elderly patients, patients that profit from inhaling oxygen in addition to air, and/or patients affected with certain respiratory diseases, such a infections of the respiratory tract, e.g. RSV infection. In particular, it allows the delivery of the therapeutic aerosol in a manner that is largely independent of the inspiratory capability of the patient. Moreover, it enables the effective use of a gas (such as oxygen, or oxygen-enriched air) supplied from an external source at a very low flow rate (such as 1 to 5 L/min) which may be used as sole carrier gas to receive and disperse the nascent aerosol in the inhalation device and provide it to the patient for inhalation.

As used herein, the inhalation device is a device capable of generating and delivering a therapeutic aerosol which is inhalable by a patient. An inhalable aerosol is different from e.g. a nasal or oral spray in that the particle or droplet size of the inhalable aerosol is substantially smaller, i.e. predominantly smaller than about 10 µm, and suitable for entering the lungs.

The device according to the invention comprises an aerosol generator (101) with a vibrating mesh (102). It has been found that vibrating mesh nebulisers are particularly advantageous in the context of the invention. They have a high output rate which helps to keep the time required to administer a dose short. This is particularly helpful if the patient is a paediatric patient, as paediatric patients are even less tolerant to long inhalation times. Moreover, vibrating mesh nebulisers are capable of generating a dense aerosol without requiring a high gas flow rate for aerosol generation, as e.g. jet nebulisers do. In addition, vibrating mesh inhalers are more silent than other types of aerosol generators and thus found less disturbing by paediatric patients. They may even be used while the child sleeps, which could ensure a deep and calm breathing pattern.

Optionally, the vibratable mesh (102) of the inhalation device comprises from 1,000 to 4,000 openings whose smallest diameter is predominantly in the range from 1.5 to 3.0 µm. This provides a particularly fine aerosol mist. Preferably, the vibratable mesh is selected such as to generate an aerosol with a volume median droplet size as measured by laser diffraction ranging from 2 to 5 µm, or from 2 to 4 µm, or from 2 to 3 µm. Such fine aerosols are particularly advantageous for neonates, infants and toddlers.

The inhalation device further comprises a reservoir (103) for a liquid to be nebulised; the reservoir is in fluid connection with the vibratable mesh (102). The reservoir may have a volume of 0.1 to 10 mL, or from 0.5 to 5 mL, to accommodate the liquid, which is typically a pharmaceutical composition comprising an active ingredient. Preferably, the reservoir (103) is located at a superior position relative to the body of the aerosol generator (101). It may be closable by a screw-on or snap-on lid; see e.g. the screw-on lid (114) depicted in FIG. 1. This is particularly useful if the aerosol generator has a roughly vertical orientation during use, with the vibratable mesh being positioned at its lower end and having a roughly horizontal orientation. Such arrangement would be useful as it reduces the spilling risk and ensures that the vibratable mesh remains covered with liquid during aerosol generation, which enables a more uniform aerosol output rate.

Optionally, the aerosol generator (101) and/or the reservoir (103) may be provided in a detachable manner with regard to the flow channel of the inhalation device. For instance, there may be a housing component for both the aerosol generator (101) and the reservoir (103) which may be detachable from the flow channel component of the inhalation device. This offers the advantage that the components can be cleaned more easily and/or that different aerosol generators may be coupled to, and operated with the same flow channel.

The device further comprises a gas inlet opening (104). The gas inlet opening is preferably connectable to an external gas source, either directly or indirectly via a tube or other conduit. The gas inlet opening (104) may be shaped as, or equipped with, a tube fitting (113) in order to facilitate the attachment of a gas source, as can be seen e.g. in FIGS. 1 and 2. The fitting may be a standard fitting with respect to its shape and dimensions, and preferably made from an inert material such as stainless steel. It is also advantageous to use a tube fitting whose inner wall is smooth and shaped as a regular cylinder, such as to allow a laminar flow of gas. The gas inlet opening (104) may be accommodated in a rear position of the inhalation device (100), as shown in FIGS. 1 to 5 and FIG. 7 for the exemplary embodiment.

In a preferred embodiment, the gas inlet opening (104) is the only inlet opening for allowing a gas to flow into the flow channel (110), with the exception of the aerosol generator, or the reservoir connected with the aerosol generator, through which very small amounts of gas (typically air) may enter the device to replace the nebulised liquid. In this embodiment, the gas phase of the therapeutic aerosol delivered to the patient by the device is predominantly the gas which is supplied to the gas inlet opening, and which may be selected according to the needs of the patient.

Figure 7:
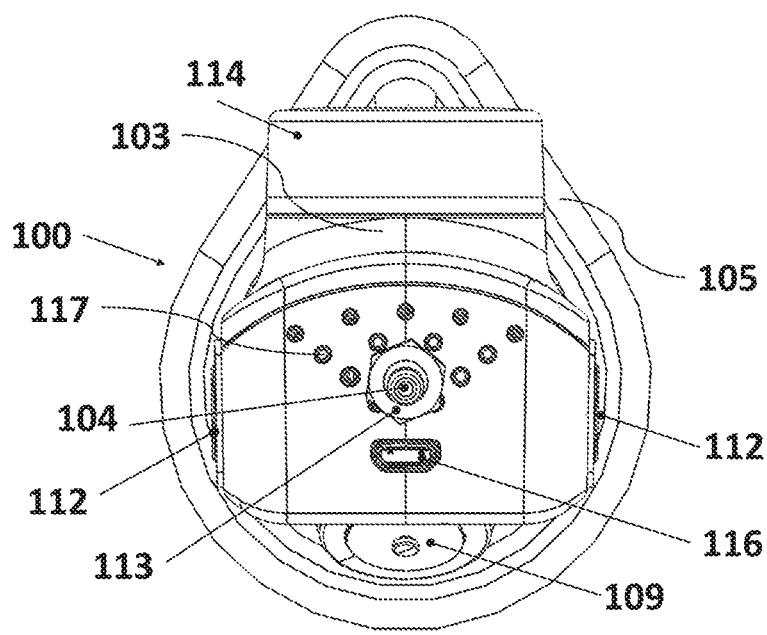
FIG. 7 shows a rear view of a specific embodiment of the inhalation device according to the invention.

It is noted that the small openings (117) seen in FIGS. 2, 5 and 7 are not in fluid connection with the flow channel. They may optionally be provided in the casing of the device in order to allow for air-cooling of any electronic components.

An important feature of the device is the face mask (105). It has a casing (106), an aerosol inlet opening (107), a patient contacting surface (108), and a one-way exhalation valve or a two-way inhalation/exhalation valve (109) in the casing. The valve has an exhalation resistance selected in the range from 0.5 to 5 mbar.

Such face mask receives the aerosol generated in the device via a flow channel and allows the aerosol to be stored until it is inhaled by the patient. It also serves as a means to enable nasal inhalation. Thus the patient may inhale the aerosol either through the mouth or the nose. This is advantageous in that patients that are not capable of performing oral inhalation manoeuvers, such as small children or sleeping patients, may still receive inhalation therapy. It is particularly advantageous for paediatric patients who have a highly variable breathing frequency and a small and variable tidal volume.

Optionally, the face mask may also be provided separately from the inhalation device, or in a kit which comprises the inhalation device as described herein and a matching face mask, the inhalation device being connectable to the face mask and, vice versa, the face mask having an aerosol inlet opening which is adapted to engage with the inhalation device.

The face mask is configured to allow the exhalation by the patient through the mask. This is achieved by the valve which exhibits a rather small exhalation resistance. The valve, or the exhalation resistance of the valve, may be selected within the range specified above and in view of the patient. For a small child, a rather low exhalation resistance of less than about 3 mbar, or in the range from about 0.5 mbar to about 2 mbar, is presently preferred. Such resistance is low enough to enable easy exhalation without much interference with normal breathing; on the other hand, the resistance is sufficient to achieve a slight overpressure in the face mask as it continuously receives the aerosol generated in the device when the aerosol generator operates. Such slight overpressure has been found to assist the patient to inhale the therapeutic aerosol more effectively, and may contribute to a more effective drug deposition in the deeper airways of the respiratory system.

As mentioned, the face mask is particularly suitable for patients that have difficulty using a mouthpiece to inhale an aerosol. This is often the case with paediatric patients, such as neonates, infants, toddlers, or young school children. However, the face mask is also advantageous for adult patients suffering e.g. from dementia, mental impairment, COPD, heart failure, severe asthma attacks, cystic fibrosis, amyotrophic lateral sclerosis, emphysema or patients under sedation or anaesthesia. The face mask may be held in place, or positioned, by a caregiver.

The face mask may be connectable to, or form an integral part of, the flow channel, forming its down-stream end. A connectable face mask potentially offers the advantage of easy cleaning and/or replacement. The invention is also directed to a combination of an inhalation device and a face mask which together exhibit the features of claim 1, as well as to an inhalation device adapted for being connected with a separate face mask where the inhalation device and the face mask together exhibit the same features. On the other hand, if the face mask forms an integral part of the flow channel, the number of components is reduced and mismatches of flow channels and face masks of different patients, e.g. after cleaning, are avoided, which may be advantageous in hospital settings.

The face mask may further be provided in a movable manner, e.g. comprising a pivoting joint near the aerosol inlet opening. Such joint may enable a deflection of the downstream portion of the flow channel as part of the mask to allow the caregiver to hold the main body of the inhalation device at a different angle from that of the face mask.

Without the pivoting joint, the face mask is also suitable, in particular if the device dimensions are rather small. It has been found that caregivers tend to hold the inhalation device at or near the face mask, which is closer to the patient's face, rather than holding the main body of the device.

Preferably, the mask is made from a transparent, break-resistant material, such as polypropylene or the like, to enable the parent or caregiver to see the aerosol mist and the patient's face and breathing activity.

The patient contacting surface may be made from a soft, mouldable, antiallergenic and well-tolerated material which is preferably free of additives or contaminants like phthalates, bisphenol A or latex. The patient contacting surface may include a soft silicone lip or an inflatable cushion to increase patient comfort.

Preferably, the nominal internal volume of the face mask is not more than about 120 mL. As used herein, the nominal internal volume is understood as the internal volume enclosed by the casing from the aerosol inlet opening to the patient contacting surface when the patient contacting surface is placed on a flat surface. This volume is slightly larger than the effective internal volume, or so-called dead space, which is the volume enclosed by the mask when placed against the face of a patient, and which therefore depends on the size and shape of the patient's face. If the patient is a school child, the nominal internal volume is preferably not more than about 90 mL, or even not more than about 80 mL, or not more than about 70 mL, or not more than about 60 mL, or not more than about 50 mL, or not more than about 40 mL, respectively, depending on the size of the face of the patient. It is currently preferred to select a mask with a nominal internal volume of not more than about 40 or 50 mL if the patient is a neonate.

It is further preferred to select the nominal internal volume of the face mask with respect to the patient's average tidal volume. Advantageously, the nominal internal mask volume is smaller than the tidal volume. For example, if the patient is a paediatric patient having an average tidal volume during normal breathing of about 80 mL, the nominal internal face mask volume should be smaller than this. In particular, the respective volume may be in the range from about 10% to about 80% of the average tidal volume. In further embodiments, the nominal internal face mask volume is not more than about 60%, or even not more than about 50%, of the patient's average tidal volume.

In one embodiment, the face mask has a two-way inhalation- and exhalation valve having a resistance of not more than 3 mbar in either direction, and wherein the nominal internal volume of the face mask is not more than about 50 mL. This embodiment is particularly suitable for small paediatric patients such as neonates, infants, and toddlers. In another embodiment, the face mask has one or more inhalation valves and one or more exhalation valves, wherein the exhalation valve has a resistance of not more than 3 mbar, and wherein the nominal internal volume of the mask is not more than about 70 mL. This embodiment is particularly suitable for toddlers and children.

The inventors have found that such minimised face mask volumes contribute to an increased uptake of the nebulised aerosol by the patients, and to a better deposition of the aerosolised active compound in the respiratory system of the patients.

As mentioned above, the face mask comprises in its casing at least one valve which may be a one-way exhalation valve or a two-way inhalation- and exhalation valve, and wherein the exhalation resistance of the valve is in the range from about 0.5 to 5 mbar. The effect of this feature is that it allows the generation of a mild overpressure in the face mask, in particular when the gas inlet opening of the device is connected to a gas source from which gas is received into the device at a flow rate of 1 to 5 L/min. The slight overpressure facilitates the patient's inhalation of the nebulised aerosol generated in the device, without interfering substantially with the normal breathing pattern, thus enabling effective drug delivery.

Optionally, the face mask may comprise further inhalation and/or exhalation valves. If so, the effective exhalation pressure of the combined valves should still be in the specified range, i.e. between about 0.5 and 5 mbar. Optionally, the exhalation pressure may also be selected from about 0.5 mbar to about 3 mbar, such as about 1 mbar or about 2 mbar, respectively. The valve(s) provided in the face mask may have any structure suitable for providing this exhalation resistance; e.g. slit valves, duck bill valves or membrane valves, to mention only a few. For example, the valve may be a one-way valve with a cross-slit and an overlying membrane, such as a silicone membrane. In one direction, from the cross-slit to the membrane, the valve opens, whereas in the opposite direction the membrane will be pressed tightly onto the cross and thus blocks the valve. Depending on which way round the valve is inserted into the face mask, it can serve both as an inhalation or an exhalation valve.

An important feature of the inhalation device of the invention is the flow channel (110), which extends from the gas inlet opening (104) to the aerosol inlet opening (107) of the face mask (105). The flow channel has a lateral opening (111), as exemplified by the device depicted in FIG. 1, through which the aerosol generator is at least partially inserted into the flow channel. Moreover, the flow channel exhibits a constant flow resistance between the gas inlet opening and the aerosol inlet opening of the face mask at a flow rate of 1 to 20 L/min.

The flow channel is configured to receive a gas from an external gas source through the gas inlet opening which forms the upstream end of the flow channel. The upstream portion of the flow channel, i.e. the segment from (and including) the gas inlet opening (104) to the lateral opening (111) through which the aerosol generator (101) is at least partially inserted, is preferably sized and shaped such as to achieve a laminar flow of a gas which in conducted through the flow channel at a constant flow rate selected in the range from 1 to 20 L/min, and in particular at a constant flow rate in the range from about 1 L/min to about 5 L/min.

It is generally known which type of shapes should be used (or avoided) in order to enable a laminar flow of gas in a flow channel. For example, abrupt diameter changes should be avoided, and a smooth inner wall is preferred to an inner wall made from a material having a rough surface. An example of a suitable upstream segment is a regular cylindrical pipe made of polished stainless steel or of an inert polymeric material having a smooth surface.

Also, the gas inlet opening, which may be shaped as a tube fitting in order to facilitate the attachment of a gas source as mentioned above, may preferably be made from an inert, smooth material such as stainless steel, such as to allow a substantially laminar flow of gas. It is further advantageous to use a tube fitting whose inner wall is smooth and shaped as a regular cylinder, such as to further promote substantially laminar flow of gas. A substantially laminar flow means a Reynold's number of not more than about 2300. Preferably, the upstream segment of the flow channel is sized and shaped to achieve a Reynold's number of not more than 2000 at the flow rates specified above.

According to the invention, the flow channel also has a constant flow resistance between the gas inlet opening and the aerosol inlet opening of the face mask. In this respect, it differs substantially from the inhalation device of e.g. EP2724741 which comprises a variable flow restrictor to restrict the inspiratory flow rate of a patient—in particular an adult patient—to a desired low flow rate such as about 15 L/min, regardless of the underpressure created by the patient at the mouthpiece.

The lateral opening (111) which receives the aerosol generator (101) is preferably located at an upper position of the flow channel (110) with respect to the normal orientation of the device in use, as is depicted e.g. in FIGS. 1 and 2. The opening is preferably sized to match the dimensions of the aerosol generator so that the opening is completely and tightly closed when the aerosol generator is received. Preferably, the aerosol generator is in a partially inserted position during use, and the downstream end of the aerosol generator protrudes towards (or even to) the longitudinal centre axis of the flow channel.

In the optional case where the aerosol generator is provided in a component detachable from the flow channel component of the inhalation device (100), fixing means may be provided, such as a key lock (115), in order to secure, or fix, the at least partially inserted aerosol generator in its intended position in the flow channel; as can be seen in FIG. 2 or 4, for instance.

In one embodiment, the aerosol generator is oriented such as to emit nebulised aerosol into the flow channel at an angle of approximately 90° to the longitudinal axis of the flow channel. In this case, the aerosol generator is arranged in an approximately vertical orientation and the vibrating mesh is approximately horizontal.

While such arrangement offers several advantages such as facilitating the manual filling of the reservoir and a continuous supply of liquid to the vibratable mesh, it requires that the plume of nascent aerosol is deflected by about 90° without any significant degree of coalescence or aerosol deposition. This is a particular challenge if the aerosol generator is efficient and exhibits a high rate of aerosol generation, which is desirable with an eye on the inhalation time required for the administration of a drug dose.

Optionally, the aerosol generator is selected and operated such as to have an aerosol generation rate (or nebulisation rate) of at least about 0.1 mL/min, or of at least 0.2 mL/min. In some embodiments, the aerosol generator has a nebulisation rate of at least 0.3 mL/min, 0.4 mL/min, 0.5 mL/min, 0.6 mL/min, or even at least 0.7 mL/min.

Unexpectedly, the inventors have found that the inhalation device with a vibratable mesh aerosol generator and a flow channel as defined herein is indeed capable of dispersing the nascent aerosol, even at a low gas flow rate of 1 to 5 L/min, such as at a constant flow rate of about 2 L/min, and of conducting the aerosol into the face mask without any significant deposition in the flow channel. It is believed that such effect is shown for the first time for a therapeutic inhalation device.

The effect is particularly pronounced if the flow channel is sized and shaped to achieve, at a position immediately upstream of the lateral opening, a relatively high gas velocity at a given gas flow rate. In particular, it is preferred that the average gas velocity at a flow rate of 2 L/min is at least about 4 m/s. Optionally, it is at least about 5.5 m/s, or at least about 8 m/s, respectively. As used herein, the average gas velocity in the flow channel at a specific position is defined as the mean velocity value obtained by Computational Fluid Dynamics analysis (CFD) for this position, such as immediately upstream of the lateral opening.

It was also unexpected to find that it does not require a large mixing chamber to disperse the nascent aerosol in the flowing gas without significant droplet deposition in the device. In particular if the preferred laminar flow and the preferred velocities as described above are used, the actual dimensions of the flow channel can be rather small. In fact, the relatively small dimensions enable rather high gas velocities, and the inventors have found that these are at least as useful to avoid aerosol loss through deposition in the device as large mixing chambers as used in some other devices. Preferably, the flow channel's dimensions are such that the total interior volume of the channel between the lateral opening and the aerosol inlet opening of the face mask is not more than about 30 mL. Optionally, it is not more than about 25 mL, or not more than about 20 mL, respectively. In some cases, the interior volume of the flow channel may be less than about 18 mL, or even less than about 15 mL.

In a specific embodiment, the flow channel has an internal diameter at a position immediately upstream of the lateral opening of about 10 mm to about 13 mm; optionally in combination with a vibratable mesh that has a total diameter of about 6 mm to about 8 mm. It is noted that the diameter of the region of the mesh having the openings, or apertures, may be smaller than the total diameter, e.g. by about 1 to 3 mm.

In a specific embodiment, the ratio of the internal diameter of the flow channel immediately upstream of the lateral opening to the diameter of the vibratable mesh is from about 1 to about 2.5, or from about 1.2 to about 2, respectively. Furthermore, the ratio of the internal diameter of the flow channel immediately upstream of the lateral opening to the diameter of the aperture region of the vibratable mesh is from about 1.2 to about 4, such as from about 1.6 to about 3.

In all these embodiments, the flow channel effectively serves as a mixing channel, thereby advantageously obviating the need for a spacious mixing chamber.

The mixing effectiveness may be increased even more by further reducing the internal diameter of the flow channel at a position immediately downstream of the lateral opening; e.g. providing a 'step' which reduces the internal diameter of the flow channel to about 50%, as is described in more detail in WO 2013/132056 A1.

In a further embodiment, the inhalation device (100) of the invention comprises a switch (112) for starting and stopping the operation of the aerosol generator (101), as shown e.g. in FIG. 2. In this context, the operation of the aerosol generator comprises the continuous vibration of the vibratable mesh. In other words, aerosol is continuously generated while the inhalation device is switched on. This is in contrast to many inhalation devices which use breath triggering for switching the aerosol generator on. It has been found that the manual control of the aerosol generator allows the effective inhalation treatment of relatively weak patients, such as paediatric patients, some of which may not easily achieve the inspiratory flow rates or pressures required to trigger a typical inhalation device.

While continuous aerosol generation is commonly believed to be disadvantageous for an effective aerosol delivery as most of the aerosol generated during the exhalation phase of the patient is typically lost, this is not the case in the device according to the invention, due to the face mask and the features associated with it, as described in more detail below.

Optionally, the inhalation device may have more than one switch for operating the aerosol generator, such as two switches located at opposite sides of the inhalation device in order to ensure easy and convenient control by the patient or the caregiver administering the inhalation therapy to the patient. An exemplary embodiment of such an inhalation device using more than one switch (112) can be seen e.g. in FIG. 2 or in FIG. 7.

In a specific embodiment, the inhalation device (100) comprises a) a base unit (118) comprising an electronic controller for controlling the aerosol generator (101), and an upstream portion of the flow channel including the gas inlet opening (104); and b) a mixing channel unit (119), comprising a downstream portion of the flow channel including the lateral opening (111), wherein the downstream portion comprises a segment where the flow channel widens in the downstream direction, said segment being positioned downstream of the lateral opening.

Such an embodiment may for instance be seen in FIG. 1. As can be seen there, the mixing channel unit (119) is formed by double walls; the internal, or inner, walls which face the flow of air and/or aerosol and guide the flow towards the face mask (105); and the external, or outer, walls facing the user. The external, or outer, walls have an almost constant diameter from the base unit (118) to the face mask (105), which is suited to fit safely and comfortably into a user's hand. In contrast, the internal, or inner, walls of the mixing channel unit (119) widen in the downstream direction; i.e. towards the face mask (105). This widening of the downstream portion of the flow channel advantageously slows down the flow velocity of the aerosol-gas-mixture towards the aerosol inlet opening of the face mask. This will reduce the risk of droplets impacting in the mouth and/or the pharyngeal region, as described in WO 2013/132056 A1.

Optionally, the base unit with the electronic controller may further comprise, or house, a battery (e.g. a rechargeable battery), data storage means and/or a USB-port (116) for charging and data retrieval, such as depicted in FIG. 7.

Further optionally, small holes (117) may optionally be provided, e.g. at the rear of the inhalation device (100) as shown in FIGS. 2 and 7, and/or at the bottom side of the inhalation device (100) as shown in FIG. 5; in order to allow for air-cooling of e.g. the electronic controller and any other parts of the base unit (118) which may generate warmth. However, these small holes (117) are not in fluid connection with the flow channel (110).

Optionally, the aerosol generator (101) with the vibrating mesh (102) and the reservoir (103) for the liquid to be nebulised may be provided in a combination component, which is not separable or not easily separable. This reduces the number of losable components of the device and may facilitate cleaning of the rather small aerosol generator. This combination component may further be provided with fixing means such as a key lock (115), which allow for very easy attachment of the combination component to the inhalation device and at the same time ensure, that the aerosol generator—and particularly the end equipped with the vibrating mesh—is inserted properly and at least partially through the lateral opening (111) of the flow channel (110). This is shown e.g. in FIGS. 2 and 4. Moreover, an exemplary arrangement of some components of an inhalation device suitable for the present invention is described in EP 2 724 741 A1.

In one of the embodiments not depicted herein, the device may comprise a flow restrictor in the flow channel upstream of the lateral opening which is adapted to restrict the flow of a gas in the flow channel to a constant flow rate selected in the range from 1 to 5 L/min.

As mentioned, the inhalation device of the invention is particularly useful for delivering a therapeutic aerosol to a patient. Preferably, the use also involves a gas which is supplied at a low flow rate to the gas inlet opening of the device. Such use of the device is an aspect of the invention.

Moreover, the invention provides a method of delivering a nebulised aerosol to a patient, comprising the steps of: (a) providing the inhalation device, or the combination or kit, according to this invention; (b) providing a gas source; and (c) connecting the gas source to the inhalation device such that the gas enters the flow channel through the gas inlet opening at a constant flow rate in the range from 1 to 5 L/min. The preferred and/or optional features of the method include all the preferred and/or optional features described above in the context of the design and operation of the inhalation device itself, or the combination or kit of said device with a pharmaceutical composition for inhalative use as will be described further below.

In a further aspect, the invention provides an assembly, which may also be referred to as an inhalation system, comprising the inhalation device of the invention and a gas source providing a gas at a constant flow rate in the range from 1 to 5 L/min, wherein the gas source is connected to the inhalation device such that the gas enters the flow channel through the gas inlet opening.

The gas provided by the gas source may be selected from oxygen, air, oxygen-enriched air, a mixture of oxygen and nitrogen, and a mixture of helium and oxygen. For the purpose of connecting the inhalation device to the gas source, the gas inlet opening may be shaped as a tube fitting as mentioned above; e.g. a stainless steel fitting so that a gas tube may be used to connect the gas source and the inhalation device.

Again, the preferred and/or optional features as described in the context of the disclosure of the inhalation device itself apply also to the assembly, or inhalation system, comprising the device. And in the same way as the inhalation device itself, the assembly, may be provided in a combination or kit with a pharmaceutical composition for inhalative use.

Using a gas consisting of, or enriched with, oxygen for dispersing the nascent aerosol in the inhalation device is particularly useful for the treatment of certain patients, such as paediatric patients, patients affected with a severe disease of the respiratory system, sedated patients, sleeping patients, or adult patients for whom controlled oral inhalation is not possible or is considerably impeded, such as patients with dementia, COPD, severe asthma attacks, cystic fibrosis, amyotrophic lateral sclerosis, emphysema, or heart failure, or patients under sedation or anaesthesia. Paediatric patients include neonates, infants, toddlers, children, and school children.

In particular, paediatric patients suffering from a lower respiratory tract infection with RSV (LRTI, including bronchiolitis and broncho-pneumonia) may benefit from an additional air and/or oxygen flow during the inhalation treatment. In addition, the inventors observed that an additional gas flow (e.g. 2 L/min) advantageously decreased aerosol deposition within the inhalation device, as described in Example 1 further below.

A further aspect of the invention relates to a combination or kit comprising the inhalation device according to the invention or an assembly according to the invention and a pharmaceutical composition for inhalation use.

In the combination or kit both components, i.e. the inhalation device and the pharmaceutical composition may be combined as separate units sold together as a kit. The same applies mutatis mutandis to a combination or kit of the above mentioned assembly and the pharmaceutical composition.

However, as used herein, a combination does not require the two specified components to be physically combined and sold together, as would typically be the case for a kit, but also includes those combinations that are made by providing one of the components of the combination with instructions that specifically refer to the other component. Moreover, a combination according to the invention also includes the specified inhalation device or assembly comprising, or being filled with, the respective pharmaceutical composition. For the avoidance of doubt, a reference to an inhalation device or assembly filled with a pharmaceutical compositions means that the reservoir of the inhalation device is at least partially filled with the composition.

A pharmaceutical composition, as used herein, is a composition comprising at least one active compound and at least one pharmaceutically acceptable excipient, diluent or carrier. The active compound may also be referred to as active agent, active ingredient, bioactive compound, drug substance, and the like. In the context of the invention, the pharmaceutical composition is for inhalation use, which means that it is formulated and manufactured such that is meets the generally accepted requirements for inhalation use, as for example specified in pharmacopoeias and guidance documents issued by regulatory agencies. For example, a pharmaceutical composition for inhalation contains only excipients which are acceptable for this use, is relatively isotonic, exhibits a relatively neutral pH (in particular a pH in the range from about 4 to about 8), and is sterile.

The pharmaceutical composition may be provided in form of a nebuliser solution, presented in a vial, ampoule, or bottle, or for instance in the form of prefilled single-use cartridges which are emptied into the reservoir of the inhalation device prior to an inhalation treatment.

The pharmaceutical composition may comprise an active agent selected from antibiotics, antiviral agents, bronchodilators, anticholinergics, corticosteroids, hypertonic saline, antibodies, antibody fragments, and immunoglobulin single variable domains. Optionally, the pharmaceutical composition may comprise more than one active agent selected from this group.

In a specific embodiment, the pharmaceutical composition may comprise a polypeptide comprising or consisting of one or more immunoglobulin single variable domains.

The term "immunoglobulin single variable domain", interchangeably used with "single variable domain", defines molecules wherein the antigen binding site is present on, and formed by, a single immunoglobulin domain. This sets immunoglobulin single variable domains apart from "conventional" immunoglobulins or their fragments, wherein two immunoglobulin domains, in particular two variable domains, interact to form an antigen binding site. Typically, in conventional immunoglobulins, a heavy chain variable domain ($V_H$) and a light chain variable domain ($V_L$) interact to form an antigen binding site. In this case, the complementarity determining regions (CDRs) of both $V_H$ and $V_L$ will contribute to the antigen binding site, i.e. a total of 6 CDRs will be involved in antigen binding site formation.

In contrast, the binding site of an immunoglobulin single variable domain is formed by a single $V_H$ or $V_L$ domain. Hence, the antigen binding site of an immunoglobulin single variable domain is formed by no more than three CDRs.

The term "immunoglobulin single variable domain" and "single variable domain" hence does not comprise conventional immunoglobulins or their fragments which require interaction of at least two variable domains for the formation of an antigen binding site. However, these terms do comprise fragments of conventional immunoglobulins wherein the antigen binding site is formed by a single variable domain.

The amino acid sequence and structure of an immunoglobulin single variable domain can be considered—without however being limited thereto—to be comprised of four framework regions or "FR's", which are referred to in the art and herein as "Framework region 1" or "FR1"; as "Framework region 2" or "FR2"; as "Framework region 3" or "FR3"; and as "Framework region 4" or "FR4", respectively; which framework regions are interrupted by three complementary determining regions or "CDR's", which are referred to in the art as "Complementarity Determining Region 1" or "CDR1"; as "Complementarity Determining Region 2" or "CDR2"; and as "Complementarity Determining Region 3" or "CDR3", respectively. Such single variable domains are most preferably such that they comprise an immunoglobulin fold or are capable of forming, under suitable conditions, an immunoglobulin fold. As such, the single variable domain may for example comprise a light chain variable domain sequence (e.g. a $V_L$-sequence); or a heavy chain variable domain sequence (e.g. a $V_H$-sequence or $V_{HH}$ sequence); as long as it is capable of forming a single antigen binding unit (i.e. a functional antigen binding unit that essentially consists of the single variable domain, such that the single antigen binding domain does not need to interact with another variable domain to form a functional antigen binding unit, as is for example the case for the variable domains that are present in for example conventional antibodies and scFv fragments that need to interact with another variable domain—e.g. through a $V_H/V_L$ interaction—to form a functional antigen binding domain).

In one embodiment of the invention, the immunoglobulin single variable domains are light chain variable domain sequences (e.g. a $V_L$-sequence), or heavy chain variable domain sequences (e.g. a $V_H$-sequence); more specifically, the immunoglobulin single variable domains can be heavy chain variable domain sequences that are derived from a conventional four-chain antibody or heavy chain variable domain sequences that are derived from a heavy chain antibody.

For example, the single variable domain or immunoglobulin single variable domain may be a (single) domain antibody, a "dAb" or dAb or a Nanobody (including but not limited to a $V_{HH}$); other single variable domains, or any suitable fragment of any one thereof.

For a general description of (single) domain antibodies, reference is also made to the prior art cited herein, as well as to EP 0368684 A1. For the term "dAb's", reference is for example made to Ward et al. 1989 (Nature 341: 544-546), to Holt et al. 2003 (Trends Biotechnol. 21: 484-490); as well as to for example WO 2004/068820 A2, WO 2006/030220 A1, WO 2006/003388 A2, WO 2006/059108 A2, WO 2007/049017 A2, WO 2007/085815 A2. It should also be noted that, although less preferred in the context of the present invention because they are not of mammalian origin, single variable domains can be derived from certain species of shark (for example, the so-called "IgNAR domains", see for example WO 2005/18629 A1).

In particular, the immunoglobulin single variable domain may be a Nanobody® (as defined herein) or a suitable fragment thereof. (Note: Nanobody®, Nanobodies® and Nanoclone® are registered trademarks of Ablynx N.V.). For a further description of $V_{HH}$'s and Nanobodies, reference is made to the review article by Muyldermans 2001 (Reviews in Molecular Biotechnology 74: 277-302), WO 2008/101985 A2 and WO 2008/142164 A2. As described in these references, Nanobodies (in particular $V_{HH}$ sequences and partially humanized $V_{HH}$ sequences) can in particular be characterized by the presence of one or more "Hallmark residues" in one or more of the framework sequences. A further description of the Nanobodies, including humanization and/or camelization of Nanobodies, as well as other modifications, parts or fragments, derivatives or "Nanobody fusions", multivalent constructs (including some non-limiting examples of linker sequences) and different modifications to increase the half-life of the Nanobodies and their preparations can be found e.g. in WO 2008/101985 A2 and WO 2008/142164 A2.

Thus, in the meaning of the present invention, the term "immunoglobulin single variable domain" or "single variable domain" comprises polypeptides which are derived from a non-human source, preferably a camelid, preferably a camelid heavy chain antibody. They may be humanized, as previously described. Moreover, the term comprises polypeptides derived from non-camelid sources, e.g. mouse or human, which have been "camelized", as e.g. described in Davies and Riechmann 1994 (FEBS 339: 285-290), 1995 (Biotechnol. 13: 475-479), 1996 (Prot. Eng. 9: 531-537) and Riechmann and Muyldermans 1999 (J. Immunol. Methods 231: 25-38).

Again, such Nanobodies may be derived in any suitable manner and from any suitable source, and may for example be naturally occurring $V_{HH}$ sequences (i.e. from a suitable species of Camelid) or synthetic or semi-synthetic amino acid sequences, including but not limited to partially or fully "humanized" $V_{HH}$, "camelized" immunoglobulin sequences (and in particular camelized $V_H$), as well as Nanobodies and/or $V_{HH}$ that have been obtained by techniques such as affinity maturation (for example, starting from synthetic, random or naturally occurring immunoglobulin sequences, such as $V_{HH}$ sequences), CDR grafting, veneering, combining fragments derived from different immunoglobulin sequences, PCR assembly using overlapping primers, and similar techniques for engineering immunoglobulin sequences well known to the skilled person; or any suitable combination of any of the foregoing.

In a specific embodiment, the strength of the pharmaceutical composition is adapted for a paediatric patient.

In a particular embodiment, the pharmaceutical composition comprises an anti-RSV agent. As used herein, an anti-RSV agent is an active agent capable of treating or managing an infection with human respiratory syncytial virus (RSV). The anti-RSV agent may be a small molecular antiviral compound or a biological such as an antibody or an antibody fragment. An example of an antibody that may be used according to the invention is palivizumab, which is a monoclonal antibody directed against the RSV surface fusion protein.

In a further specific embodiment, the anti-RSV agent may e.g. be a polypeptide comprising or essentially consisting of one or more anti-RSV immunoglobulin single variable domains. It has been found by the inventors that a pharmaceutical composition comprising such agent may be effectively delivered to paediatric patients including neonates, infants and even toddlers. It is believed that these polypeptides have never before been effectively delivered to such patients, using a known inhalation device.

The anti-RSV agent used according to the invention may in particular be a polypeptide comprising or essentially consisting of one or more anti-RSV immunoglobulin single variable domains, wherein the anti-RSV immunoglobulin single variable domain comprises a CDR1 having the amino acid sequence of SEQ ID NO: 46, a CDR2 having the amino acid sequence of one of SEQ ID NOs: 49-50, and a CDR3 having the amino acid sequence of SEQ ID NO: 61 (see also Table A-1).

In a preferred embodiment, the anti-RSV immunoglobulin single variable domain is selected from one of the amino acid sequences of SEQ ID NOs: 1-34 (Table A-2).

In a preferred embodiment, the polypeptides encompass constructs comprising three or more antigen binding units in the form of single variable domains, as outlined above. For example, three or more immunoglobulin single variable domains that bind hRSV (also referred to herein as "anti-hRSV immunoglobulin single variable domain(s)") can be linked to form a trivalent or multivalent construct. Preferably the polypeptide of the invention consists of three anti-hRSV immunoglobulin single variable domains.

In the polypeptides described above, the anti-hRSV immunoglobulin single variable domains may be linked directly to each other and/or via one or more suitable linkers or spacers. Suitable spacers or linkers for use in multivalent polypeptides will be clear to the skilled person, and may generally be any linker or spacer used in the art to link amino acid sequences. Preferably, said linker or spacer is suitable for use in constructing proteins or polypeptides that are intended for pharmaceutical use.

Some particularly preferred spacers include the spacers and linkers that are used in the art to link antibody fragments or antibody domains. These include the linkers mentioned in the general background art cited above, as well as for example linkers that are used in the art to construct diabodies or ScFv fragments (in this respect, however, it should be noted that, whereas in diabodies and in ScFv fragments, the linker sequence used should have a length, a degree of flexibility and other properties that allow the pertinent $V_H$ and $V_L$ domains to come together to form the complete antigen-binding site, there is no particular limitation on the length or the flexibility of the linker used in the polypeptide of the invention, since each immunoglobulin single variable domain by itself forms a complete antigen-binding site).

For example, a linker may be a suitable amino acid sequence, and in particular amino acid sequences of between 1 and 50, preferably between 1 and 30, such as between 1 and 20 or between 1 and 10 amino acid residues. Widely used peptide linkers comprise Gly-Ser repeats, e.g. (Gly)4-Ser in one, two, three, four, five, six or more repeats, or for example of the type $(gly_x ser_y)_z$, such as (for example $(gly_4 ser)_3$ or $(gly_3 ser_2)_3$, as described in WO 99/42077 A2, or hinge-like regions such as the hinge regions of naturally occurring heavy chain antibodies or similar sequences (such as described in WO 94/04678 A1). Some other particularly preferred linkers are poly-alanine (such as AAA), as well as the linkers mentioned in Table A-4.

In a further preferred embodiment, the anti-RSV agent is a polypeptide selected from one of the amino acid sequences of SEQ ID NOs: 65-85; such as e.g. the amino acid sequence of SEQ ID NO: 71 (Table A-3).

In one of the preferred embodiments, the pharmaceutical composition comprises the anti-RSV polypeptide at a concentration of about 10 to 100 mg/mL, such as 50 mg/mL or more, and/or a dose of the agent in a volume from about 0.15 mL to about 0.40 mL.

Preferably, the combination or kit comprises instructions to administer such active agent based on one or more of these anti-RSV immunoglobulin single variable domains, such as e.g. one of SEQ ID NOs: 65-85, using daily doses of about 1 to 2 mg/kg body weight, in particular if the patient is a paediatric patient, preferably of not more than 2 years of age, or not more than 3 years.

Earlier modelling studies of the inventors for pediatric populations with these compounds revealed that the dose determination was mainly guided by pulmonary delivery, distribution and drug absorption differences between the developing child's lung and the adult's lung. The primary driving parameter for systemic as well as local pharmacokinetics in the RSV infected children appeared to be the amount of drug in alveolar absorption space.

The above described polypeptides, and in particular the polypeptides selected from one of the amino acid sequences of SEQ ID NOs: 65-85, bind the F-protein of hRSV with a $K_D$ of $5 \times 10^{-10}$ M or less (as measured by immunoassay), and neutralize hRSV with an IC90 of 90 ng/mL or less (as measured in a micro-neutralization assay). A clinically meaningful reduction of RSV activity is obtained at a target concentration of 9 µg/mL.

This concentration of 9 µg/mL may be reached in the alveolar space using a deposited dose of 0.020 to 0.040 mg/kg daily, preferably 0.020 to 0.035 mg/kg daily, such as e.g. 0.024 mg/kg daily. For this purpose the polypeptide may be administered to a child by inhalation at a nominal dose of 1.00 to 2.00 mg/kg daily, preferably 1.00 to 1.75 mg/kg daily, such as e.g. 1.20 mg/kg daily.

This estimation is based on aerosol deposition studies performed with the Sophia Anatomical Infant Nose Throat (SAINT) model in which the polypeptide, e.g. SEQ ID NO: 71, was administered with an inhalation device according to the invention, more specifically a vibrating mesh nebuliser with a constant flow rate of 2 L/min additional air or oxygen (see Example 1). The results showed that, from the total dose filled into the reservoir of the nebuliser, approximately 20% is expected to be inhaled.

Optionally, the combination or kit of the inhalation device or assembly with the pharmaceutical composition for inhalation use comprising an anti-RSV agent further comprises a bronchodilator. The bronchodilator may be incorporated within the pharmaceutical composition which also contains the anti-RSV agent. Alternatively, it may be provided in a separate pharmaceutical composition which may be filled into the reservoir of the inhalation device separately from, or along with, the composition comprising the anti-RSV agent.

There are two main classes of bronchodilators, namely the sympathomimetics, including short-acting and long-acting beta2-mimetics; and the anticholinergics.

In one embodiment, the bronchodilator belongs to the class of beta2-mimetics. Optionally, the beta2-mimetic is a long-acting beta2-mimetic and in particular a bronchodilator selected from formoterol, salmeterol, or salt and/or mixtures thereof.

Alternatively, the bronchodilator may be a short-acting beta2-mimetic substance, such as a bronchodilator selected from salbutamol, terbutaline, pirbuterol, fenoterol, tulobuterol, levosabutamol, and the salts and mixtures thereof. In a specific embodiment, the bronchodilator is salbutamol and is administered at a dose of 200 micrograms.

In a further alternative embodiment, the bronchodilator belongs to the class of anticholinergics, e.g. an anticholinergic agent selected from tiotropium, oxitropium, ipratropium bromide and mixtures thereof.

Without being limiting, additional bronchodilators for use in the products and methods of the invention include albuterol, bitolterol, ephedrine, epinephrine, isoetharine, isoproterenol, metaproterenol, pirbuterol, racepinephrine, ritodrine, terbutaline, levosabutamol, levabuterol, clenbuterol, amphetamine, methamphetamine, cocaine, theophylline, caffeine, theobromine, tetrahydrocannabinol (THC), and methylendioxypyrovaleron (MDPV).

As mentioned, the inhalation device according to the invention or the assembly of this inhalation device with a gas source as described above, or the respective kits or combinations with a pharmaceutical composition for inhalative use, may be employed for use in the treatment of a patient suffering from a disease affecting the respiratory system.

The disease may be respiratory infection (an infection of the respiratory tract), such as a Respiratory Syncytial Virus (RSV) infection, and more specifically a RSV lower respiratory tract infection.

The patient suffering from the respiratory disease may be a paediatric patient, such as a neonate, an infant, a toddler, or a school child. In one embodiment, the patient may be a child younger than 24 months; in one embodiment, the patient may be a child younger than 36 months, more specifically a child aged 1 month to less than 24 months, 1 month to less than 36 months, 5 months to less than 24 months, or 5 months to less than 36 months. In a particular embodiment, the child is hospitalised for RSV lower respiratory tract infection.

Alternatively, the patient may be an adult for whom controlled oral inhalation is not possible or is considerably impeded, such as patients with dementia, mental impairments, COPD, severe asthma attacks, cystic fibrosis, amyotrophic lateral sclerosis, emphysema or heart failure, or patients under sedation or anaesthesia.

In a further aspect, the invention relates to a method of delivering a nebulised aerosol to a young child, such as a neonate, infant or toddler, who is suffering from an RSV-infection, comprising the steps of (a) providing the inhalation device according to this invention; (b) providing a gas source; (c) connecting the gas source to the inhalation device such that the gas enters the flow channel through the gas inlet opening at a constant flow rate in the range from 1 to 5 L/min, in particular at 2 L/min; and (d) providing a nebuliser solution comprising at least an anti-RSV agent selected from one of the amino acid sequences of SEQ ID NOs: 65-85.

Example 1—Deposition Study for an Anti-RSV Nanobody Agent Using the Inhalation System According to the Invention SEQ ID NO: 71 (Table A-3) was used in an experiment evaluating the effect of simulated inhalation and aerosol administration, with and without air supply, on the inhaled drug amount.

The determination of the inhaled dose was performed with the Sophia Anatomical Infant Nose Throat (SAINT) model; an anatomically correct representation of the upper airways of a 9 month old child, which is built using stereolithographic techniques and used for studying aerosol deposition in young children (see e.g. Janssens et al.; J Aerosol Med. 2001 Winter; 14(4):433-41.).

Figure 8:
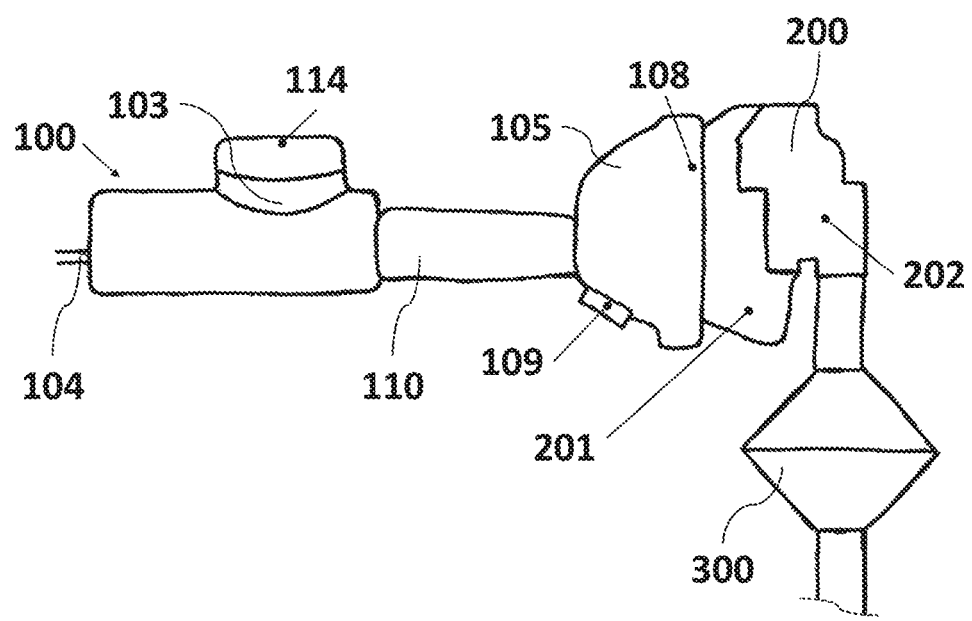
FIG. 8 shows an experimental set-up with a specific embodiment of the inhalation device according to the invention connected to a SAINT model

The experimental set-up is represented in FIG. 8; showing the inhalation device (100) with the reservoir (103), the gas inlet opening (104), the flow channel, or mixing channel, (110) and the face mask (105) with the one-way exhalation valve or two-way inhalation/exhalation valve (109). FIG. 8 further shows the patient contacting surface (108) in tight contact with the face/throat portion (201) of the SAINT model (200), the nasal portion (202) of the SAINT model, and a glass fibre filter assembly (300) representing the lower respiratory tract. The glass fibre filter assembly (300) is connected to a breath simulator, which in turn is connected to, and controlled by a computer; both not depicted in FIG. 8.

The nebuliser was connected to the SAINT model via the attached face mask covering nose and mouth of the model. Behind the SAINT model (in the direction of the air, or aerosol flow), a glass fibre filter representing the lower respiratory tract, was connected. Aerosol was collected during product nebulisation and simulated administration, using a breath simulator (ASL 5000, IngMar Medical, USA) to mimic typical breathing parameters such as respiratory rate, tidal volume and inhalation/exhalation ratio.

Different breathing parameter protocols were employed; e.g. an inhalation/exhalation ratio 1:3 as common for infants, and a tidal volume of 45 mL and a respiratory rate of 40 breaths per minute, which represents the distressed breathing pattern of a 5 months old infant (see e.g. Totapally et al.; Critical Care 2002, 6:160-165).

The reservoir of the inhalation device was filled with 400 μL of the SEQ ID NO: 71 formulation using a 1-mL syringe (i.e. the filling dose). The inhalation device was weighed before and after filling, in order to determine the filling dose. Then continuous nebulisation was started in three different additional air supply settings:
1) no additional air supply; gas inlet opening is open,
2) no additional air supply; gas inlet opening is blocked, and
3) additional air supply at 2 L/min via the gas inlet opening.

Nebulisation times until auto shut-off of the device were recorded. After nebulisation, the device components (i.e., reservoir, mixing channel, face mask) and the SAINT model compartments (i.e., nasopharyngeal airway and face/oral cavity) and the lower respiratory tract glass fibre filter were swilled with a defined volume of appropriate solvent (here distilled water) to collect samples and measure any deposited SEQ ID NO: 71. The samples were analysed for concentration via conductivity meter using calibration curves (because of the diluted SEQ ID NO: 71 concentrations in the collected samples, it was more sensitive to measure the conductivity of sodium chloride and phosphate salts present in the SEQ ID NO: 71 formulation).

The recorded deposition data (see Table 1 below) were used to determine, or calculate, e.g. the emitted dose, delivered dose, inhaled dose, lung dose, residual dose (all in milligrams and/or percentages of the filling dose).

The filling dose is the amount of drug that in theory could be nebulised and provided for inhalation; disregarding e.g. any losses into the ambient air, amounts nebulised during the exhalation phase, or losses within the device.

The exhaled dose is the drug amount dissipated in, or lost to, the environment; calculated as the difference of the total dose minus the cumulative drug amounts deposited within the device without the face mask (i.e. mainly in the aerosol generator and the flow channel, or mixing channel), in the face mask, in the SAINT model components (both nasal and face/throat) and in the glass fibre filter.

The emitted dose is the drug amount emitted by the device at the downstream end of the mixing channel; calculated as the sum of the exhaled dose plus the delivered dose. The emitted dose may also be understood as the total dose minus the drug amount deposited within the nebuliser and its mixing channel (but not the face mask).

The delivered dose is the drug amount available for inhalation; calculated from the cumulative amounts of drug deposited in the face mask, the SAINT model components (both nasal and face/throat) and the glass fibre filter (the latter is also referred to as the "lung dose").

The inhaled dose is the drug amount actually inhaled; i.e. the cumulative amounts of drug deposited in the nasal SAINT model component and the glass fibre filter.

The lung dose is the drug amount deposited in the glass fibre filter which represents the lower respiratory tract.

Table 1 shows the distribution of the drug, as measured in the described experiment, as well as some calculated doses in percentage of the filling dose:

| | | Percentage of filling dose [%] | | | | | | | |
|---|---|---|---|---|---|---|---|---|---|
| | | Measured depositions | | | | | Calculated | | |
| | Neb. | device | | SAINT | | glass fibre | | | |
| Additional air supply setting | Time [sec] | w/o mask | face mask | (face, throat) | SAINT (nasal) | filter (=lung dose) | Inhaled dose | Delivered dose | Exhaled dose/losses |
| 1 (no air) | 100 | 54.6 | 8.1 | 0.9 | 3.6 | 5.2 | 8.8 | 17.8 | 27.6 |
| 2 (blocked) | 133 | 86.2 | 5.3 | 0.8 | 0.5 | 2.3 | 2.9 | 8.9 | 4.9 |
| 3 (2 L/min) | 130 | 20.7 | 4.6 | 1.8 | 4.6 | 8.6 | 13.1 | 19.5 | 59.8 |

These data show that the dose inhaled and the dose deposited in the glass fibre filter/the lower respiratory tract ("lung" dose) is higher when the air supply is present. Also, the dose deposited within the device components is reduced significantly by the additional air supply.

Tables

TABLE A-1

Amino acid sequences of anti-hRSV immunoglobulin single variable domains (with FR and CDR sequences indicated)

| Nanobody | SEQ ID | FR1 | SEQ ID | CDR 1 | SEQ ID | FR2 | SEQ ID | CDR 2 | SEQ ID | FR3 | SEQ ID | CDR 3 | SEQ ID | FR4 | SEQ ID |
|---|---|---|---|---|---|---|---|---|---|---|---|---|---|---|---|
| NC41 | 1 | EVQLVESGGGLVQAGG SLSLSISCAASGSGSLS | 35 | NYVLG | 46 | WFRQAPG KEREFVA | 47 | AINWRGDITI GPPNVEG | 49 | RFTISRDNAKNTGYLQ MNSLAPDDTAVYYCGA | 51 | GTPLNPGAYI YDWSYDY | 61 | WGRGTQVTVSS | 62 |
| NC41 E1D | 2 | DVQLVESGGGLVQAGG SLSLSISCAASGSGSLS | 36 | NYVLG | 46 | WFRQAPG KEREFVA | 47 | AINWRGDITI GPPNVEG | 49 | RFTISRDNAKNTGYLQ MNSLAPDDTAVYYCGA | 51 | GTPLNPGAYI YDWSYDY | 61 | WGRGTQVTVSS | 62 |
| NC41v01 | 3 | EVQLESGGGLVQPGG SLRLSCAASGSGSLS | 37 | NYVLG | 46 | WFRQAPG KGREFVA | 48 | AINWRGDITI GPPNVEG | 49 | RFTISRDNAKNTLYLQ MNSLAPEDTAVYYCGA | 52 | GTPLNPGAYI YDWSYDY | 61 | WGQGTLVTVSS | 63 |
| NC41v02 | 4 | EVQLLESGGGLVQPGG SLRLSCAASGSGSLS | 38 | NYVLG | 46 | WFRQAPG KGREFVA | 48 | AINWRGDITI GPPNVEG | 49 | RFTISRENSKNTLYLQ MNSLAPEDTAVYYCGA | 53 | GTPLNPGAYI YDWSYDY | 61 | WGQGTLVTVSS | 63 |
| NC41v03 | 5 | EVQLLESGGGLVQPGG SLRLSCAASGSGSLS | 38 | NYVLG | 46 | WFRQAPG KGREFVA | 48 | AINWRGDITI GPPNVEG | 49 | RFTISRENSKNTLYLQ MNSLRPEDTAVYYCGA | 54 | GTPLNPGAYI YDWSYDY | 61 | WGQGTLVTVSS | 63 |
| NC41v03 FAD | 6 | DVQLLESGGGLVQPGG SLRLSCAASGSGSLS | 39 | NYVLG | 46 | WFRQAPG KGREFVA | 48 | AINWRGDITI GPPNVEG | 49 | RFTISRENSKNTLYLQ MNSLRPEDTAVYYCGA | 54 | GTPLNPGAYI YDWSYDY | 61 | WGQGTLVTVSS | 63 |
| NC41v04 | 7 | EVQLLESGGGLVQPGG SLSLSCAASGSGSLS | 40 | NYVLG | 46 | WFRQAPG KGREFVA | 48 | AINWRGDITI GPPNVEG | 49 | RFTISRENSKNTLYLQ MNSLRPEDTAVYYCGA | 55 | GTPLNPGAYI YDWSYDY | 61 | WGQGTLVTVSS | 63 |
| NC41v05 | 8 | EVQLLESGGGLVQPGG SLSLSCAASGSGSLS | 40 | NYVLG | 46 | WFRQAPG KGREFVA | 48 | AINWRGDITI GPPNVEG | 49 | RFTISRENSKNTLYLQ MNSLRPEDTAVYYCGA | 53 | GTPLNPGAYI YDWSYDY | 61 | WGQGTLVTVSS | 63 |
| NC41v06 | 9 | EVQLLESGGGLVQPGG SLRLSCAASGSGSLS | 37 | NYVLG | 46 | WFRQAPG KGREFVA | 48 | AINWRDDITI GPPNVEG | 50 | RFTISRDNAKNTLYLQ MNSLRPEDTAVYYCGA | 56 | GTPLNPGAYI YDWSYDY | 61 | WGQGTLVTVSS | 63 |
| NC41v06 FAD | 10 | DVQLLESGGGLVQPGG SLRLSCAASGSGSLS | 41 | NYVLG | 46 | WFRQAPG KGREFVA | 48 | AINWRDDITI GPPNVEG | 50 | RFTISRDNAKNTLYLQ MNSLRPEDTAVYYCGA | 56 | GTPLNPGAYI YDWSYDY | 61 | WGQGTLVTVSS | 63 |
| NC41v07 | 11 | EVQLLESGGGLVQPGG SLSLSCAASGSGSLS | 40 | NYVLG | 46 | WFRQAPG KGREFVA | 48 | AINWRGDITI GPPNVEG | 49 | RFTISRDNAKNTLYLQ MNSLAPDDTAVYYCGA | 57 | GTPLNPGAYI YDWSYDY | 61 | WGQGTLVTVSS | 63 |
| NC41v08 | 12 | EVQLLESGGGLVQPGG SLSLSCAASGSGSLS | 40 | NYVLG | 46 | WFRQAPG KGREFVA | 48 | AINWRGDITI GPPNVEG | 49 | RFTISRDNAKNTLYLQ MNSLRPEDTAVYYCGA | 56 | GTPLNPGAYI YDWSYDY | 61 | WGQGTLVTVSS | 63 |
| NC41v09 | 13 | EVQLLESGGGLVQPGG SLSLSCAASGSGSLS | 40 | NYVLG | 46 | WFRQAPG KGREFVA | 48 | AINWRGDITI GPPNVEG | 49 | RFTISRENSKNTLYLQ MNSLRPDDTAVYYCGA | 55 | GTPLNPGAYI YDWSYDY | 61 | WGQGTLVTVSS | 63 |
| NC41v10 | 14 | EVQLLESGGGLVQPGG SLSLSCAASGSGSLS | 40 | NYVLG | 46 | WFRQAPG KGREFVA | 48 | AINWRGDITI GPPNVEG | 49 | RFTISRDNAKNTGYLQ MNSLAPDDTAVYYCGA | 51 | GTPLNPGAYI YDWSYDY | 61 | WGQGTLVTVSS | 63 |

TABLE A-1-continued

Amino acid sequences of anti-hRSV immunoglobulin single variable domains (with FR and CDR sequences indicated)

| Nanobody | SEQ ID | FR1 | SEQ ID | CDR 1 | SEQ ID | FR2 | SEQ ID | CDR 2 | SEQ ID | FR3 | SEQ ID | CDR 3 | SEQ ID | FR4 | SEQ ID |
|---|---|---|---|---|---|---|---|---|---|---|---|---|---|---|---|
| NC41v11 | 15 | EVQLLESGGGLVQAGG SLSLSCAASGGSLS | 42 | NYVLG | 46 | WFRQAPG KGREFVA | 47 | AINWRGDITI GPPNVEG | 49 | RFTISRDNAKNTGYLQ MNSLAPDDTAVYYCGA | 51 | GTPLNPGAYI YDWSYDY | 61 | WGQGTLVTVSS | 63 |
| NC41v12 | 16 | EVQLLESGGGLVQPGG SLSLSCAASGGSLS | 40 | NYVLG | 46 | WFRQAPG KEREFVA | 47 | AINWRGDITI GPPNVEG | 49 | RFTISRDNAKNTGYLQ MNSLAPDDTAVYYCGA | 51 | GTPLNPGAYI YDWSYDY | 61 | WGQGTLVTVSS | 63 |
| NC41v13 | 17 | EVQLLESGGGLVQPGG SLRLSCAASGGSLS | 37 | NYVLG | 46 | WFRQAPG KGREFVA | 48 | AINWRGDITI GPPNVEG | 49 | RFTISRDNAKNTGYLQ MNSLAPEDTAVYYCGA | 58 | GTPLNPGAYI YDWSYDY | 61 | WGQGTLVTVSS | 63 |
| NC41v14 | 18 | EVQLLESGGGLVQPGG SLRLSCAASGGSLS | 37 | NYVLG | 46 | WFRQAPG KGREFVA | 48 | AINWRGDITI GPPNVEG | 49 | RFTISRENSKNTLYLQ MNSLAPEDTAVYYCGA | 53 | GTPLNPGAYI YDWSYDY | 61 | WGQGTLVTVSS | 63 |
| NC41v15 | 19 | EVQLLESGGGLVQAGG SLRLSCAASGGSLS | 43 | NYVLG | 46 | WFRQAPG KGREFVA | 48 | AINWRGDITI GPPNVEG | 49 | RFTISRDNAKNTLYLQ MNSLAPEDTAVYYCGA | 52 | GTPLNPGAYI YDWSYDY | 61 | WGQGTLVTVSS | 63 |
| NC41v17 | 20 | EVQLLESGGGLVQPGG SLRLSCAASGGSLS | 37 | NYVLG | 46 | WFRQAPG KGREFVA | 48 | AINWRGDITI GPPNVEG | 49 | RFTISRENSKNTLYLQ MNSLRPEDTAVYYCGA | 54 | GTPLNPGAYI YDWSYDY | 61 | WGQGTLVTVSS | 63 |
| NC41v17 E1D | 21 | DVQLLESGGGLVQPGG SLRLSCAASGGSLS | 41 | NYVLG | 46 | WFRQAPG KGREFVA | 48 | AINWRGDITI GPPNVEG | 49 | RFTISRENSKNTLYLQ MNSLRPEDTAVYYCGA | 54 | GTPLNPGAYI YDWSYDY | 61 | WGQGTLVTVSS | 63 |
| NC41v18 | 22 | EVQLLESGGGLVQPGG SLRLSCAASGGSLS | 37 | NYVLG | 46 | WFRQAPG KGREFVA | 48 | AINWRDDITI GPPNVEG | 50 | RFTISRENSKNTLYLQ MNSLRPEDTAVYYCGA | 54 | GTPLNPGAYI YDWSYDY | 61 | WGQGTLVTVSS | 63 |
| NC41v18 FAD | 23 | DVQLLESGGGLVQPGG SLRLSCAASGGSLS | 41 | NYVLG | 46 | WFRQAPG KGREFVA | 48 | AINWRDDITI GPPNVEG | 50 | RFTISRENSKNTLYLQ MNSLRPEDTAVYYCGA | 54 | GTPLNPGAYI YDWSYDY | 61 | WGQGTLVTVSS | 63 |
| NC41v19 | 24 | EVQLVESGGGLVQPGG SLRLSCAASGGSLS | 44 | NYVLG | 46 | WFRQAPG KGREFVA | 47 | AINWRGDITI GPPNVEG | 49 | RFTISRDNAKNTGYLQ MNSLAPDDTAVYYCGA | 51 | GTPLNPGAYI YDWSYDY | 61 | WGQGTLVTVSS | 63 |
| NC41v20 | 25 | EVQLVESGGGLVQPGG SLRLSCAASGGSLS | 44 | NYVLG | 46 | WFRQAPG KEREFVA | 47 | AINWRGDITI GPPNVEG | 49 | RFTISRDNAKNTGYLQ MNSLAPDDTAVYYCGA | 59 | GTPLNPGAYI YDWSYDY | 61 | WGQGTLVTVSS | 63 |
| NC41v21 | 26 | EVQLVESGGGLVQPGG SLRLSCAASGGSLS | 44 | NYVLG | 46 | WFRQAPG KEREFVA | 47 | AINWRGDITI GPPNVEG | 49 | RFTISRDNAKNTGYLQ MNSLAPEDTAVYYCGA | 58 | GTPLNPGAYI YDWSYDY | 61 | WGQGTLVTVSS | 63 |
| NC41v21 FAD | 27 | DVQLVESGGGLVQPGG SLRLSCAASGGSLS | 45 | NYVLG | 46 | WFRQAPG KEREFVA | 47 | AINWRGDITI GPPNVEG | 49 | RFTISRDNAKNTGYLQ MNSLAPEDTAVYYCGA | 58 | GTPLNPGAYI YDWSYDY | 61 | WGQGTLVTVSS | 63 |
| NC41v22 | 28 | EVQLVESGGGLVQPGG SLRLSCAASGGSLS | 44 | NYVLG | 46 | WFRQAPG KEREFVA | 47 | AINWRGDITI GPPNVEG | 49 | RFTISRDNAKNTGYLQ MNSLRPEDTAVYYCGA | 60 | GTPLNPGAYI YDWSYDY | 61 | WGQGTLVTVSS | 63 |

TABLE A-1-continued

Amino acid sequences of anti-hRSV immunoglobulin single variable domains (with FR and CDR sequences indicated)

| Nanobody | SEQ ID | FR1 | SEQ ID | CDR 1 | SEQ ID | FR2 | SEQ ID | CDR 2 | SEQ ID | FR3 | SEQ ID | CDR 3 | SEQ ID | FR4 | SEQ ID |
|---|---|---|---|---|---|---|---|---|---|---|---|---|---|---|---|
| NC41v22 FAD | 29 | DVQLVESGGGLVQPGG SLRLSCAASGGSLS | 45 | NYVLG | 46 | WFRQAPG KEREFVA | 47 | AINWRGDITI GPPNVEG | 49 | RFTISRDNAKNTGYLQ MNSLRPEDTAVYYCGA | 60 | GTPLNPGAYI YDWSYDY | 61 | WGQGTLVTVSS | 63 |
| NC41v23 | 30 | EVQLVESGGGLVQPGG SLRLSCAASGGSLS | 44 | NYVLG | 46 | WFRQAPG KEREFVA | 47 | AINWRGDITI GPPNVEG | 49 | RFTISRDNAKNTGYLQ MNSLAPDDTAVYYCGA | 51 | GTPLNPGAYI YDWSYDY | 61 | WGRGTLVTVSS | 64 |
| NC41v24 | 31 | EVQLVESGGGLVQPGG SLRLSCAASGGSLS | 44 | NYVLG | 46 | WFRQAPG KEREFVA | 47 | AINWRGDITI GPPNVEG | 49 | RFTISRDNAKNTGYLQ MNSLRPDDTAVYYCGA | 59 | GTPLNPGAYI YDWSYDY | 61 | WGRGTLVTVSS | 64 |
| NC41v25 | 32 | EVQLVESGGGLVQPGG SLRLSCAASGGSLS | 44 | NYVLG | 46 | WFRQAPG KEREFVA | 47 | AINWRGDITI GPPNVEG | 49 | RFTISRDNAKNTGYLQ MNSLAPEDTAVYYCGA | 58 | GTPLNPGAYI YDWSYDY | 61 | WGRGTLVTVSS | 64 |
| NC41v26 | 33 | EVQLVESGGGLVQPGG SLRLSCAASGGSLS | 44 | NYVLG | 46 | WFRQAPG KEREFVA | 47 | AINWRGDITI GPPNVEG | 49 | RFTISRDNAKNTGYLQ MNSLRPEDTAVYYCGA | 60 | GTPLNPGAYI YDWSYDY | 61 | WGRGTLVTVSS | 64 |
| NC41v26 FAD | 34 | DVQLVESGGGLVQPGG SLRLSCAASGGSLS | 45 | NYVLG | 46 | WFRQAPG KEREFVA | 47 | AINWRGDITI GPPNVEG | 49 | RFTISRDNAKNTGYLQ MNSLRPEDTAVYYCGA | 60 | GTPLNPGAYI YDWSYDY | 61 | WGRGTLVTVSS | 64 |

TABLE A-2

Amino acid sequences of anti-hRSV immunoglobulin single variable domains

| Nanobody® | SEQ ID NO: | Sequence |
|---|---|---|
| NC41 | 1 | EVQLVESGGGLVQAGGSLSISCAASGGSLSNYVLGWFRQAPGKEREFVAAINWRGDITIGPPNVEGRFTISRDNAKNTGYLQMNSLAPDDTAVYYCGAGTPLNPGAYIYDWSYDYWGRGTQVTVSS |
| NC41 E1D | 2 | DVQLVESGGGLVQAGGSLSISCAASGGSLSNYVLGWFRQAPGKEREFVAAINWRGDITIGPPNVEGRFTISRDNAKNTGYLQMNSLAPDDTAVYYCGAGTPLNPGAYIYDWSYDYWGRGTQVTVSS |
| NC41v01 | 3 | EVQLLESGGGLVQPGGSLRLSCAASGGSLSNYVLGWFRQAPGKGREFVAAINWRGDITIGPPNVEGRFTISRDNAKNTLYLQMNSLAPEDTAVYYCGAGTPLNPGAYIYDWSYDYWGQGTLVTVSS |
| NC41v02 | 4 | EVQLLESGGGLVQPGGSLRISCAASGGSLSNYVLGWFRQAPGKGREFVAAINWRGDITIGPPNVEGRFTISRDNSKNTLYLQMNSLAPEDTAVYYCGAGTPLNPGAYIYDWSYDYWGQGTLVTVSS |
| NC41v03 | 5 | EVQLLESGGGLVQPGGSLRISCAASGGSLSNYVLGWFRQAPGKGREFVAAINWRGDITIGPPNVEGRFTISRDNSKNTLYLQMNSLRPEDTAVYYCGAGTPLNPGAYIYDWSYDYWGQGTLVTVSS |
| NC41v03 E1D | 6 | DVQLLESGGGLVQPGGSLRISCAASGGSLSNYVLGWFRQAPGKGREFVAAINWRGDITIGPPNVEGRFTISRDNSKNTLYLQMNSLRPEDTAVYYCGAGTPLNPGAYIYDWSYDYWGQGTLVTVSS |
| NC41v04 | 7 | EVQLLESGGGLVQPGGSLSISCAASGGSLSNYVLGWFRQAPGKGREFVAAINWRGDITIGPPNVEGRFTISRDNSKNTLYLQMNSLRPDDTAVYYCGAGTPLNPGAYIYDWSYDYWGQGTLVTVSS |
| NC41v05 | 8 | EVQLLESGGGLVQPGGSLSISCAASGGSLSNYVLGWFRQAPGKGREFVAAINWRGDITIGPPNVEGRFTISRDNSKNTLYLQMNSLAPEDTAVYYCGAGTPLNPGAYIYDWSYDYWGQGTLVTVSS |
| NC41v06 | 9 | EVQLLESGGGLVQPGGSLRLSCAASGGSLSNYVLGWFRQAPGKGREFVAAINWRDDITIGPPNVEGRFTISRDNAKNTLYLQMNSLRPEDTAVYYCGAGTPLNPGAYIYDWSYDYWGQGTLVTVSS |
| NC41v06 E1D | 10 | DVQLLESGGGLVQPGGSLRLSCAASGGSLSNYVLGWFRQAPGKGREFVAAINWRDDITIGPPNVEGRFTISRDNAKNTLYLQMNSLRPEDTAVYYCGAGTPLNPGAYIYDWSYDYWGQGTLVTVSS |
| NC41v07 | 11 | EVQLLESGGGLVQPGGSLSISCAASGGSLSNYVLGWFRQAPGKGREFVAAINWRGDITIGPPNVEGRFTISRDNAKNTLYLQMNSLAPDDTAVYYCGAGTPLNPGAYIYDWSYDYWGQGTLVTVSS |
| NC41v08 | 12 | EVQLLESGGGLVQPGGSLSISCAASGGSLSNYVLGWFRQAPGKGREFVAAINWRGDITIGPPNVEGRFTISRDNAKNTLYLQMNSLRPEDTAVYYCGAGTPLNPGAYIYDWSYDYWGQGTLVTVSS |
| NC41v09 | 13 | EVQLLESGGGLVQPGGSLSISCAASGGSLSNYVLGWFRQAPGKGREFVAAINWRGDITIGPPNVEGRFTISRDNSKNTLYLQMNSLRPDDTAVYYCGAGTPLNPGAYIYDWSYDYWGQGTLVTVSS |
| NC41v10 | 14 | EVQLLESGGGLVQPGGSLSISCAASGGSLSNYVLGWFRQAPGKGREFVAAINWRGDITIGPPNVEGRFTISRDNAKNTGYLQMNSLAPDDTAVYYCGAGTPLNPGAYIYDWSYDYWGQGTLVTVSS |
| NC41v11 | 15 | EVQLLESGGGLVQAGGSLSISCAASGGSLSNYVLGWFRQAPGKGREFVAAINWRGDITIGPPNVEGRFTISRDNAKNTGYLQMNSLAPDDTAVYYCGAGTPLNPGAYIYDWSYDYWGQGTLVTVSS |
| NC41v12 | 16 | EVQLLESGGGLVQPGGSLSISCAASGGSLSNYVLGWFRQAPGKEREFVAAINWRGDITIGPPNVEGRFTISRDNAKNTGYLQMNSLAPDDTAVYYCGAGTPLNPGAYIYDWSYDYWGQGTLVTVSS |
| NC41v13 | 17 | EVQLLESGGGLVQPGGSLRLSCAASGGSLSNYVLGWFRQAPGKGREFVAAINWRGDITIGPPNVEGRFTISRDNAKNTGYLQMNSLAPEDTAVYYCGAGTPLNPGAYIYDWSYDYWGQGTLVTVSS |
| NC41v14 | 18 | EVQLLESGGGLVQPGGSLRLSCAASGGSLSNYVLGWFRQAPGKGREFVAAINWRGDITIGPPNVEGRFTISRDNSKNTLYLQMNSLAPEDTAVYYCGAGTPLNPGAYIYDWSYDYWGQGTLVTVSS |
| NC41v15 | 19 | EVQLLESGGGLVQAGGSLRLSCAASGGSLSNYVLGWFRQAPGKGREFVAAINWRGDITIGPPNVEGRFTISRDNAKNTLYLQMNSLAPEDTAVYYCGAGTPLNPGAYIYDWSYDYWGQGTLVTVSS |

TABLE A-2-continued

Amino acid sequences of anti-hRSV immunoglobulin single variable domains

| Nanobody® | SEQ ID NO: | Sequence |
|---|---|---|
| NC41v17 | 20 | EVQLLESGGGLVQPGGSLRLSCAASGGSLSNYVLGWFRQAPGKGREFVA AINWRGDITIGPPNVEGRFTISRDNSKNTLYLQMNSLRPEDTAVYYCGA GTPLNPGAYIYDWSYDYWGQGTLVTVSS |
| NC41v17 E1D | 21 | DVQLLESGGGLVQPGGSLRLSCAASGGSLSNYVLGWFRQAPGKGREFVA AINWRGDITIGPPNVEGRFTISRDNSKNTLYLQMNSLRPEDTAVYYCGA GTPLNPGAYIYDWSYDYWGQGTLVTVSS |
| NC41v18 | 22 | EVQLLESGGGLVQPGGSLRLSCAASGGSLSNYVLGWFRQAPGKGREFVA AINWRDDITIGPPNVEGRFTISRDNSKNTLYLQMNSLRPEDTAVYYCGA GTPLNPGAYIYDWSYDYWGQGTLVTVSS |
| NC41v18 E1D | 23 | DVQLLESGGGLVQPGGSLRLSCAASGGSLSNYVLGWFRQAPGKGREFVAA INWRDDITIGPPNVEGRFTISRDNSKNTLYLQMNSLRPEDTAVYYCGAGT PLNPGAYIYDWSYDYWGQGTLVTVSS |
| NC41v19 | 24 | EVQLVESGGGLVQPGGSLRLSCAASGGSLSNYVLGWFRQAPGKEREFVA AINWRGDITIGPPNVEGRFTISRDNAKNTGYLQMNSLAPDDTAVYYCGA GTPLNPGAYIYDWSYDYWGQGTLVTVSS |
| NC41v20 | 25 | EVQLVESGGGLVQPGGSLRLSCAASGGSLSNYVLGWFRQAPGKEREFVA AINWRGDITIGPPNVEGRFTISRDNAKNTGYLQMNSLRPDDTAVYYCGA GTPLNPGAYIYDWSYDYWGQGTLVTVSS |
| NC41v21 | 26 | EVQLVESGGGLVQPGGSLRLSCAASGGSLSNYVLGWFRQAPGKEREFVA AINWRGDITIGPPNVEGRFTISRDNAKNTGYLQMNSLAPEDTAVYYCGA GTPLNPGAYIYDWSYDYWGQGTLVTVSS |
| NC41v21 E1D | 27 | DVQLVESGGGLVQPGGSLRLSCAASGGSLSNYVLGWFRQAPGKEREFVA AINWRGDITIGPPNVEGRFTISRDNAKNTGYLQMNSLAPEDTAVYYCGA GTPLNPGAYIYDWSYDYWGQGTLVTVSS |
| NC41v22 | 28 | EVQLVESGGGLVQPGGSLRLSCAASGGSLSNYVLGWFRQAPGKEREFVA AINWRGDITIGPPNVEGRFTISRDNAKNTGYLQMNSLRPEDTAVYYCGA GTPLNPGAYIYDWSYDYWGQGTLVTVSS |
| NC41v22 E1D | 29 | DVQLVESGGGLVQPGGSLRLSCAASGGSLSNYVLGWFRQAPGKEREFVA AINWRGDITIGPPNVEGRFTISRDNAKNTGYLQMNSLRPEDTAVYYCGA GTPLNPGAYIYDWSYDYWGQGTLVTVSS |
| NC41v23 | 30 | EVQLVESGGGLVQPGGSLRLSCAASGGSLSNYVLGWFRQAPGKEREFVA AINWRGDITIGPPNVEGRFTISRDNAKNTGYLQMNSLAPDDTAVYYCGA GTPLNPGAYIYDWSYDYWGRGTLVTVSS |
| NC41v24 | 31 | EVQLVESGGGLVQPGGSLRLSCAASGGSLSNYVLGWFRQAPGKEREFVA AINWRGDITIGPPNVEGRFTISRDNAKNTGYLQMNSLRPDDTAVYYCGA GTPLNPGAYIYDWSYDYWGRGTLVTVSS |
| NC41v25 | 32 | EVQLVESGGGLVQPGGSLRLSCAASGGSLSNYVLGWFRQAPGKEREFVA AINWRGDITIGPPNVEGRFTISRDNAKNTGYLQMNSLAPEDTAVYYCGA GTPLNPGAYIYDWSYDYWGRGTLVTVSS |
| NC41v26 | 33 | EVQLVESGGGLVQPGGSLRLSCAASGGSLSNYVLGWFRQAPGKEREFVA AINWRGDITIGPPNVEGRFTISRDNAKNTGYLQMNSLRPEDTAVYYCGA GTPLNPGAYIYDWSYDYWGRGTLVTVSS |
| NC41v26 E1D | 34 | DVQLVESGGGLVQPGGSLRLSCAASGGSLSNYVLGWFRQAPGKEREFVA AINWRGDITIGPPNVEGRFTISRDNAKNTGYLQMNSLRPEDTAVYYCGA GTPLNPGAYIYDWSYDYWGRGTLVTVSS |

TABLE A-3

Amino acid sequences of preferred polypeptides of the invention

| Nanobody | SEQ ID NO: | Sequence |
|---|---|---|
| RSV407 | 65 | EVQLVESGGGLVQAGGSLSISCAASGGSLSNYVLGWFRQAPGKEREFVAAI NWRGDITIGPPNVEGRFTISRDNAKNTGYLQMNSLAPDDTAVYYCGAGTPL NPGAYIYDWSYDYWGRGTQVTVSSGGGGSGGGGSGGGGSEVQLVESGGGLV QAGGSLSISCAASGGSLSNYVLGWFRQAPGKEREFVAAINWRGDITIGPPN VEGRFTISRDNAKNTGYLQMNSLAPDDDTAVYYCGAGTPLNPGAYIYDWSYD YWGRGTQVTVSSGGGGSGGGGSGGGGSEVQLVESGGGLVQAGGSLSISCAA SGGSLSNYVLGWFRQAPGKEREFVAAINWRGDITIGPPNVEGRFTISRDNA KNTGYLQMNSLAPDDTAVYYCGAGTPLNPGAYIYDWSYDYWGRGTQVTVSS |

TABLE A-3-continued

Amino acid sequences of preferred polypeptides of the invention

| Nanobody | SEQ ID NO: | Sequence |
|---|---|---|
| RSV408 | 66 | EVQLVESGGGLVQAGGSLSISCAASGGSLSNYVLGWFRQAPGKEREFVAAI<br>NWRGDITIGPPNVEGRFTISRDNAKNTYLQMNSLAPDDTAVYYCGAGTPL<br>NPGAYIYDWSYDYWGRGTQVTVSSAAAEVQLVESGGGLVQAGGSLSISCAA<br>SGGSLSNYVLGWFRQAPGKEREFVAAINWRGDITIGPPNVEGRFTISRDNA<br>KNTGYLQMNSLAPDDTAVYYCGAGTPLNPGAYIYDWSYDYWGRGTQVTVSS<br>AAAEVQLVESGGGLVQAGGSLSISCAASGGSLSNYVLGWFRQAPGKEREFV<br>AAINWRGDITIGPPNVEGRFTISRDNAKNTGYLQMNSLAPDDTAVYYCGAG<br>TPLNPGAYIYDWSYDYWGRGTQVTVSS |
| RSV409 | 67 | EVQLVESGGGLVQAGGSLSISCAASGGSLSNYVLGWFRQAPGKEREFVAAI<br>NWRGDITIGPPNVEGRFTISRDNAKNTGYLQMNSLAPDDTAVYYCGAGTPL<br>NPGAYIYDWSYDYWGRGTQVTVSSGGGGSGGGGSEVQLVESGGGLVQAGGSL<br>SISCAASGGSLSNYVLGWFRQAPGKEREFVAAINWRGDITIGPPNVEGRFT<br>ISRDNAKNTGYLQMNSLAPDDTAVYYCGAGTPLNPGAYIYDWSYDYWGRGT<br>QVTVSSGGGGSGGGGSEVQLVESGGGLVQAGGSLSISCAASGGSLSNYVLGW<br>FRQAPGKEREFVAAINWRGDITIGPPNVEGRFTISRDNAKNTGYLQMNSLA<br>PDDTAVYYCGAGTPLNPGAYIYDWSYDYWGRGTQVTVSS |
| RSV410 | 68 | EVQLVESGGGLVQAGGSLSISCAASGGSLSNYVLGWFRQAPGKEREFVAAI<br>NWRGDITIGPPNVEGRFTISRDNAKNTGYLQMNSLAPDDTAVYYCGAGTPL<br>NPGAYIYDWSYDYWGRGTQVTVSSGGGGSGGGGSGGGGSGGGGSEVQLVES<br>GGGLVQAGGSLSISCAASGGSLSNYVLGWFRQAPGKEREFVAAINWRGDIT<br>IGPPNVEGRFTISRDNAKNTGYLQMNSLAPDDTAVYYCGAGTPLNPGAYIY<br>DWSYDYWGRGTQVTVSSGGGGSGGGGSGGGGSGGGGSEVQLVESGGGLVQA<br>GGSLSISCAASGGSLSNYVLGWFRQAPGKEREFVAAINWRGDITIGPPNVE<br>GRFTISRDNAKNTGYLQMNSLAPDDTAVYYCGAGTPLNPGAYIYDWSYDYW<br>GRGTQVTVSS |
| RSV411 | 69 | EVQLVESGGGLVQAGGSLSISCAASGGSLSNYVLGWFRQAPGKEREFVAAI<br>NWRGDITIGPPNVEGRFTISRDNAKNTGYLQMNSLAPDDTAVYYCGAGTPL<br>NPGAYIYDWSYDYWGRGTQVTVSSGGGGSGGGGSGGGGSEVQLVESGGGLV<br>QAGGSLSISCAASGGSLSNYVLGWFRQAPGKEREFVAAINWRGDITIGPPN<br>VEGRFTISRDNAKNTGYLQMNSLAPDDTAVYYCGAGTPLNPGAYIYDWSYD<br>YWGRGTQVTVSSGGGGSGGGGSGGGGSEVQLVESGGGLVQPGGSLRLSCAA<br>SGLTLDYYALGWFRQAPGKEREGVSCISSSDHSTTYTDSVKGRFTISWDNA<br>KNTLYLQMNSLKPGDTAVYYCAADPALGCYSGSYYPRYDYWGQGTQVTVSS |
| RSV413 | 70 | EVQLVESGGGLVQAGGSLSISCAASGGSLSNYVLGWFRQAPGKEREFVAAI<br>NWRGDITIGPPNVEGRFTISRDNAKNTGYLQMNSLAPDDTAVYYCGAGTPL<br>NPGAYIYDWSYDYWGRGTQVTVSSGGGGSGGGGSGGGGSEVQLVESGGGLV<br>QPGGSLRLSCAASGLTLDYYALGWFRQAPGKEREGVSCISSSDHSTTYTDS<br>VKGRFTISWDNAKNTLYLQMNSLKPGDTAVYYCAADPALGCYSGSYYPRYD<br>YWGQGTQVTVSSGGGGSGGGGSGGGGSEVQLVESGGGLVQAGGSLSISCAA<br>SGGSLSNYVLGWFRQAPGKEREFVAAINWRGDITIGPPNVEGRFTISRDNA<br>KNTGYLQMNSLAPDDTAVYYCGAGTPLNPGAYIYDWSYDYWGRGTQVTVSS |
| RSV434 | 71 | DVQLVESGGGLVQAGGSLSISCAASGGSLSNYVLGWFRQAPGKEREFVAAI<br>NWRGDITIGPPNVEGRFTISRDNAKNTGYLQMNSLAPDDTAVYYCGAGTPL<br>NPGAYIYDWSYDYWGRGTQVTVSSGGGGSGGGGSGGGGSEVQLVESGGGLV<br>QAGGSLSISCAASGGSLSNYVLGWFRQAPGKEREFVAAINWRGDITIGPPN<br>VEGRFTISRDNAKNTGYLQMNSLAPDDTAVYYCGAGTPLNPGAYIYDWSYD<br>YWGRGTQVTVSSGGGGSGGGGSGGGGSEVQLVESGGGLVQAGGSLSISCAA<br>SGGSLSNYVLGWFRQAPGKEREFVAAINWRGDITIGPPNVEGRFTISRDNA<br>KNTGYLQMNSLAPDDTAVYYCGAGTPLNPGAYIYDWSYDYWGRGTQVTVSS |
| RSV414 V03 | 72 | EVQLLESGGGLVQPGGSLRISCAASGGSLSNYVLGWFRQAPGKGREFVAAI<br>NWRGDITIGPPNVEGRFTISRDNSKNTLYLQMNSLRPEDTAVYYCGAGTPL<br>NPGAYIYDWSYDYWGQGTLVTVSSGGGGSGGGGSGGGGSEVQLLESGGGLV<br>QPGGSLRISCAASGGSLSNYVLGWFRQAPGKGREFVAAINWRGDITIGPPN<br>VEGRFTISRDNSKNTLYLQMNSLRPEDTAVYYCGAGTPLNPGAYIYDWSYD<br>YWGQGTLVTVSSGGGGSGGGGSGGGGSEVQLLESGGGLVQPGGSLRISCAA<br>SGGSLSNYVLGWFRQAPGKGREFVAAINWRGDITIGPPNVEGRFTISRDNS<br>KNTLYLQMNSLRPEDTAVYYCGAGTPLNPGAYIYDWSYDYWGQGTLVTVSS |
| RSV443 V3D | 73 | DVQLLESGGGLVQPGGSLRISCAASGGSLSNYVLGWFRQAPGKGREFVAAI<br>NWRGDITIGPPNVEGRFTISRDNSKNTLYLQMNSLRPEDTAVYYCGAGTPL<br>NPGAYIYDWSYDYWGQGTLVTVSSGGGGSGGGGSGGGGSEVQLLESGGGLV<br>QPGGSLRISCAASGGSLSNYVLGWFRQAPGKGREFVAAINWRGDITIGPPN<br>VEGRFTISRDNSKNTLYLQMNSLRPEDTAVYYCGAGTPLNPGAYIYDWSYD<br>YWGQGTLVTVSSGGGGSGGGGSGGGGSEVQLLESGGGLVQPGGSLRISCAA<br>SGGSLSNYVLGWFRQAPGKGREFVAAINWRGDITIGPPNVEGRFTISRDNS<br>KNTLYLQMNSLRPEDTAVYYCGAGTPLNPGAYIYDWSYDYWGQGTLVTVSS |

TABLE A-3-continued

Amino acid sequences of preferred polypeptides of the invention

| Nanobody | SEQ ID NO: | Sequence |
|---|---|---|
| RSV426 V06 | 74 | EVQLLESGGGLVQPGGSLRLSCAASGGSLSNYVLGWFRQAPGKGREFVAAI NWRDDITIGPPNVEGRFTISRDNAKNTLYLQMNSLRPEDTAVYYCGAGTPL NPGAYIYDWSYDYWGQGTLVTVSSGGGGSGGGGSGGGGSEVQLLESGGGLV QPGGSLRLSCAASGGSLSNYVLGWFRQAPGKGREFVAAINWRDDITIGPPN VEGRFTISRDNAKNTLYLQMNSLRPEDTAVYYCGAGTPLNPGAYIYDWSYD YWGQGTLVTVSSGGGGSGGGGSGGGGSEVQLLESGGGLVQPGGSLRLSCAA SGGSLSNYVLGWFRQAPGKGREFVAAINWRDDITIGPPNVEGRFTISRDNA KNTLYLQMNSLRPEDTAVYYCGAGTPLNPGAYIYDWSYDYWGQGTLVTVSS |
| RSV444 V6D | 75 | DVQLLESGGGLVQPGGSLRLSCAASGGSLSNYVLGWFRQAPGKGREFVAAI NWRDDITIGPPNVEGRFTISRDNAKNTLYLQMNSLRPEDTAVYYCGAGTPL NPGAYIYDWSYDYWGQGTLVTVSSGGGGSGGGGSGGGGSEVQLLESGGGLV QPGGSLRLSCAASGGSLSNYVLGWFRQAPGKGREFVAAINWRDDITIGPPN VEGRFTISRDNAKNTLYLQMNSLRPEDTAVYYCGAGTPLNPGAYIYDWSYD YWGQGTLVTVSSGGGGSGGGGSGGGGSEVQLLESGGGLVQPGGSLRLSCAA SGGSLSNYVLGWFRQAPGKGREFVAAINWRDDITIGPPNVEGRFTISRDNA KNTLYLQMNSLRPEDTAVYYCGAGTPLNPGAYIYDWSYDYWGQGTLVTVSS |
| RSV442 V17 | 76 | EVQLLESGGGLVQPGGSLRLSCAASGGSLSNYVLGWFRQAPGKGREFVAAI NWRGDITIGPPNVEGRFTISRDNSKNTLYLQMNSLRPEDTAVYYCGAGTPL NPGAYIYDWSYDYWGQGTLVTVSSGGGGSGGGGSGGGGSEVQLLESGGGLV QPGGSLRLSCAASGGSLSNYVLGWFRQAPGKGREFVAAINWRGDITIGPPN VEGRFTISRDNSKNTLYLQMNSLRPEDTAVYYCGAGTPLNPGAYIYDWSYD YWGQGTLVTVSSGGGGSGGGGSGGGGSEVQLLESGGGLVQPGGSLRLSCAA SGGSLSNYVLGWFRQAPGKGREFVAAINWRGDITIGPPNVEGRFTISRDNS KNTLYLQMNSLRPEDTAVYYCGAGTPLNPGAYIYDWSYDYWGQGTLVTVSS |
| RSV435 V17D | 77 | DVQLLESGGGLVQPGGSLRLSCAASGGSLSNYVLGWFRQAPGKGREFVAAI NWRGDITIGPPNVEGRFTISRDNSKNTLYLQMNSLRPEDTAVYYCGAGTPL NPGAYIYDWSYDYWGQGTLVTVSSGGGGSGGGGSGGGGSEVQLLESGGGLV QPGGSLRLSCAASGGSLSNYVLGWFRQAPGKGREFVAAINWRGDITIGPPN VEGRFTISRDNSKNTLYLQMNSLRPEDTAVYYCGAGTPLNPGAYIYDWSYD YWGQGTLVTVSSGGGGSGGGGSGGGGSEVQLLESGGGLVQPGGSLRLSCAA SGGSLSNYVLGWFRQAPGKGREFVAAINWRGDITIGPPNVEGRFTISRDNS KNTLYLQMNSLRPEDTAVYYCGAGTPLNPGAYIYDWSYDYWGQGTLVTVSS |
| RSV427 V18 | 78 | EVQLLESGGGLVQPGGSLRLSCAASGGSLSNYVLGWFRQAPGKGREFVAAI NWRDDITIGPPNVEGRFTISRDNSKNTLYLQMNSLRPEDTAVYYCGAGTPL NPGAYIYDWSYDYWGQGTLVTVSSGGGGSGGGGSGGGGSEVQLLESGGGLV QPGGSLRLSCAASGGSLSNYVLGWFRQAPGKGREFVAAINWRDDITIGPPN VEGRFTISRDNSKNTLYLQMNSLRPEDTAVYYCGAGTPLNPGAYIYDWSYD YWGQGTLVTVSSGGGGSGGGGSGGGGSEVQLLESGGGLVQPGGSLRLSCAA SGGSLSNYVLGWFRQAPGKGREFVAAINWRDDITIGPPNVEGRFTISRDNS KNTLYLQMNSLRPEDTAVYYCGAGTPLNPGAYIYDWSYDYWGQGTLVTVSS |
| RSV445 V18D | 79 | DVQLLESGGGLVQPGGSLRLSCAASGGSLSNYVLGWFRQAPGKGREFVAAI NWRDDITIGPPNVEGRFTISRDNSKNTLYLQMNSLRPEDTAVYYCGAGTPL NPGAYIYDWSYDYWGQGTLVTVSSGGGGSGGGGSGGGGSEVQLLESGGGLV QPGGSLRLSCAASGGSLSNYVLGWFRQAPGKEREFVAAINWRDDITIGPPN VEGRFTISRDNSKNTLYLQMNSLRPEDTAVYYCGAGTPLNPGAYIYDWSYD YWGQGTLVTVSSGGGGSGGGGSGGGGSEVQLLESGGGLVQPGGSLRLSCAA SGGSLSNYVLGWFRQAPGKGREFVAAINWRDDITIGPPNVEGRFTISRDNS KNTLYLQMNSLRPEDTAVYYCGAGTPLNPGAYIYDWSYDYWGQGTLVTVSS |
| RSV436 V20 | 80 | EVQLVESGGGLVQPGGSLRLSCAASGGSLSNYVLGWFRQAPGKEREFVAAI NWRGDITIGPPNVEGRFTISRDNAKNTYLQMNSLRPDDTAVYYCGAGTPL NPGAYIYDWSYDYWGQGTLVTVSSGGGGSGGGGSGGGGSEVQLVESGGGLV QPGGSLRLSCAASGGSLSNYVLGWFRQAPGKEREFVAAINWRGDITIGPPN VEGRFTISRDNAKNTYLQMNSLRPDDTAVYYCGAGTPLNPGAYIYDWSYD YWGQGTLVTVSSGGGGSGGGGSGGGGSEVQLVESGGGLVQPGGSLRLSCAA SGGSLSNYVLGWFRQAPGKEREFVAAINWRGDITIGPPNVEGRFTISRDNA |
| RSV437 V20D | 81 | DVQLVESGGGLVQPGGSLRLSCAASGGSLSNYVLGWFRQAPGKEREFVAAI NWRGDITIGPPNVEGRFTISRDNAKNTYLQMNSLRPDDTAVYYCGAGTPL NPGAYIYDWSYDYWGQGTLVTVSSGGGGSGGGGSGGGGSEVQLVESGGGLV QPGGSLRLSCAASGGSLSNYVLGWFRQAPGKEREFVAAINWRGDITIGPPN VEGRFTISRDNAKNTYLQMNSLRPDDTAVYYCGAGTPLNPGAYIYDWSYD YWGQGTLVTVSSGGGGSGGGGSGGGGSEVQLVESGGGLVQPGGSLRLSCAA SGGSLSNYVLGWFRQAPGKEREFVAAINWRGDITIGPPNVEGRFTISRDNA |

TABLE A-3-continued

Amino acid sequences of preferred polypeptides of the invention

| Nanobody | SEQ ID NO: | Sequence |
|---|---|---|
| RSV438 V22 | 82 | EVQLVESGGGLVQPGGSLRLSCAASGGSLSNYVLGWFRQAPGKEREFVAAI NWRGDITIGPPNVEGRFTISRDNAKNTYLQMNSLRPEDTAVYYCGAGTPL NPGAYIYDWSYDYWGQGTLVTVSSGGGGSGGGGSGGGGSEVQLVESGGGLV QPGGSLRLSCAASGGSLSNYVLGWFRQAPGKEREFVAAINWRGDITIGPPN VEGRFTISRDNAKNTYLQMNSLRPEDTAVYYCGAGTPLNPGAYIYDWSYD YWGQGTLVTVSSGGGGSGGGGSGGGGSEVQLVESGGGLVQPGGSLRLSCAA SGGSLSNYVLGWFRQAPGKEREFVAAINWRGDITIGPPNVEGRFTISRDNA KNTYLQMNSLRPEDTAVYYCGAGTPLNPGAYIYDWSYDYWGQGTLVTVSS |
| RSV439 V26 | 83 | EVQLVESGGGLVQPGGSLRLSCAASGGSLSNYVLGWFRQAPGKEREFVAAI NWRGDITIGPPNVEGRFTISRDNAKNTYLQMNSLRPEDTAVYYCGAGTPL NPGAYIYDWSYDYWGRGTLVTVSSGGGGSGGGGSGGGGSEVQLVESGGGLV QPGGSLRLSCAASGGSLSNYVLGWFRQAPGKEREFVAAINWRGDITIGPPN VEGRFTISRDNAKNTYLQMNSLRPEDTAVYYCGAGTPLNPGAYIYDWSYD YWGRGTLVTVSSGGGGSGGGGSGGGGSEVQLVESGGGLVQPGGSLRLSCAA SGGSLSNYVLGWFRQAPGKEREFVAAINWRGDITIGPPNVEGRFTISRDNA KNTYLQMNSLRPEDTAVYYCGAGTPLNPGAYIYDWSYDYWGRGTLVTVSS |
| RSV440 V26D | 84 | DVQLVESGGGLVQPGGSLRLSCAASGGSLSNYVLGWFRQAPGKEREFVAAI NWRGDITIGPPNVEGRFTISRDNAKNTYLQMNSLRPEDTAVYYCGAGTPL NPGAYIYDWSYDYWGRGTLVTVSSGGGGSGGGGSGGGGSEVQLVESGGGLV QPGGSLRLSCAASGGSLSNYVLGWFRQAPGKEREFVAAINWRGDITIGPPN VEGRFTISRDNAKNTYLQMNSLRPEDTAVYYCGAGTPLNPGAYIYDWSYD YWGRGTLVTVSSGGGGSGGGGSGGGGSEVQLVESGGGLVQPGGSLRLSCAA SGGSLSNYVLGWFRQAPGKEREFVAAINWRGDITIGPPNVEGRFTISRDNA KNTYLQMNSLRPEDTAVYYCGAGTPLNPGAYIYDWSYDYWGRGTLVTVSS |
| RSV441 V22D | 85 | DVQLVESGGGLVQPGGSLRLSCAASGGSLSNYVLGWFRQAPGKEREFVAAI NWRGDITIGPPNVEGRFTISRDNAKNTYLQMNSLRPEDTAVYYCGAGTPL NPGAYIYDWSYDYWGQGTLVTVSSGGGGSGGGGSGGGGSEVQLVESGGGLV QPGGSLRLSCAASGGSLSNYVLGWFRQAPGKEREFVAAINWRGDITIGPPN VEGRFTISRDNAKNTYLQMNSLRPEDTAVYYCGAGTPLNPGAYIYDWSYD YWGQGTLVTVSSGGGGSGGGGSGGGGSEVQLVESGGGLVQPGGSLRLSCAA SGGSLSNYVLGWFRQAPGKEREFVAAINWRGDITIGPPNVEGRFTISRDNA KNTYLQMNSLRPEDTAVYYCGAGTPLNPGAYIYDWSYDYWGQGTLVTVSS |

TABLE A-4

Amino acid sequences of linkers

| Linker | SEQ ID NO: | Sequences |
|---|---|---|
| 5GS | 86 | GGGGS |
| 7GS | 87 | SGGSGGS |
| GS8 | 88 | GGGGSGGS |
| 9GS | 89 | GGGGSGGGS |
| 10GS | 90 | GGGGSGGGGS |
| 15GS | 91 | GGGGSGGGGSGGGGS |
| 18GS | 92 | GGGGSGGGGSGGGGGGS |
| 20GS | 93 | GGGGSGGGGSGGGGSGGGGS |
| 25GS | 94 | GGGGSGGGGSGGGGSGGGGSGGGGS |
| 30GS | 95 | GGGGSGGGGSGGGGSGGGGSGGGGSGGGGS |
| 35GS | 96 | GGGGSGGGGSGGGGSGGGGSGGGGSGGGGSGGGGS |
| G1 hinge | 97 | EPKSCDKTHTCPPCP |
| 9GS-G1 hinge | 98 | GGGGSGGGSEPKSCDKTHTCPPCP |
| Llama upper long hinge region | 99 | EPKTPKPQPAAA |
| G3 hinge | 100 | ELKTPLGDTTHTCPRCPEPKSCDTPPPCPRCPE PKSCDTPPPCPRCPEPKSCDTPPPCPRCP |
| Ala | 101 | AAA |

The invention claimed is:

1. An inhalation device for delivering a nebulized aerosol to a patient, the inhalation device comprising:
   (a) an aerosol generator with a vibratable mesh;
   (b) a reservoir for a liquid to be nebulised, said reservoir being in fluid connection with the vibratable mesh;
   (c) a gas inlet opening shaped as a tube fitting;
   (d) a face mask, comprising:
      (i) a casing,
      (ii) an aerosol inlet opening,
      (iii) a patient contacting surface, and
      (iv) a one-way exhalation valve or a two-way inhalation/exhalation valve in the casing having an exhalation overpressure resistance selected in the range from 0.5 to 5 mbar; and
   (e) a flow channel extending from the gas inlet opening to the aerosol inlet opening of the face mask, the flow channel having:
      (v) a lateral opening through which the aerosol generator is at least partially inserted into the flow channel
   wherein the inhalation device does not comprise a variable flow restrictor which is configured to restrict an inspiratory flow between the gas inlet opening and the aerosol inlet opening of the face mask at a flow rate of 1 to 20 L/min, and
   wherein the flow channel does not comprise a further inlet opening for receiving a gas.

2. The inhalation device of claim 1, wherein the flow channel is sized and shaped to achieve, at a position immediately proximate to the lateral opening between the lateral opening and the gas inlet opening, an average gas velocity of at least 4 m/s at a flow rate of 2 L/min.

3. The inhalation device of claim 1, wherein the aerosol generator is oriented to emit nebulised aerosol into the flow channel at an angle of approximately 90° to a longitudinal axis of the flow channel, and wherein the inhalation device comprises a switch for starting and stopping the operation of the aerosol generator, wherein the operation of the aerosol generator comprises continuous vibration of the vibratable mesh.

4. The inhalation device of claim 1, wherein the face mask has a nominal internal volume of not more than 90 mL.

5. The inhalation device of claim 1, wherein the face mask comprises the two-way inhalation/exhalation valve, wherein the two-way inhalation exhalation valve has a resistance of not more than 3 mbar in either direction, and wherein a nominal internal volume of the face mask is not more than about 50 mL.

6. The inhalation device of claim 1, wherein an interior volume of the flow channel between the lateral opening and the aerosol inlet opening of the face mask is not more than 30 mL.

7. The inhalation device of claim 1, further comprising a flow restrictor capable of restricting the flow of gas through the flow channel to a constant flow rate in the range from 1 to 5 L/min when connecting the gas inlet opening with a pressurised gas source.

8. The inhalation device of claim 1, further comprising:
(f) a base unit, comprising:
(vi) an electronic controller configured to control the aerosol generator,
wherein an upstream portion of the flow channel comprises the gas inlet opening; and
(g) a mixing channel unit, comprising:
(vii) a downstream portion of the flow channel comprising the lateral opening, wherein the downstream portion comprises a segment where the flow channel widens in a direction from the lateral opening to the aerosol inlet opening of the face mask.

9. The inhalation device of claim 1, wherein a portion of the flow channel between the lateral opening and the gas inlet opening is shaped such as to effect a laminar flow when a gas is conducted through the flow channel at a flow rate from 1 to 20 L/min.

10. An assembly comprising the inhalation device of claim 1 and a gas source configured to provide a gas at a constant flow rate in the range from 1 to 5 L/min, wherein the gas source is connected to the inhalation device such that the gas enters the flow channel through the gas inlet opening, and wherein the gas source is configured to provide a gas selected from oxygen, air, oxygen-enriched air, a mixture of oxygen and nitrogen, and a mixture of helium and oxygen.

11. A combination or kit comprising (a) the inhalation device of claim 1 or the assembly of claim 10, and (b) a pharmaceutical composition for inhalational use.

12. The combination or kit of claim 11, wherein the pharmaceutical composition comprises an active agent selected from antibiotics, antiviral agents, bronchodilators, anticholinergics, corticosteroids, hypertonic saline, antibodies, antibody fragments, and immunoglobin single variable domains.

13. The combination or kit of claim 12, wherein the active agent is an anti-RSV agent, and wherein the anti-RSV agent is a polypeptide comprising one or more anti-RSV immunoglobin single variable domains.

14. The combination or kit of claim 13, wherein:
(a) at least one of the one or more anti-RSV immunoglobin single variable domains comprises a CDR1 having the amino acid sequence of SEQ ID NO: 46, a CDR2 having the amino acid sequence of one of SEQ ID NOs: 49-50, and a CDR3 having the amino acid sequence of SEQ ID NO: 61;
(b) at least one of the one or more anti-RSV immunoglobin single variable domains is selected from one of the amino acid sequences of SEQ ID Nos: 1-34; or
(c) the polypeptide is selected from one of the amino acid sequences of SEQ ID NOs: 65-85.

15. The combination or kit of claim 13, further comprising a bronchodilator, wherein the bronchodilator is selected from the group consisting of beta2-mimetics and anticholinergics.

16. The combination or kit of claim 12, wherein the active agent is an anti-RSV agent, and wherein the anti-RSV agent is a polypeptide consisting essentially of one or more anti-RSV immunoglobin single variable domains.

17. A method of delivering a nebulised aerosol to a patient, comprising the steps of:
(a) providing the inhalation device of claim 1;
(b) providing a gas source;
(c) connecting the gas source to the inhalation device;
(d) placing a nebuliser solution in the reservoir;
(e) allowing gas to enter the inhalation device from the gas source such that the gas enters the flow channel through the gas inlet opening at a constant flow rate in the range from 1 to 5 L/min and vibrating the vibratable mesh to form a nebulised aerosol; and
(f) administering the nebulised aerosol to the patient via the inhalation device.

18. A method for treating a patient suffering from a disease affecting the respiratory system, comprising:
administering to the patient a nebulised aerosol suitable to treat the disease using the inhalation device of claim 1, the assembly of claim 10, or the combination or kit of claim 11.

19. The method of claim 18, wherein the patient is:
(a) a paediatric patient; or
(b) an adult patient for whom controlled oral inhalation is not possible or considerably impeded.

20. The method of claim 19, wherein the paediatric patient is selected from the group consisting of a neonate, an infant, a toddler, and a school child.

21. The method of claim 18, wherein the disease affecting the respiratory system is an RSV infection.

22. The method of claim 18, wherein the disease affecting the respiratory system is an RSV lower respiratory tract infection.

* * * * *

SEQUENCE LISTING

<160> NUMBER OF SEQ ID NOS: 101

<210> SEQ ID NO 1
<211> LENGTH: 126
<212> TYPE: PRT
<213> ORGANISM: Artificial Sequence
<220> FEATURE:
<223> OTHER INFORMATION: Nanobody sequence

<400> SEQUENCE: 1

Glu Val Gln Leu Val Glu Ser Gly Gly Gly Leu Val Gln Ala Gly Gly
1               5                   10                  15

Ser Leu Ser Ile Ser Cys Ala Ala Ser Gly Gly Ser Leu Ser Asn Tyr
            20                  25                  30

Val Leu Gly Trp Phe Arg Gln Ala Pro Gly Lys Glu Arg Glu Phe Val
        35                  40                  45

Ala Ala Ile Asn Trp Arg Gly Asp Ile Thr Ile Gly Pro Pro Asn Val
    50                  55                  60

Glu Gly Arg Phe Thr Ile Ser Arg Asp Asn Ala Lys Asn Thr Gly Tyr
65                  70                  75                  80

Leu Gln Met Asn Ser Leu Ala Pro Asp Asp Thr Ala Val Tyr Tyr Cys
                85                  90                  95

Gly Ala Gly Thr Pro Leu Asn Pro Gly Ala Tyr Ile Tyr Asp Trp Ser
            100                 105                 110

Tyr Asp Tyr Trp Gly Arg Gly Thr Gln Val Thr Val Ser Ser
        115                 120                 125

<210> SEQ ID NO 2
<211> LENGTH: 126
<212> TYPE: PRT
<213> ORGANISM: Artificial Sequence
<220> FEATURE:
<223> OTHER INFORMATION: Nanobody sequence

<400> SEQUENCE: 2

Asp Val Gln Leu Val Glu Ser Gly Gly Gly Leu Val Gln Ala Gly Gly
1               5                   10                  15

Ser Leu Ser Ile Ser Cys Ala Ala Ser Gly Gly Ser Leu Ser Asn Tyr
            20                  25                  30

Val Leu Gly Trp Phe Arg Gln Ala Pro Gly Lys Glu Arg Glu Phe Val
        35                  40                  45

Ala Ala Ile Asn Trp Arg Gly Asp Ile Thr Ile Gly Pro Pro Asn Val
    50                  55                  60

Glu Gly Arg Phe Thr Ile Ser Arg Asp Asn Ala Lys Asn Thr Gly Tyr
65                  70                  75                  80

Leu Gln Met Asn Ser Leu Ala Pro Asp Asp Thr Ala Val Tyr Tyr Cys
                85                  90                  95

Gly Ala Gly Thr Pro Leu Asn Pro Gly Ala Tyr Ile Tyr Asp Trp Ser
            100                 105                 110

Tyr Asp Tyr Trp Gly Arg Gly Thr Gln Val Thr Val Ser Ser
        115                 120                 125

<210> SEQ ID NO 3
<211> LENGTH: 126
<212> TYPE: PRT
<213> ORGANISM: Artificial Sequence
<220> FEATURE:
<223> OTHER INFORMATION: Nanobody sequence

<400> SEQUENCE: 3

Glu Val Gln Leu Leu Glu Ser Gly Gly Gly Leu Val Gln Pro Gly Gly
1               5                   10                  15

Ser Leu Arg Leu Ser Cys Ala Ser Gly Gly Ser Leu Ser Asn Tyr
            20                  25                  30

Val Leu Gly Trp Phe Arg Gln Ala Pro Gly Lys Gly Arg Glu Phe Val
            35                  40                  45

Ala Ala Ile Asn Trp Arg Gly Asp Ile Thr Ile Gly Pro Pro Asn Val
 50                  55                  60

Glu Gly Arg Phe Thr Ile Ser Arg Asp Asn Ala Lys Asn Thr Leu Tyr
 65                  70                  75                  80

Leu Gln Met Asn Ser Leu Ala Pro Glu Asp Thr Ala Val Tyr Tyr Cys
                 85                  90                  95

Gly Ala Gly Thr Pro Leu Asn Pro Gly Ala Tyr Ile Tyr Asp Trp Ser
            100                 105                 110

Tyr Asp Tyr Trp Gly Gln Gly Thr Leu Val Thr Val Ser Ser
            115                 120                 125

<210> SEQ ID NO 4
<211> LENGTH: 126
<212> TYPE: PRT
<213> ORGANISM: Artificial Sequence
<220> FEATURE:
<223> OTHER INFORMATION: Nanobody sequence

<400> SEQUENCE: 4

Glu Val Gln Leu Leu Glu Ser Gly Gly Gly Leu Val Gln Pro Gly Gly
 1               5                  10                  15

Ser Leu Arg Ile Ser Cys Ala Ala Ser Gly Gly Ser Leu Ser Asn Tyr
            20                  25                  30

Val Leu Gly Trp Phe Arg Gln Ala Pro Gly Lys Gly Arg Glu Phe Val
            35                  40                  45

Ala Ala Ile Asn Trp Arg Gly Asp Ile Thr Ile Gly Pro Pro Asn Val
 50                  55                  60

Glu Gly Arg Phe Thr Ile Ser Arg Asp Asn Ser Lys Asn Thr Leu Tyr
 65                  70                  75                  80

Leu Gln Met Asn Ser Leu Ala Pro Glu Asp Thr Ala Val Tyr Tyr Cys
                 85                  90                  95

Gly Ala Gly Thr Pro Leu Asn Pro Gly Ala Tyr Ile Tyr Asp Trp Ser
            100                 105                 110

Tyr Asp Tyr Trp Gly Gln Gly Thr Leu Val Thr Val Ser Ser
            115                 120                 125

<210> SEQ ID NO 5
<211> LENGTH: 126
<212> TYPE: PRT
<213> ORGANISM: Artificial Sequence
<220> FEATURE:
<223> OTHER INFORMATION: Nanobody sequence

<400> SEQUENCE: 5

Glu Val Gln Leu Leu Glu Ser Gly Gly Gly Leu Val Gln Pro Gly Gly
 1               5                  10                  15

Ser Leu Arg Ile Ser Cys Ala Ala Ser Gly Gly Ser Leu Ser Asn Tyr
            20                  25                  30

Val Leu Gly Trp Phe Arg Gln Ala Pro Gly Lys Gly Arg Glu Phe Val
            35                  40                  45

Ala Ala Ile Asn Trp Arg Gly Asp Ile Thr Ile Gly Pro Pro Asn Val
 50                  55                  60

Glu Gly Arg Phe Thr Ile Ser Arg Asp Asn Ser Lys Asn Thr Leu Tyr
 65                  70                  75                  80

Leu Gln Met Asn Ser Leu Arg Pro Glu Asp Thr Ala Val Tyr Tyr Cys
                 85                  90                  95

Gly Ala Gly Thr Pro Leu Asn Pro Gly Ala Tyr Ile Tyr Asp Trp Ser
            100                 105                 110

Tyr Asp Tyr Trp Gly Gln Gly Thr Leu Val Thr Val Ser Ser
            115                 120                 125

<210> SEQ ID NO 6
<211> LENGTH: 126
<212> TYPE: PRT
<213> ORGANISM: Artificial Sequence
<220> FEATURE:
<223> OTHER INFORMATION: Nanobody sequence

<400> SEQUENCE: 6

Asp Val Gln Leu Leu Glu Ser Gly Gly Gly Leu Val Gln Pro Gly Gly
1               5                   10                  15

Ser Leu Arg Ile Ser Cys Ala Ala Ser Gly Ser Leu Ser Asn Tyr
            20                  25                  30

Val Leu Gly Trp Phe Arg Gln Ala Pro Gly Lys Gly Arg Glu Phe Val
            35                  40                  45

Ala Ala Ile Asn Trp Arg Gly Asp Ile Thr Ile Gly Pro Pro Asn Val
        50                  55                  60

Glu Gly Arg Phe Thr Ile Ser Arg Asp Asn Ser Lys Asn Thr Leu Tyr
65                  70                  75                  80

Leu Gln Met Asn Ser Leu Arg Pro Glu Asp Thr Ala Val Tyr Tyr Cys
                85                  90                  95

Gly Ala Gly Thr Pro Leu Asn Pro Gly Ala Tyr Ile Tyr Asp Trp Ser
            100                 105                 110

Tyr Asp Tyr Trp Gly Gln Gly Thr Leu Val Thr Val Ser Ser
            115                 120                 125

<210> SEQ ID NO 7
<211> LENGTH: 126
<212> TYPE: PRT
<213> ORGANISM: Artificial Sequence
<220> FEATURE:
<223> OTHER INFORMATION: Nanobody sequence

<400> SEQUENCE: 7

Glu Val Gln Leu Leu Glu Ser Gly Gly Gly Leu Val Gln Pro Gly Gly
1               5                   10                  15

Ser Leu Ser Ile Ser Cys Ala Ala Ser Gly Gly Ser Leu Ser Asn Tyr
            20                  25                  30

Val Leu Gly Trp Phe Arg Gln Ala Pro Gly Lys Gly Arg Glu Phe Val
            35                  40                  45

Ala Ala Ile Asn Trp Arg Gly Asp Ile Thr Ile Gly Pro Pro Asn Val
        50                  55                  60

Glu Gly Arg Phe Thr Ile Ser Arg Asp Asn Ser Lys Asn Thr Leu Tyr
65                  70                  75                  80

Leu Gln Met Asn Ser Leu Arg Pro Asp Asp Thr Ala Val Tyr Tyr Cys
                85                  90                  95

Gly Ala Gly Thr Pro Leu Asn Pro Gly Ala Tyr Ile Tyr Asp Trp Ser
            100                 105                 110

Tyr Asp Tyr Trp Gly Gln Gly Thr Leu Val Thr Val Ser Ser
            115                 120                 125

<210> SEQ ID NO 8
<211> LENGTH: 126
<212> TYPE: PRT

-continued

<213> ORGANISM: Artificial Sequence
<220> FEATURE:
<223> OTHER INFORMATION: Nanobody sequence

<400> SEQUENCE: 8

Glu Val Gln Leu Leu Glu Ser Gly Gly Gly Leu Val Gln Pro Gly Gly
1               5                   10                  15

Ser Leu Ser Ile Ser Cys Ala Ala Ser Gly Gly Ser Leu Ser Asn Tyr
            20                  25                  30

Val Leu Gly Trp Phe Arg Gln Ala Pro Gly Lys Gly Arg Glu Phe Val
        35                  40                  45

Ala Ala Ile Asn Trp Arg Gly Asp Ile Thr Ile Gly Pro Pro Asn Val
    50                  55                  60

Glu Gly Arg Phe Thr Ile Ser Arg Asp Asn Ser Lys Asn Thr Leu Tyr
65                  70                  75                  80

Leu Gln Met Asn Ser Leu Ala Pro Glu Asp Thr Ala Val Tyr Tyr Cys
                85                  90                  95

Gly Ala Gly Thr Pro Leu Asn Pro Gly Ala Tyr Ile Tyr Asp Trp Ser
            100                 105                 110

Tyr Asp Tyr Trp Gly Gln Gly Thr Leu Val Thr Val Ser Ser
        115                 120                 125

<210> SEQ ID NO 9
<211> LENGTH: 126
<212> TYPE: PRT
<213> ORGANISM: Artificial Sequence
<220> FEATURE:
<223> OTHER INFORMATION: Nanobody sequence

<400> SEQUENCE: 9

Glu Val Gln Leu Leu Glu Ser Gly Gly Gly Leu Val Gln Pro Gly Gly
1               5                   10                  15

Ser Leu Arg Leu Ser Cys Ala Ala Ser Gly Gly Ser Leu Ser Asn Tyr
            20                  25                  30

Val Leu Gly Trp Phe Arg Gln Ala Pro Gly Lys Gly Arg Glu Phe Val
        35                  40                  45

Ala Ala Ile Asn Trp Arg Asp Asp Ile Thr Ile Gly Pro Pro Asn Val
    50                  55                  60

Glu Gly Arg Phe Thr Ile Ser Arg Asp Asn Ala Lys Asn Thr Leu Tyr
65                  70                  75                  80

Leu Gln Met Asn Ser Leu Arg Pro Glu Asp Thr Ala Val Tyr Tyr Cys
                85                  90                  95

Gly Ala Gly Thr Pro Leu Asn Pro Gly Ala Tyr Ile Tyr Asp Trp Ser
            100                 105                 110

Tyr Asp Tyr Trp Gly Gln Gly Thr Leu Val Thr Val Ser Ser
        115                 120                 125

<210> SEQ ID NO 10
<211> LENGTH: 126
<212> TYPE: PRT
<213> ORGANISM: Artificial Sequence
<220> FEATURE:
<223> OTHER INFORMATION: Nanobody sequence

<400> SEQUENCE: 10

Asp Val Gln Leu Leu Glu Ser Gly Gly Gly Leu Val Gln Pro Gly Gly
1               5                   10                  15

Ser Leu Arg Leu Ser Cys Ala Ala Ser Gly Gly Ser Leu Ser Asn Tyr
            20                  25                  30

Val Leu Gly Trp Phe Arg Gln Ala Pro Gly Lys Gly Arg Glu Phe Val
            35                  40                  45

Ala Ala Ile Asn Trp Arg Asp Asp Ile Thr Ile Gly Pro Pro Asn Val
 50                  55                  60

Glu Gly Arg Phe Thr Ile Ser Arg Asp Asn Ala Lys Asn Thr Leu Tyr
 65                  70                  75                  80

Leu Gln Met Asn Ser Leu Arg Pro Glu Asp Thr Ala Val Tyr Tyr Cys
                 85                  90                  95

Gly Ala Gly Thr Pro Leu Asn Pro Gly Ala Tyr Ile Tyr Asp Trp Ser
            100                 105                 110

Tyr Asp Tyr Trp Gly Gln Gly Thr Leu Val Thr Val Ser Ser
            115                 120                 125

<210> SEQ ID NO 11
<211> LENGTH: 126
<212> TYPE: PRT
<213> ORGANISM: Artificial Sequence
<220> FEATURE:
<223> OTHER INFORMATION: Nanobody sequence

<400> SEQUENCE: 11

Glu Val Gln Leu Leu Glu Ser Gly Gly Gly Leu Val Gln Pro Gly Gly
 1               5                  10                  15

Ser Leu Ser Ile Ser Cys Ala Ala Ser Gly Gly Ser Leu Ser Asn Tyr
            20                  25                  30

Val Leu Gly Trp Phe Arg Gln Ala Pro Gly Lys Gly Arg Glu Phe Val
            35                  40                  45

Ala Ala Ile Asn Trp Arg Gly Asp Ile Thr Ile Gly Pro Pro Asn Val
 50                  55                  60

Glu Gly Arg Phe Thr Ile Ser Arg Asp Asn Ala Lys Asn Thr Leu Tyr
 65                  70                  75                  80

Leu Gln Met Asn Ser Leu Ala Pro Asp Asp Thr Ala Val Tyr Tyr Cys
                 85                  90                  95

Gly Ala Gly Thr Pro Leu Asn Pro Gly Ala Tyr Ile Tyr Asp Trp Ser
            100                 105                 110

Tyr Asp Tyr Trp Gly Gln Gly Thr Leu Val Thr Val Ser Ser
            115                 120                 125

<210> SEQ ID NO 12
<211> LENGTH: 126
<212> TYPE: PRT
<213> ORGANISM: Artificial Sequence
<220> FEATURE:
<223> OTHER INFORMATION: Nanobody sequence

<400> SEQUENCE: 12

Glu Val Gln Leu Leu Glu Ser Gly Gly Gly Leu Val Gln Pro Gly Gly
 1               5                  10                  15

Ser Leu Ser Ile Ser Cys Ala Ala Ser Gly Gly Ser Leu Ser Asn Tyr
            20                  25                  30

Val Leu Gly Trp Phe Arg Gln Ala Pro Gly Lys Gly Arg Glu Phe Val
            35                  40                  45

Ala Ala Ile Asn Trp Arg Gly Asp Ile Thr Ile Gly Pro Pro Asn Val
 50                  55                  60

Glu Gly Arg Phe Thr Ile Ser Arg Asp Asn Ala Lys Asn Thr Leu Tyr
 65                  70                  75                  80

Leu Gln Met Asn Ser Leu Arg Pro Glu Asp Thr Ala Val Tyr Tyr Cys

```
                85                  90                  95
Gly Ala Gly Thr Pro Leu Asn Pro Gly Ala Tyr Ile Tyr Asp Trp Ser
            100                 105                 110
Tyr Asp Tyr Trp Gly Gln Gly Thr Leu Val Thr Val Ser Ser
        115                 120                 125
```

```
<210> SEQ ID NO 13
<211> LENGTH: 126
<212> TYPE: PRT
<213> ORGANISM: Artificial Sequence
<220> FEATURE:
<223> OTHER INFORMATION: Nanobody sequence

<400> SEQUENCE: 13

Glu Val Gln Leu Leu Glu Ser Gly Gly Gly Leu Val Gln Pro Gly Gly
1               5                   10                  15
Ser Leu Ser Ile Ser Cys Ala Ala Ser Gly Gly Ser Leu Ser Asn Tyr
            20                  25                  30
Val Leu Gly Trp Phe Arg Gln Ala Pro Gly Lys Gly Arg Glu Phe Val
        35                  40                  45
Ala Ala Ile Asn Trp Arg Gly Asp Ile Thr Ile Gly Pro Pro Asn Val
    50                  55                  60
Glu Gly Arg Phe Thr Ile Ser Arg Asp Asn Ser Lys Asn Thr Leu Tyr
65                  70                  75                  80
Leu Gln Met Asn Ser Leu Arg Pro Asp Asp Thr Ala Val Tyr Tyr Cys
                85                  90                  95
Gly Ala Gly Thr Pro Leu Asn Pro Gly Ala Tyr Ile Tyr Asp Trp Ser
            100                 105                 110
Tyr Asp Tyr Trp Gly Gln Gly Thr Leu Val Thr Val Ser Ser
        115                 120                 125
```

```
<210> SEQ ID NO 14
<211> LENGTH: 126
<212> TYPE: PRT
<213> ORGANISM: Artificial Sequence
<220> FEATURE:
<223> OTHER INFORMATION: Nanobody sequence

<400> SEQUENCE: 14

Glu Val Gln Leu Leu Glu Ser Gly Gly Gly Leu Val Gln Pro Gly Gly
1               5                   10                  15
Ser Leu Ser Ile Ser Cys Ala Ala Ser Gly Gly Ser Leu Ser Asn Tyr
            20                  25                  30
Val Leu Gly Trp Phe Arg Gln Ala Pro Gly Lys Gly Arg Glu Phe Val
        35                  40                  45
Ala Ala Ile Asn Trp Arg Gly Asp Ile Thr Ile Gly Pro Pro Asn Val
    50                  55                  60
Glu Gly Arg Phe Thr Ile Ser Arg Asp Asn Ala Lys Asn Thr Gly Tyr
65                  70                  75                  80
Leu Gln Met Asn Ser Leu Ala Pro Asp Asp Thr Ala Val Tyr Tyr Cys
                85                  90                  95
Gly Ala Gly Thr Pro Leu Asn Pro Gly Ala Tyr Ile Tyr Asp Trp Ser
            100                 105                 110
Tyr Asp Tyr Trp Gly Gln Gly Thr Leu Val Thr Val Ser Ser
        115                 120                 125
```

```
<210> SEQ ID NO 15
<211> LENGTH: 126
```

```
<212> TYPE: PRT
<213> ORGANISM: Artificial Sequence
<220> FEATURE:
<223> OTHER INFORMATION: Nanobody sequence

<400> SEQUENCE: 15

Glu Val Gln Leu Leu Glu Ser Gly Gly Gly Leu Val Gln Ala Gly Gly
1               5                   10                  15

Ser Leu Ser Ile Ser Cys Ala Ala Ser Gly Gly Ser Leu Ser Asn Tyr
            20                  25                  30

Val Leu Gly Trp Phe Arg Gln Ala Pro Gly Lys Gly Arg Glu Phe Val
        35                  40                  45

Ala Ala Ile Asn Trp Arg Gly Asp Ile Thr Ile Gly Pro Pro Asn Val
    50                  55                  60

Glu Gly Arg Phe Thr Ile Ser Arg Asp Asn Ala Lys Asn Thr Gly Tyr
65                  70                  75                  80

Leu Gln Met Asn Ser Leu Ala Pro Asp Thr Ala Val Tyr Tyr Cys
                85                  90                  95

Gly Ala Gly Thr Pro Leu Asn Pro Gly Ala Tyr Ile Tyr Asp Trp Ser
            100                 105                 110

Tyr Asp Tyr Trp Gly Gln Gly Thr Leu Val Thr Val Ser Ser
        115                 120                 125

<210> SEQ ID NO 16
<211> LENGTH: 126
<212> TYPE: PRT
<213> ORGANISM: Artificial Sequence
<220> FEATURE:
<223> OTHER INFORMATION: Nanobody sequence

<400> SEQUENCE: 16

Glu Val Gln Leu Leu Glu Ser Gly Gly Gly Leu Val Gln Pro Gly Gly
1               5                   10                  15

Ser Leu Ser Ile Ser Cys Ala Ala Ser Gly Gly Ser Leu Ser Asn Tyr
            20                  25                  30

Val Leu Gly Trp Phe Arg Gln Ala Pro Gly Lys Glu Arg Glu Phe Val
        35                  40                  45

Ala Ala Ile Asn Trp Arg Gly Asp Ile Thr Ile Gly Pro Pro Asn Val
    50                  55                  60

Glu Gly Arg Phe Thr Ile Ser Arg Asp Asn Ala Lys Asn Thr Gly Tyr
65                  70                  75                  80

Leu Gln Met Asn Ser Leu Ala Pro Asp Thr Ala Val Tyr Tyr Cys
                85                  90                  95

Gly Ala Gly Thr Pro Leu Asn Pro Gly Ala Tyr Ile Tyr Asp Trp Ser
            100                 105                 110

Tyr Asp Tyr Trp Gly Gln Gly Thr Leu Val Thr Val Ser Ser
        115                 120                 125

<210> SEQ ID NO 17
<211> LENGTH: 126
<212> TYPE: PRT
<213> ORGANISM: Artificial Sequence
<220> FEATURE:
<223> OTHER INFORMATION: Nanobody sequence

<400> SEQUENCE: 17

Glu Val Gln Leu Leu Glu Ser Gly Gly Gly Leu Val Gln Pro Gly Gly
1               5                   10                  15

Ser Leu Arg Leu Ser Cys Ala Ala Ser Gly Gly Ser Leu Ser Asn Tyr
```

-continued

```
                20                  25                  30
Val Leu Gly Trp Phe Arg Gln Ala Pro Gly Lys Gly Arg Glu Phe Val
            35                  40                  45

Ala Ala Ile Asn Trp Arg Gly Asp Ile Thr Ile Gly Pro Pro Asn Val
        50                  55                  60

Glu Gly Arg Phe Thr Ile Ser Arg Asp Asn Ala Lys Asn Thr Gly Tyr
65                  70                  75                  80

Leu Gln Met Asn Ser Leu Ala Pro Glu Asp Thr Ala Val Tyr Tyr Cys
                85                  90                  95

Gly Ala Gly Thr Pro Leu Asn Pro Gly Ala Tyr Ile Tyr Asp Trp Ser
            100                 105                 110

Tyr Asp Tyr Trp Gly Gln Gly Thr Leu Val Thr Val Ser Ser
        115                 120                 125
```

<210> SEQ ID NO 18
<211> LENGTH: 126
<212> TYPE: PRT
<213> ORGANISM: Artificial Sequence
<220> FEATURE:
<223> OTHER INFORMATION: Nanobody sequence

<400> SEQUENCE: 18

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Gly Ser Leu Ser Asn Tyr
            20                  25                  30

Val Leu Gly Trp Phe Arg Gln Ala Pro Gly Lys Gly Arg Glu Phe Val
        35                  40                  45

Ala Ala Ile Asn Trp Arg Gly Asp Ile Thr Ile Gly Pro Pro Asn Val
    50                  55                  60

Glu Gly Arg Phe Thr Ile Ser Arg Asp Asn Ser Lys Asn Thr Leu Tyr
65                  70                  75                  80

Leu Gln Met Asn Ser Leu Ala Pro Glu Asp Thr Ala Val Tyr Tyr Cys
                85                  90                  95

Gly Ala Gly Thr Pro Leu Asn Pro Gly Ala Tyr Ile Tyr Asp Trp Ser
            100                 105                 110

Tyr Asp Tyr Trp Gly Gln Gly Thr Leu Val Thr Val Ser Ser
        115                 120                 125
```

<210> SEQ ID NO 19
<211> LENGTH: 126
<212> TYPE: PRT
<213> ORGANISM: Artificial Sequence
<220> FEATURE:
<223> OTHER INFORMATION: Nanobody sequence

<400> SEQUENCE: 19

```
Glu Val Gln Leu Leu Glu Ser Gly Gly Gly Leu Val Gln Ala Gly Gly
1               5                   10                  15

Ser Leu Arg Leu Ser Cys Ala Ala Ser Gly Gly Ser Leu Ser Asn Tyr
            20                  25                  30

Val Leu Gly Trp Phe Arg Gln Ala Pro Gly Lys Gly Arg Glu Phe Val
        35                  40                  45

Ala Ala Ile Asn Trp Arg Gly Asp Ile Thr Ile Gly Pro Pro Asn Val
    50                  55                  60

Glu Gly Arg Phe Thr Ile Ser Arg Asp Asn Ala Lys Asn Thr Leu Tyr
65                  70                  75                  80
```

```
Leu Gln Met Asn Ser Leu Ala Pro Glu Asp Thr Ala Val Tyr Tyr Cys
                85                  90                  95

Gly Ala Gly Thr Pro Leu Asn Pro Gly Ala Tyr Ile Tyr Asp Trp Ser
            100                 105                 110

Tyr Asp Tyr Trp Gly Gln Gly Thr Leu Val Thr Val Ser Ser
        115                 120                 125

<210> SEQ ID NO 20
<211> LENGTH: 126
<212> TYPE: PRT
<213> ORGANISM: Artificial Sequence
<220> FEATURE:
<223> OTHER INFORMATION: Nanobody sequence

<400> SEQUENCE: 20

Glu Val Gln Leu Leu Glu Ser Gly Gly Gly Leu Val Gln Pro Gly Gly
1               5                   10                  15

Ser Leu Arg Leu Ser Cys Ala Ala Ser Gly Gly Ser Leu Ser Asn Tyr
            20                  25                  30

Val Leu Gly Trp Phe Arg Gln Ala Pro Gly Lys Gly Arg Glu Phe Val
        35                  40                  45

Ala Ala Ile Asn Trp Arg Gly Asp Ile Thr Ile Gly Pro Pro Asn Val
    50                  55                  60

Glu Gly Arg Phe Thr Ile Ser Arg Asp Asn Ser Lys Asn Thr Leu Tyr
65                  70                  75                  80

Leu Gln Met Asn Ser Leu Arg Pro Glu Asp Thr Ala Val Tyr Tyr Cys
                85                  90                  95

Gly Ala Gly Thr Pro Leu Asn Pro Gly Ala Tyr Ile Tyr Asp Trp Ser
            100                 105                 110

Tyr Asp Tyr Trp Gly Gln Gly Thr Leu Val Thr Val Ser Ser
        115                 120                 125

<210> SEQ ID NO 21
<211> LENGTH: 126
<212> TYPE: PRT
<213> ORGANISM: Artificial Sequence
<220> FEATURE:
<223> OTHER INFORMATION: Nanobody sequence

<400> SEQUENCE: 21

Asp Val Gln Leu Leu Glu Ser Gly Gly Gly Leu Val Gln Pro Gly Gly
1               5                   10                  15

Ser Leu Arg Leu Ser Cys Ala Ala Ser Gly Gly Ser Leu Ser Asn Tyr
            20                  25                  30

Val Leu Gly Trp Phe Arg Gln Ala Pro Gly Lys Gly Arg Glu Phe Val
        35                  40                  45

Ala Ala Ile Asn Trp Arg Gly Asp Ile Thr Ile Gly Pro Pro Asn Val
    50                  55                  60

Glu Gly Arg Phe Thr Ile Ser Arg Asp Asn Ser Lys Asn Thr Leu Tyr
65                  70                  75                  80

Leu Gln Met Asn Ser Leu Arg Pro Glu Asp Thr Ala Val Tyr Tyr Cys
                85                  90                  95

Gly Ala Gly Thr Pro Leu Asn Pro Gly Ala Tyr Ile Tyr Asp Trp Ser
            100                 105                 110

Tyr Asp Tyr Trp Gly Gln Gly Thr Leu Val Thr Val Ser Ser
        115                 120                 125

<210> SEQ ID NO 22
```

<211> LENGTH: 126
<212> TYPE: PRT
<213> ORGANISM: Artificial Sequence
<220> FEATURE:
<223> OTHER INFORMATION: Nanobody sequence

<400> SEQUENCE: 22

Glu Val Gln Leu Leu Glu Ser Gly Gly Gly Leu Val Gln Pro Gly Gly
1               5                   10                  15

Ser Leu Arg Leu Ser Cys Ala Ala Ser Gly Gly Ser Leu Ser Asn Tyr
            20                  25                  30

Val Leu Gly Trp Phe Arg Gln Ala Pro Gly Lys Gly Arg Glu Phe Val
        35                  40                  45

Ala Ala Ile Asn Trp Arg Asp Asp Ile Thr Ile Gly Pro Pro Asn Val
    50                  55                  60

Glu Gly Arg Phe Thr Ile Ser Arg Asp Asn Ser Lys Asn Thr Leu Tyr
65                  70                  75                  80

Leu Gln Met Asn Ser Leu Arg Pro Glu Asp Thr Ala Val Tyr Tyr Cys
                85                  90                  95

Gly Ala Gly Thr Pro Leu Asn Pro Gly Ala Tyr Ile Tyr Asp Trp Ser
            100                 105                 110

Tyr Asp Tyr Trp Gly Gln Gly Thr Leu Val Thr Val Ser Ser
        115                 120                 125

<210> SEQ ID NO 23
<211> LENGTH: 126
<212> TYPE: PRT
<213> ORGANISM: Artificial Sequence
<220> FEATURE:
<223> OTHER INFORMATION: Nanobody sequence

<400> SEQUENCE: 23

Asp Val Gln Leu Leu Glu Ser Gly Gly Gly Leu Val Gln Pro Gly Gly
1               5                   10                  15

Ser Leu Arg Leu Ser Cys Ala Ala Ser Gly Gly Ser Leu Ser Asn Tyr
            20                  25                  30

Val Leu Gly Trp Phe Arg Gln Ala Pro Gly Lys Gly Arg Glu Phe Val
        35                  40                  45

Ala Ala Ile Asn Trp Arg Asp Asp Ile Thr Ile Gly Pro Pro Asn Val
    50                  55                  60

Glu Gly Arg Phe Thr Ile Ser Arg Asp Asn Ser Lys Asn Thr Leu Tyr
65                  70                  75                  80

Leu Gln Met Asn Ser Leu Arg Pro Glu Asp Thr Ala Val Tyr Tyr Cys
                85                  90                  95

Gly Ala Gly Thr Pro Leu Asn Pro Gly Ala Tyr Ile Tyr Asp Trp Ser
            100                 105                 110

Tyr Asp Tyr Trp Gly Gln Gly Thr Leu Val Thr Val Ser Ser
        115                 120                 125

<210> SEQ ID NO 24
<211> LENGTH: 126
<212> TYPE: PRT
<213> ORGANISM: Artificial Sequence
<220> FEATURE:
<223> OTHER INFORMATION: Nanobody sequence

<400> SEQUENCE: 24

Glu Val Gln Leu Val Glu Ser Gly Gly Gly Leu Val Gln Pro Gly Gly
1               5                   10                  15

-continued

```
Ser Leu Arg Leu Ser Cys Ala Ala Ser Gly Gly Ser Leu Ser Asn Tyr
            20                  25                  30

Val Leu Gly Trp Phe Arg Gln Ala Pro Gly Lys Glu Arg Glu Phe Val
        35                  40                  45

Ala Ala Ile Asn Trp Arg Gly Asp Ile Thr Ile Gly Pro Pro Asn Val
    50                  55                  60

Glu Gly Arg Phe Thr Ile Ser Arg Asp Asn Ala Lys Asn Thr Gly Tyr
65                  70                  75                  80

Leu Gln Met Asn Ser Leu Ala Pro Asp Asp Thr Ala Val Tyr Tyr Cys
                85                  90                  95

Gly Ala Gly Thr Pro Leu Asn Pro Gly Ala Tyr Ile Tyr Asp Trp Ser
            100                 105                 110

Tyr Asp Tyr Trp Gly Gln Gly Thr Leu Val Thr Val Ser Ser
        115                 120                 125
```

<210> SEQ ID NO 25
<211> LENGTH: 126
<212> TYPE: PRT
<213> ORGANISM: Artificial Sequence
<220> FEATURE:
<223> OTHER INFORMATION: Nanobody sequence

<400> SEQUENCE: 25

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Gly Ser Leu Ser Asn Tyr
            20                  25                  30

Val Leu Gly Trp Phe Arg Gln Ala Pro Gly Lys Glu Arg Glu Phe Val
        35                  40                  45

Ala Ala Ile Asn Trp Arg Gly Asp Ile Thr Ile Gly Pro Pro Asn Val
    50                  55                  60

Glu Gly Arg Phe Thr Ile Ser Arg Asp Asn Ala Lys Asn Thr Gly Tyr
65                  70                  75                  80

Leu Gln Met Asn Ser Leu Arg Pro Asp Asp Thr Ala Val Tyr Tyr Cys
                85                  90                  95

Gly Ala Gly Thr Pro Leu Asn Pro Gly Ala Tyr Ile Tyr Asp Trp Ser
            100                 105                 110

Tyr Asp Tyr Trp Gly Gln Gly Thr Leu Val Thr Val Ser Ser
        115                 120                 125
```

<210> SEQ ID NO 26
<211> LENGTH: 126
<212> TYPE: PRT
<213> ORGANISM: Artificial Sequence
<220> FEATURE:
<223> OTHER INFORMATION: Nanobody sequence

<400> SEQUENCE: 26

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Gly Ser Leu Ser Asn Tyr
            20                  25                  30

Val Leu Gly Trp Phe Arg Gln Ala Pro Gly Lys Glu Arg Glu Phe Val
        35                  40                  45

Ala Ala Ile Asn Trp Arg Gly Asp Ile Thr Ile Gly Pro Pro Asn Val
    50                  55                  60

Glu Gly Arg Phe Thr Ile Ser Arg Asp Asn Ala Lys Asn Thr Gly Tyr
65                  70                  75                  80
```

-continued

Leu Gln Met Asn Ser Leu Ala Pro Glu Asp Thr Ala Val Tyr Tyr Cys
                85                  90                  95

Gly Ala Gly Thr Pro Leu Asn Pro Gly Ala Tyr Ile Tyr Asp Trp Ser
            100                 105                 110

Tyr Asp Tyr Trp Gly Gln Gly Thr Leu Val Thr Val Ser Ser
        115                 120                 125

<210> SEQ ID NO 27
<211> LENGTH: 126
<212> TYPE: PRT
<213> ORGANISM: Artificial Sequence
<220> FEATURE:
<223> OTHER INFORMATION: Nanobody sequence

<400> SEQUENCE: 27

Asp Val Gln Leu Val Glu Ser Gly Gly Gly Leu Val Gln Pro Gly Gly
1               5                   10                  15

Ser Leu Arg Leu Ser Cys Ala Ala Ser Gly Gly Ser Leu Ser Asn Tyr
            20                  25                  30

Val Leu Gly Trp Phe Arg Gln Ala Pro Gly Lys Glu Arg Glu Phe Val
        35                  40                  45

Ala Ala Ile Asn Trp Arg Gly Asp Ile Thr Ile Gly Pro Pro Asn Val
    50                  55                  60

Glu Gly Arg Phe Thr Ile Ser Arg Asp Asn Ala Lys Asn Thr Gly Tyr
65                  70                  75                  80

Leu Gln Met Asn Ser Leu Ala Pro Glu Asp Thr Ala Val Tyr Tyr Cys
                85                  90                  95

Gly Ala Gly Thr Pro Leu Asn Pro Gly Ala Tyr Ile Tyr Asp Trp Ser
            100                 105                 110

Tyr Asp Tyr Trp Gly Gln Gly Thr Leu Val Thr Val Ser Ser
        115                 120                 125

<210> SEQ ID NO 28
<211> LENGTH: 126
<212> TYPE: PRT
<213> ORGANISM: Artificial Sequence
<220> FEATURE:
<223> OTHER INFORMATION: Nanobody sequence

<400> SEQUENCE: 28

Glu Val Gln Leu Val Glu Ser Gly Gly Gly Leu Val Gln Pro Gly Gly
1               5                   10                  15

Ser Leu Arg Leu Ser Cys Ala Ala Ser Gly Gly Ser Leu Ser Asn Tyr
            20                  25                  30

Val Leu Gly Trp Phe Arg Gln Ala Pro Gly Lys Glu Arg Glu Phe Val
        35                  40                  45

Ala Ala Ile Asn Trp Arg Gly Asp Ile Thr Ile Gly Pro Pro Asn Val
    50                  55                  60

Glu Gly Arg Phe Thr Ile Ser Arg Asp Asn Ala Lys Asn Thr Gly Tyr
65                  70                  75                  80

Leu Gln Met Asn Ser Leu Arg Pro Glu Asp Thr Ala Val Tyr Tyr Cys
                85                  90                  95

Gly Ala Gly Thr Pro Leu Asn Pro Gly Ala Tyr Ile Tyr Asp Trp Ser
            100                 105                 110

Tyr Asp Tyr Trp Gly Gln Gly Thr Leu Val Thr Val Ser Ser
        115                 120                 125

<210> SEQ ID NO 29
<211> LENGTH: 126
<212> TYPE: PRT
<213> ORGANISM: Artificial Sequence
<220> FEATURE:
<223> OTHER INFORMATION: Nanobody sequence

<400> SEQUENCE: 29

```
Asp Val Gln Leu Val Glu Ser Gly Gly Gly Leu Val Gln Pro Gly Gly
1               5                   10                  15

Ser Leu Arg Leu Ser Cys Ala Ala Ser Gly Ser Leu Ser Asn Tyr
            20                  25                  30

Val Leu Gly Trp Phe Arg Gln Ala Pro Gly Lys Glu Arg Glu Phe Val
        35                  40                  45

Ala Ala Ile Asn Trp Arg Gly Asp Ile Thr Ile Gly Pro Pro Asn Val
    50                  55                  60

Glu Gly Arg Phe Thr Ile Ser Arg Asp Asn Ala Lys Asn Thr Gly Tyr
65                  70                  75                  80

Leu Gln Met Asn Ser Leu Arg Pro Glu Asp Thr Ala Val Tyr Tyr Cys
                85                  90                  95

Gly Ala Gly Thr Pro Leu Asn Pro Gly Ala Tyr Ile Tyr Asp Trp Ser
            100                 105                 110

Tyr Asp Tyr Trp Gly Gln Gly Thr Leu Val Thr Val Ser Ser
        115                 120                 125
```

<210> SEQ ID NO 30
<211> LENGTH: 126
<212> TYPE: PRT
<213> ORGANISM: Artificial Sequence
<220> FEATURE:
<223> OTHER INFORMATION: Nanobody sequence

<400> SEQUENCE: 30

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Gly Ser Leu Ser Asn Tyr
            20                  25                  30

Val Leu Gly Trp Phe Arg Gln Ala Pro Gly Lys Glu Arg Glu Phe Val
        35                  40                  45

Ala Ala Ile Asn Trp Arg Gly Asp Ile Thr Ile Gly Pro Pro Asn Val
    50                  55                  60

Glu Gly Arg Phe Thr Ile Ser Arg Asp Asn Ala Lys Asn Thr Gly Tyr
65                  70                  75                  80

Leu Gln Met Asn Ser Leu Ala Pro Asp Asp Thr Ala Val Tyr Tyr Cys
                85                  90                  95

Gly Ala Gly Thr Pro Leu Asn Pro Gly Ala Tyr Ile Tyr Asp Trp Ser
            100                 105                 110

Tyr Asp Tyr Trp Gly Arg Gly Thr Leu Val Thr Val Ser Ser
        115                 120                 125
```

<210> SEQ ID NO 31
<211> LENGTH: 126
<212> TYPE: PRT
<213> ORGANISM: Artificial Sequence
<220> FEATURE:
<223> OTHER INFORMATION: Nanobody sequence

<400> SEQUENCE: 31

```
Glu Val Gln Leu Val Glu Ser Gly Gly Gly Leu Val Gln Pro Gly Gly
1               5                   10                  15
```

```
Ser Leu Arg Leu Ser Cys Ala Ala Ser Gly Gly Ser Leu Ser Asn Tyr
            20                  25                  30

Val Leu Gly Trp Phe Arg Gln Ala Pro Gly Lys Glu Arg Glu Phe Val
            35                  40                  45

Ala Ala Ile Asn Trp Arg Gly Asp Ile Thr Ile Gly Pro Pro Asn Val
 50                  55                  60

Glu Gly Arg Phe Thr Ile Ser Arg Asp Asn Ala Lys Asn Thr Gly Tyr
 65                  70                  75                  80

Leu Gln Met Asn Ser Leu Arg Pro Asp Asp Thr Ala Val Tyr Tyr Cys
                85                  90                  95

Gly Ala Gly Thr Pro Leu Asn Pro Gly Ala Tyr Ile Tyr Asp Trp Ser
            100                 105                 110

Tyr Asp Tyr Trp Gly Arg Gly Thr Leu Val Thr Val Ser Ser
            115                 120                 125
```

<210> SEQ ID NO 32
<211> LENGTH: 126
<212> TYPE: PRT
<213> ORGANISM: Artificial Sequence
<220> FEATURE:
<223> OTHER INFORMATION: Nanobody sequence

<400> SEQUENCE: 32

```
Glu Val Gln Leu Val Glu Ser Gly Gly Gly Leu Val Gln Pro Gly Gly
 1               5                  10                  15

Ser Leu Arg Leu Ser Cys Ala Ala Ser Gly Gly Ser Leu Ser Asn Tyr
            20                  25                  30

Val Leu Gly Trp Phe Arg Gln Ala Pro Gly Lys Glu Arg Glu Phe Val
            35                  40                  45

Ala Ala Ile Asn Trp Arg Gly Asp Ile Thr Ile Gly Pro Pro Asn Val
 50                  55                  60

Glu Gly Arg Phe Thr Ile Ser Arg Asp Asn Ala Lys Asn Thr Gly Tyr
 65                  70                  75                  80

Leu Gln Met Asn Ser Leu Ala Pro Glu Asp Thr Ala Val Tyr Tyr Cys
                85                  90                  95

Gly Ala Gly Thr Pro Leu Asn Pro Gly Ala Tyr Ile Tyr Asp Trp Ser
            100                 105                 110

Tyr Asp Tyr Trp Gly Arg Gly Thr Leu Val Thr Val Ser Ser
            115                 120                 125
```

<210> SEQ ID NO 33
<211> LENGTH: 126
<212> TYPE: PRT
<213> ORGANISM: Artificial Sequence
<220> FEATURE:
<223> OTHER INFORMATION: Nanobody sequence

<400> SEQUENCE: 33

```
Glu Val Gln Leu Val Glu Ser Gly Gly Gly Leu Val Gln Pro Gly Gly
 1               5                  10                  15

Ser Leu Arg Leu Ser Cys Ala Ala Ser Gly Gly Ser Leu Ser Asn Tyr
            20                  25                  30

Val Leu Gly Trp Phe Arg Gln Ala Pro Gly Lys Glu Arg Glu Phe Val
            35                  40                  45

Ala Ala Ile Asn Trp Arg Gly Asp Ile Thr Ile Gly Pro Pro Asn Val
 50                  55                  60

Glu Gly Arg Phe Thr Ile Ser Arg Asp Asn Ala Lys Asn Thr Gly Tyr
```

```
                65                  70                  75                  80
Leu Gln Met Asn Ser Leu Arg Pro Glu Asp Thr Ala Val Tyr Tyr Cys
                    85                  90                  95

Gly Ala Gly Thr Pro Leu Asn Pro Gly Ala Tyr Ile Tyr Asp Trp Ser
            100                 105                 110

Tyr Asp Tyr Trp Gly Arg Gly Thr Leu Val Thr Val Ser Ser
        115                 120                 125

<210> SEQ ID NO 34
<211> LENGTH: 126
<212> TYPE: PRT
<213> ORGANISM: Artificial Sequence
<220> FEATURE:
<223> OTHER INFORMATION: Nanobody sequence

<400> SEQUENCE: 34

Asp Val Gln Leu Val Glu Ser Gly Gly Gly Leu Val Gln Pro Gly Gly
1               5                   10                  15

Ser Leu Arg Leu Ser Cys Ala Ala Ser Gly Gly Ser Leu Ser Asn Tyr
            20                  25                  30

Val Leu Gly Trp Phe Arg Gln Ala Pro Gly Lys Glu Arg Glu Phe Val
        35                  40                  45

Ala Ala Ile Asn Trp Arg Gly Asp Ile Thr Ile Gly Pro Pro Asn Val
    50                  55                  60

Glu Gly Arg Phe Thr Ile Ser Arg Asp Asn Ala Lys Asn Thr Gly Tyr
65                  70                  75                  80

Leu Gln Met Asn Ser Leu Arg Pro Glu Asp Thr Ala Val Tyr Tyr Cys
                85                  90                  95

Gly Ala Gly Thr Pro Leu Asn Pro Gly Ala Tyr Ile Tyr Asp Trp Ser
            100                 105                 110

Tyr Asp Tyr Trp Gly Arg Gly Thr Leu Val Thr Val Ser Ser
        115                 120                 125

<210> SEQ ID NO 35
<211> LENGTH: 30
<212> TYPE: PRT
<213> ORGANISM: Artificial Sequence
<220> FEATURE:
<223> OTHER INFORMATION: Framework sequence

<400> SEQUENCE: 35

Glu Val Gln Leu Val Glu Ser Gly Gly Gly Leu Val Gln Ala Gly Gly
1               5                   10                  15

Ser Leu Ser Ile Ser Cys Ala Ala Ser Gly Gly Ser Leu Ser
            20                  25                  30

<210> SEQ ID NO 36
<211> LENGTH: 30
<212> TYPE: PRT
<213> ORGANISM: Artificial Sequence
<220> FEATURE:
<223> OTHER INFORMATION: Framework sequence

<400> SEQUENCE: 36

Asp Val Gln Leu Val Glu Ser Gly Gly Gly Leu Val Gln Ala Gly Gly
1               5                   10                  15

Ser Leu Ser Ile Ser Cys Ala Ala Ser Gly Gly Ser Leu Ser
            20                  25                  30

<210> SEQ ID NO 37
```

<211> LENGTH: 30
<212> TYPE: PRT
<213> ORGANISM: Artificial Sequence
<220> FEATURE:
<223> OTHER INFORMATION: Framework sequence

<400> SEQUENCE: 37

Glu Val Gln Leu Leu Glu Ser Gly Gly Gly Leu Val Gln Pro Gly Gly
1               5                   10                  15

Ser Leu Arg Leu Ser Cys Ala Ala Ser Gly Gly Ser Leu Ser
            20                  25                  30

<210> SEQ ID NO 38
<211> LENGTH: 30
<212> TYPE: PRT
<213> ORGANISM: Artificial Sequence
<220> FEATURE:
<223> OTHER INFORMATION: Framework sequence

<400> SEQUENCE: 38

Glu Val Gln Leu Leu Glu Ser Gly Gly Gly Leu Val Gln Pro Gly Gly
1               5                   10                  15

Ser Leu Arg Ile Ser Cys Ala Ala Ser Gly Gly Ser Leu Ser
            20                  25                  30

<210> SEQ ID NO 39
<211> LENGTH: 30
<212> TYPE: PRT
<213> ORGANISM: Artificial Sequence
<220> FEATURE:
<223> OTHER INFORMATION: Framework sequence

<400> SEQUENCE: 39

Asp Val Gln Leu Leu Glu Ser Gly Gly Gly Leu Val Gln Pro Gly Gly
1               5                   10                  15

Ser Leu Arg Ile Ser Cys Ala Ala Ser Gly Gly Ser Leu Ser
            20                  25                  30

<210> SEQ ID NO 40
<211> LENGTH: 30
<212> TYPE: PRT
<213> ORGANISM: Artificial Sequence
<220> FEATURE:
<223> OTHER INFORMATION: Framework sequence

<400> SEQUENCE: 40

Glu Val Gln Leu Leu Glu Ser Gly Gly Gly Leu Val Gln Pro Gly Gly
1               5                   10                  15

Ser Leu Ser Ile Ser Cys Ala Ala Ser Gly Gly Ser Leu Ser
            20                  25                  30

<210> SEQ ID NO 41
<211> LENGTH: 30
<212> TYPE: PRT
<213> ORGANISM: Artificial Sequence
<220> FEATURE:
<223> OTHER INFORMATION: Framework sequence

<400> SEQUENCE: 41

Asp Val Gln Leu Leu Glu Ser Gly Gly Gly Leu Val Gln Pro Gly Gly
1               5                   10                  15

Ser Leu Arg Leu Ser Cys Ala Ala Ser Gly Gly Ser Leu Ser
            20                  25                  30

<210> SEQ ID NO 42
<211> LENGTH: 30
<212> TYPE: PRT
<213> ORGANISM: Artificial Sequence
<220> FEATURE:
<223> OTHER INFORMATION: Framework sequence

<400> SEQUENCE: 42

Glu Val Gln Leu Leu Glu Ser Gly Gly Gly Leu Val Gln Ala Gly Gly
1               5                   10                  15
Ser Leu Ser Ile Ser Cys Ala Ala Ser Gly Gly Ser Leu Ser
            20                  25                  30

<210> SEQ ID NO 43
<211> LENGTH: 30
<212> TYPE: PRT
<213> ORGANISM: Artificial Sequence
<220> FEATURE:
<223> OTHER INFORMATION: Framework sequence

<400> SEQUENCE: 43

Glu Val Gln Leu Leu Glu Ser Gly Gly Gly Leu Val Gln Ala Gly Gly
1               5                   10                  15
Ser Leu Arg Leu Ser Cys Ala Ala Ser Gly Gly Ser Leu Ser
            20                  25                  30

<210> SEQ ID NO 44
<211> LENGTH: 30
<212> TYPE: PRT
<213> ORGANISM: Artificial Sequence
<220> FEATURE:
<223> OTHER INFORMATION: Framework sequence

<400> SEQUENCE: 44

Glu Val Gln Leu Val Glu Ser Gly Gly Gly Leu Val Gln Pro Gly Gly
1               5                   10                  15
Ser Leu Arg Leu Ser Cys Ala Ala Ser Gly Gly Ser Leu Ser
            20                  25                  30

<210> SEQ ID NO 45
<211> LENGTH: 30
<212> TYPE: PRT
<213> ORGANISM: Artificial Sequence
<220> FEATURE:
<223> OTHER INFORMATION: Framework sequence

<400> SEQUENCE: 45

Asp Val Gln Leu Val Glu Ser Gly Gly Gly Leu Val Gln Pro Gly Gly
1               5                   10                  15
Ser Leu Arg Leu Ser Cys Ala Ala Ser Gly Gly Ser Leu Ser
            20                  25                  30

<210> SEQ ID NO 46
<211> LENGTH: 5
<212> TYPE: PRT
<213> ORGANISM: Artificial Sequence
<220> FEATURE:
<223> OTHER INFORMATION: CDR sequence

<400> SEQUENCE: 46

Asn Tyr Val Leu Gly
1               5

<210> SEQ ID NO 47
<211> LENGTH: 14

```
<212> TYPE: PRT
<213> ORGANISM: Artificial Sequence
<220> FEATURE:
<223> OTHER INFORMATION: Framework sequence

<400> SEQUENCE: 47

Trp Phe Arg Gln Ala Pro Gly Lys Glu Arg Glu Phe Val Ala
1               5                   10

<210> SEQ ID NO 48
<211> LENGTH: 14
<212> TYPE: PRT
<213> ORGANISM: Artificial Sequence
<220> FEATURE:
<223> OTHER INFORMATION: Framework sequence

<400> SEQUENCE: 48

Trp Phe Arg Gln Ala Pro Gly Lys Gly Arg Glu Phe Val Ala
1               5                   10

<210> SEQ ID NO 49
<211> LENGTH: 17
<212> TYPE: PRT
<213> ORGANISM: Artificial Sequence
<220> FEATURE:
<223> OTHER INFORMATION: CDR sequence

<400> SEQUENCE: 49

Ala Ile Asn Trp Arg Gly Asp Ile Thr Ile Gly Pro Pro Asn Val Glu
1               5                   10                  15
Gly

<210> SEQ ID NO 50
<211> LENGTH: 17
<212> TYPE: PRT
<213> ORGANISM: Artificial Sequence
<220> FEATURE:
<223> OTHER INFORMATION: CDR sequence

<400> SEQUENCE: 50

Ala Ile Asn Trp Arg Asp Asp Ile Thr Ile Gly Pro Pro Asn Val Glu
1               5                   10                  15
Gly

<210> SEQ ID NO 51
<211> LENGTH: 32
<212> TYPE: PRT
<213> ORGANISM: Artificial Sequence
<220> FEATURE:
<223> OTHER INFORMATION: Framework sequence

<400> SEQUENCE: 51

Arg Phe Thr Ile Ser Arg Asp Asn Ala Lys Asn Thr Gly Tyr Leu Gln
1               5                   10                  15
Met Asn Ser Leu Ala Pro Asp Asp Thr Ala Val Tyr Tyr Cys Gly Ala
                20                  25                  30

<210> SEQ ID NO 52
<211> LENGTH: 32
<212> TYPE: PRT
<213> ORGANISM: Artificial Sequence
<220> FEATURE:
<223> OTHER INFORMATION: Framework sequence

<400> SEQUENCE: 52
```

Arg Phe Thr Ile Ser Arg Asp Asn Ala Lys Asn Thr Leu Tyr Leu Gln
1               5                   10                  15

Met Asn Ser Leu Ala Pro Glu Asp Thr Ala Val Tyr Tyr Cys Gly Ala
            20                  25                  30

<210> SEQ ID NO 53
<211> LENGTH: 32
<212> TYPE: PRT
<213> ORGANISM: Artificial Sequence
<220> FEATURE:
<223> OTHER INFORMATION: Framework sequence

<400> SEQUENCE: 53

Arg Phe Thr Ile Ser Arg Asp Asn Ser Lys Asn Thr Leu Tyr Leu Gln
1               5                   10                  15

Met Asn Ser Leu Ala Pro Glu Asp Thr Ala Val Tyr Tyr Cys Gly Ala
            20                  25                  30

<210> SEQ ID NO 54
<211> LENGTH: 32
<212> TYPE: PRT
<213> ORGANISM: Artificial Sequence
<220> FEATURE:
<223> OTHER INFORMATION: Framework sequence

<400> SEQUENCE: 54

Arg Phe Thr Ile Ser Arg Asp Asn Ser Lys Asn Thr Leu Tyr Leu Gln
1               5                   10                  15

Met Asn Ser Leu Arg Pro Glu Asp Thr Ala Val Tyr Tyr Cys Gly Ala
            20                  25                  30

<210> SEQ ID NO 55
<211> LENGTH: 32
<212> TYPE: PRT
<213> ORGANISM: Artificial Sequence
<220> FEATURE:
<223> OTHER INFORMATION: Framework sequence

<400> SEQUENCE: 55

Arg Phe Thr Ile Ser Arg Asp Asn Ser Lys Asn Thr Leu Tyr Leu Gln
1               5                   10                  15

Met Asn Ser Leu Arg Pro Asp Asp Thr Ala Val Tyr Tyr Cys Gly Ala
            20                  25                  30

<210> SEQ ID NO 56
<211> LENGTH: 32
<212> TYPE: PRT
<213> ORGANISM: Artificial Sequence
<220> FEATURE:
<223> OTHER INFORMATION: Framework sequence

<400> SEQUENCE: 56

Arg Phe Thr Ile Ser Arg Asp Asn Ala Lys Asn Thr Leu Tyr Leu Gln
1               5                   10                  15

Met Asn Ser Leu Arg Pro Glu Asp Thr Ala Val Tyr Tyr Cys Gly Ala
            20                  25                  30

<210> SEQ ID NO 57
<211> LENGTH: 32
<212> TYPE: PRT
<213> ORGANISM: Artificial Sequence
<220> FEATURE:
<223> OTHER INFORMATION: Framework sequence

<400> SEQUENCE: 57

-continued

Arg Phe Thr Ile Ser Arg Asp Asn Ala Lys Asn Thr Leu Tyr Leu Gln
1               5                   10                  15

Met Asn Ser Leu Ala Pro Asp Asp Thr Ala Val Tyr Tyr Cys Gly Ala
            20                  25                  30

<210> SEQ ID NO 58
<211> LENGTH: 32
<212> TYPE: PRT
<213> ORGANISM: Artificial Sequence
<220> FEATURE:
<223> OTHER INFORMATION: Framework sequence

<400> SEQUENCE: 58

Arg Phe Thr Ile Ser Arg Asp Asn Ala Lys Asn Thr Gly Tyr Leu Gln
1               5                   10                  15

Met Asn Ser Leu Ala Pro Glu Asp Thr Ala Val Tyr Tyr Cys Gly Ala
            20                  25                  30

<210> SEQ ID NO 59
<211> LENGTH: 32
<212> TYPE: PRT
<213> ORGANISM: Artificial Sequence
<220> FEATURE:
<223> OTHER INFORMATION: Framework sequence

<400> SEQUENCE: 59

Arg Phe Thr Ile Ser Arg Asp Asn Ala Lys Asn Thr Gly Tyr Leu Gln
1               5                   10                  15

Met Asn Ser Leu Arg Pro Asp Asp Thr Ala Val Tyr Tyr Cys Gly Ala
            20                  25                  30

<210> SEQ ID NO 60
<211> LENGTH: 32
<212> TYPE: PRT
<213> ORGANISM: Artificial Sequence
<220> FEATURE:
<223> OTHER INFORMATION: Framework sequence

<400> SEQUENCE: 60

Arg Phe Thr Ile Ser Arg Asp Asn Ala Lys Asn Thr Gly Tyr Leu Gln
1               5                   10                  15

Met Asn Ser Leu Arg Pro Glu Asp Thr Ala Val Tyr Tyr Cys Gly Ala
            20                  25                  30

<210> SEQ ID NO 61
<211> LENGTH: 17
<212> TYPE: PRT
<213> ORGANISM: Artificial Sequence
<220> FEATURE:
<223> OTHER INFORMATION: CDR sequence

<400> SEQUENCE: 61

Gly Thr Pro Leu Asn Pro Gly Ala Tyr Ile Tyr Asp Trp Ser Tyr Asp
1               5                   10                  15

Tyr

<210> SEQ ID NO 62
<211> LENGTH: 11
<212> TYPE: PRT
<213> ORGANISM: Artificial Sequence
<220> FEATURE:
<223> OTHER INFORMATION: Framework sequence

<400> SEQUENCE: 62

Trp Gly Arg Gly Thr Gln Val Thr Val Ser Ser
1               5                   10

<210> SEQ ID NO 63
<211> LENGTH: 11
<212> TYPE: PRT
<213> ORGANISM: Artificial Sequence
<220> FEATURE:
<223> OTHER INFORMATION: Framework sequence

<400> SEQUENCE: 63

Trp Gly Gln Gly Thr Leu Val Thr Val Ser Ser
1               5                   10

<210> SEQ ID NO 64
<211> LENGTH: 11
<212> TYPE: PRT
<213> ORGANISM: Artificial Sequence
<220> FEATURE:
<223> OTHER INFORMATION: Framework sequence

<400> SEQUENCE: 64

Trp Gly Arg Gly Thr Leu Val Thr Val Ser Ser
1               5                   10

<210> SEQ ID NO 65
<211> LENGTH: 408
<212> TYPE: PRT
<213> ORGANISM: Artificial Sequence
<220> FEATURE:
<223> OTHER INFORMATION: Nanobody sequence

<400> SEQUENCE: 65

Glu Val Gln Leu Val Glu Ser Gly Gly Gly Leu Val Gln Ala Gly Gly
1               5                   10                  15

Ser Leu Ser Ile Ser Cys Ala Ala Ser Gly Gly Ser Leu Ser Asn Tyr
            20                  25                  30

Val Leu Gly Trp Phe Arg Gln Ala Pro Gly Lys Glu Arg Glu Phe Val
        35                  40                  45

Ala Ala Ile Asn Trp Arg Gly Asp Ile Thr Ile Gly Pro Pro Asn Val
    50                  55                  60

Glu Gly Arg Phe Thr Ile Ser Arg Asp Asn Ala Lys Asn Thr Gly Tyr
65                  70                  75                  80

Leu Gln Met Asn Ser Leu Ala Pro Asp Thr Ala Val Tyr Tyr Cys
                85                  90                  95

Gly Ala Gly Thr Pro Leu Asn Pro Gly Ala Tyr Ile Tyr Asp Trp Ser
            100                 105                 110

Tyr Asp Tyr Trp Gly Arg Gly Thr Gln Val Thr Val Ser Ser Gly Gly
        115                 120                 125

Gly Gly Ser Gly Gly Gly Gly Ser Gly Gly Gly Ser Glu Val Gln
            130                 135                 140

Leu Val Glu Ser Gly Gly Gly Leu Val Gln Ala Gly Gly Ser Leu Ser
145                 150                 155                 160

Ile Ser Cys Ala Ala Ser Gly Gly Ser Leu Ser Asn Tyr Val Leu Gly
                165                 170                 175

Trp Phe Arg Gln Ala Pro Gly Lys Glu Arg Glu Phe Val Ala Ala Ile
            180                 185                 190

Asn Trp Arg Gly Asp Ile Thr Ile Gly Pro Pro Asn Val Glu Gly Arg
        195                 200                 205

```
Phe Thr Ile Ser Arg Asp Asn Ala Lys Asn Thr Gly Tyr Leu Gln Met
    210                 215                 220

Asn Ser Leu Ala Pro Asp Asp Thr Ala Val Tyr Tyr Cys Gly Ala Gly
225                 230                 235                 240

Thr Pro Leu Asn Pro Gly Ala Tyr Ile Tyr Asp Trp Ser Tyr Asp Tyr
                245                 250                 255

Trp Gly Arg Gly Thr Gln Val Thr Val Ser Ser Gly Gly Gly Gly Ser
                260                 265                 270

Gly Gly Gly Gly Ser Gly Gly Gly Ser Glu Val Gln Leu Val Glu
            275                 280                 285

Ser Gly Gly Gly Leu Val Gln Ala Gly Gly Ser Leu Ser Ile Ser Cys
290                 295                 300

Ala Ala Ser Gly Gly Ser Leu Ser Asn Tyr Val Leu Gly Trp Phe Arg
305                 310                 315                 320

Gln Ala Pro Gly Lys Glu Arg Glu Phe Val Ala Ala Ile Asn Trp Arg
                325                 330                 335

Gly Asp Ile Thr Ile Gly Pro Pro Asn Val Glu Gly Arg Phe Thr Ile
                340                 345                 350

Ser Arg Asp Asn Ala Lys Asn Thr Gly Tyr Leu Gln Met Asn Ser Leu
            355                 360                 365

Ala Pro Asp Asp Thr Ala Val Tyr Tyr Cys Gly Ala Gly Thr Pro Leu
370                 375                 380

Asn Pro Gly Ala Tyr Ile Tyr Asp Trp Ser Tyr Asp Tyr Trp Gly Arg
385                 390                 395                 400

Gly Thr Gln Val Thr Val Ser Ser
                405

<210> SEQ ID NO 66
<211> LENGTH: 384
<212> TYPE: PRT
<213> ORGANISM: Artificial Sequence
<220> FEATURE:
<223> OTHER INFORMATION: Nanobody sequence

<400> SEQUENCE: 66

Glu Val Gln Leu Val Glu Ser Gly Gly Gly Leu Val Gln Ala Gly Gly
1               5                   10                  15

Ser Leu Ser Ile Ser Cys Ala Ala Ser Gly Gly Ser Leu Ser Asn Tyr
            20                  25                  30

Val Leu Gly Trp Phe Arg Gln Ala Pro Gly Lys Glu Arg Glu Phe Val
        35                  40                  45

Ala Ala Ile Asn Trp Arg Gly Asp Ile Thr Ile Gly Pro Pro Asn Val
    50                  55                  60

Glu Gly Arg Phe Thr Ile Ser Arg Asp Asn Ala Lys Asn Thr Gly Tyr
65                  70                  75                  80

Leu Gln Met Asn Ser Leu Ala Pro Asp Asp Thr Ala Val Tyr Tyr Cys
                85                  90                  95

Gly Ala Gly Thr Pro Leu Asn Pro Gly Ala Tyr Ile Tyr Asp Trp Ser
            100                 105                 110

Tyr Asp Tyr Trp Gly Arg Gly Thr Gln Val Thr Val Ser Ser Ala Ala
        115                 120                 125

Ala Glu Val Gln Leu Val Glu Ser Gly Gly Gly Leu Val Gln Ala Gly
    130                 135                 140

Gly Ser Leu Ser Ile Ser Cys Ala Ala Ser Gly Gly Ser Leu Ser Asn
145                 150                 155                 160
```

Tyr Val Leu Gly Trp Phe Arg Gln Ala Pro Gly Lys Glu Arg Glu Phe
                165                 170                 175

Val Ala Ala Ile Asn Trp Arg Gly Asp Ile Thr Ile Gly Pro Pro Asn
            180                 185                 190

Val Glu Gly Arg Phe Thr Ile Ser Arg Asp Asn Ala Lys Asn Thr Gly
        195                 200                 205

Tyr Leu Gln Met Asn Ser Leu Ala Pro Asp Asp Thr Ala Val Tyr Tyr
    210                 215                 220

Cys Gly Ala Gly Thr Pro Leu Asn Pro Gly Ala Tyr Ile Tyr Asp Trp
225                 230                 235                 240

Ser Tyr Asp Tyr Trp Gly Arg Gly Thr Gln Val Thr Val Ser Ser Ala
            245                 250                 255

Ala Ala Glu Val Gln Leu Val Glu Ser Gly Gly Gly Leu Val Gln Ala
                260                 265                 270

Gly Gly Ser Leu Ser Ile Ser Cys Ala Ala Ser Gly Gly Ser Leu Ser
            275                 280                 285

Asn Tyr Val Leu Gly Trp Phe Arg Gln Ala Pro Gly Lys Glu Arg Glu
        290                 295                 300

Phe Val Ala Ala Ile Asn Trp Arg Gly Asp Ile Thr Ile Gly Pro Pro
305                 310                 315                 320

Asn Val Glu Gly Arg Phe Thr Ile Ser Arg Asp Asn Ala Lys Asn Thr
                325                 330                 335

Gly Tyr Leu Gln Met Asn Ser Leu Ala Pro Asp Asp Thr Ala Val Tyr
            340                 345                 350

Tyr Cys Gly Ala Gly Thr Pro Leu Asn Pro Gly Ala Tyr Ile Tyr Asp
        355                 360                 365

Trp Ser Tyr Asp Tyr Trp Gly Arg Gly Thr Gln Val Thr Val Ser Ser
    370                 375                 380

<210> SEQ ID NO 67
<211> LENGTH: 396
<212> TYPE: PRT
<213> ORGANISM: Artificial Sequence
<220> FEATURE:
<223> OTHER INFORMATION: Nanobody sequence

<400> SEQUENCE: 67

Glu Val Gln Leu Val Glu Ser Gly Gly Gly Leu Val Gln Ala Gly Gly
1               5                   10                  15

Ser Leu Ser Ile Ser Cys Ala Ala Ser Gly Gly Ser Leu Ser Asn Tyr
            20                  25                  30

Val Leu Gly Trp Phe Arg Gln Ala Pro Gly Lys Glu Arg Glu Phe Val
        35                  40                  45

Ala Ala Ile Asn Trp Arg Gly Asp Ile Thr Ile Gly Pro Pro Asn Val
    50                  55                  60

Glu Gly Arg Phe Thr Ile Ser Arg Asp Asn Ala Lys Asn Thr Gly Tyr
65                  70                  75                  80

Leu Gln Met Asn Ser Leu Ala Pro Asp Asp Thr Ala Val Tyr Tyr Cys
                85                  90                  95

Gly Ala Gly Thr Pro Leu Asn Pro Gly Ala Tyr Ile Tyr Asp Trp Ser
            100                 105                 110

Tyr Asp Tyr Trp Gly Arg Gly Thr Gln Val Thr Val Ser Ser Gly Gly
        115                 120                 125

Gly Gly Ser Gly Gly Gly Ser Glu Val Gln Leu Val Glu Ser Gly Gly
    130                 135                 140

```
Gly Leu Val Gln Ala Gly Ser Leu Ser Ile Ser Cys Ala Ala Ser
145                 150                 155                 160

Gly Gly Ser Leu Ser Asn Tyr Val Leu Gly Trp Phe Arg Gln Ala Pro
            165                 170                 175

Gly Lys Glu Arg Glu Phe Val Ala Ala Ile Asn Trp Arg Gly Asp Ile
            180                 185                 190

Thr Ile Gly Pro Pro Asn Val Glu Gly Arg Phe Thr Ile Ser Arg Asp
        195                 200                 205

Asn Ala Lys Asn Thr Gly Tyr Leu Gln Met Asn Ser Leu Ala Pro Asp
    210                 215                 220

Asp Thr Ala Val Tyr Tyr Cys Gly Ala Gly Thr Pro Leu Asn Pro Gly
225                 230                 235                 240

Ala Tyr Ile Tyr Asp Trp Ser Tyr Asp Tyr Trp Gly Arg Gly Thr Gln
            245                 250                 255

Val Thr Val Ser Ser Gly Gly Gly Ser Gly Gly Gly Ser Glu Val
            260                 265                 270

Gln Leu Val Glu Ser Gly Gly Gly Leu Val Gln Ala Gly Gly Ser Leu
        275                 280                 285

Ser Ile Ser Cys Ala Ala Ser Gly Gly Ser Leu Ser Asn Tyr Val Leu
    290                 295                 300

Gly Trp Phe Arg Gln Ala Pro Gly Lys Glu Arg Glu Phe Val Ala Ala
305                 310                 315                 320

Ile Asn Trp Arg Gly Asp Ile Thr Ile Gly Pro Pro Asn Val Glu Gly
            325                 330                 335

Arg Phe Thr Ile Ser Arg Asp Asn Ala Lys Asn Thr Gly Tyr Leu Gln
            340                 345                 350

Met Asn Ser Leu Ala Pro Asp Asp Thr Ala Val Tyr Tyr Cys Gly Ala
        355                 360                 365

Gly Thr Pro Leu Asn Pro Gly Ala Tyr Ile Tyr Asp Trp Ser Tyr Asp
    370                 375                 380

Tyr Trp Gly Arg Gly Thr Gln Val Thr Val Ser Ser
385                 390                 395
```

<210> SEQ ID NO 68
<211> LENGTH: 418
<212> TYPE: PRT
<213> ORGANISM: Artificial Sequence
<220> FEATURE:
<223> OTHER INFORMATION: Nanobody sequence

<400> SEQUENCE: 68

```
Glu Val Gln Leu Val Glu Ser Gly Gly Gly Leu Val Gln Ala Gly Gly
1               5                   10                  15

Ser Leu Ser Ile Ser Cys Ala Ala Ser Gly Gly Ser Leu Ser Asn Tyr
            20                  25                  30

Val Leu Gly Trp Phe Arg Gln Ala Pro Gly Lys Glu Arg Glu Phe Val
        35                  40                  45

Ala Ala Ile Asn Trp Arg Gly Asp Ile Thr Ile Gly Pro Pro Asn Val
    50                  55                  60

Glu Gly Arg Phe Thr Ile Ser Arg Asp Asn Ala Lys Asn Thr Gly Tyr
65                  70                  75                  80

Leu Gln Met Asn Ser Leu Ala Pro Asp Asp Thr Ala Val Tyr Tyr Cys
                85                  90                  95

Gly Ala Gly Thr Pro Leu Asn Pro Gly Ala Tyr Ile Tyr Asp Trp Ser
            100                 105                 110
```

Tyr Asp Tyr Trp Gly Arg Gly Thr Gln Val Thr Val Ser Ser Gly Gly
            115                 120                 125

Gly Gly Ser Gly Gly Gly Ser Gly Gly Gly Ser Gly Gly Gly
        130                 135                 140

Gly Ser Glu Val Gln Leu Val Glu Ser Gly Gly Gly Leu Val Gln Ala
145                 150                 155                 160

Gly Gly Ser Leu Ser Ile Ser Cys Ala Ala Ser Gly Gly Ser Leu Ser
                165                 170                 175

Asn Tyr Val Leu Gly Trp Phe Arg Gln Ala Pro Gly Lys Glu Arg Glu
            180                 185                 190

Phe Val Ala Ala Ile Asn Trp Arg Gly Asp Ile Thr Ile Gly Pro Pro
        195                 200                 205

Asn Val Glu Gly Arg Phe Thr Ile Ser Arg Asp Asn Ala Lys Asn Thr
    210                 215                 220

Gly Tyr Leu Gln Met Asn Ser Leu Ala Pro Asp Asp Thr Ala Val Tyr
225                 230                 235                 240

Tyr Cys Gly Ala Gly Thr Pro Leu Asn Pro Gly Ala Tyr Ile Tyr Asp
                245                 250                 255

Trp Ser Tyr Asp Tyr Trp Gly Arg Gly Thr Gln Val Thr Val Ser Ser
            260                 265                 270

Gly Gly Gly Gly Ser Gly Gly Gly Ser Gly Gly Gly Gly Ser Gly
        275                 280                 285

Gly Gly Gly Ser Glu Val Gln Leu Val Glu Ser Gly Gly Gly Leu Val
    290                 295                 300

Gln Ala Gly Gly Ser Leu Ser Ile Ser Cys Ala Ala Ser Gly Gly Ser
305                 310                 315                 320

Leu Ser Asn Tyr Val Leu Gly Trp Phe Arg Gln Ala Pro Gly Lys Glu
                325                 330                 335

Arg Glu Phe Val Ala Ala Ile Asn Trp Arg Gly Asp Ile Thr Ile Gly
            340                 345                 350

Pro Pro Asn Val Glu Gly Arg Phe Thr Ile Ser Arg Asp Asn Ala Lys
        355                 360                 365

Asn Thr Gly Tyr Leu Gln Met Asn Ser Leu Ala Pro Asp Asp Thr Ala
    370                 375                 380

Val Tyr Tyr Cys Gly Ala Gly Thr Pro Leu Asn Pro Gly Ala Tyr Ile
385                 390                 395                 400

Tyr Asp Trp Ser Tyr Asp Tyr Trp Gly Arg Gly Thr Gln Val Thr Val
                405                 410                 415

Ser Ser

<210> SEQ ID NO 69
<211> LENGTH: 408
<212> TYPE: PRT
<213> ORGANISM: Artificial Sequence
<220> FEATURE:
<223> OTHER INFORMATION: Nanobody sequence

<400> SEQUENCE: 69

Glu Val Gln Leu Val Glu Ser Gly Gly Gly Leu Val Gln Ala Gly Gly
1               5                   10                  15

Ser Leu Ser Ile Ser Cys Ala Ala Ser Gly Gly Ser Leu Ser Asn Tyr
                20                  25                  30

Val Leu Gly Trp Phe Arg Gln Ala Pro Gly Lys Glu Arg Glu Phe Val
            35                  40                  45

Ala Ala Ile Asn Trp Arg Gly Asp Ile Thr Ile Gly Pro Pro Asn Val

```
            50                  55                  60
Glu Gly Arg Phe Thr Ile Ser Arg Asp Asn Ala Lys Asn Thr Gly Tyr
 65                  70                  75                  80

Leu Gln Met Asn Ser Leu Ala Pro Asp Asp Thr Ala Val Tyr Tyr Cys
                 85                  90                  95

Gly Ala Gly Thr Pro Leu Asn Pro Gly Ala Tyr Ile Tyr Asp Trp Ser
            100                 105                 110

Tyr Asp Tyr Trp Gly Arg Gly Thr Gln Val Thr Val Ser Ser Gly Gly
        115                 120                 125

Gly Gly Ser Gly Gly Gly Ser Gly Gly Gly Ser Glu Val Gln
    130                 135                 140

Leu Val Glu Ser Gly Gly Gly Leu Val Gln Ala Gly Gly Ser Leu Ser
145                 150                 155                 160

Ile Ser Cys Ala Ala Ser Gly Gly Ser Leu Ser Asn Tyr Val Leu Gly
                165                 170                 175

Trp Phe Arg Gln Ala Pro Gly Lys Glu Arg Glu Phe Val Ala Ala Ile
            180                 185                 190

Asn Trp Arg Gly Asp Ile Thr Ile Gly Pro Pro Asn Val Glu Gly Arg
        195                 200                 205

Phe Thr Ile Ser Arg Asp Asn Ala Lys Asn Thr Gly Tyr Leu Gln Met
    210                 215                 220

Asn Ser Leu Ala Pro Asp Asp Thr Ala Val Tyr Tyr Cys Gly Ala Gly
225                 230                 235                 240

Thr Pro Leu Asn Pro Gly Ala Tyr Ile Tyr Asp Trp Ser Tyr Asp Tyr
                245                 250                 255

Trp Gly Arg Gly Thr Gln Val Thr Val Ser Ser Gly Gly Gly Gly Ser
            260                 265                 270

Gly Gly Gly Gly Ser Gly Gly Gly Ser Glu Val Gln Leu Val Glu
        275                 280                 285

Ser Gly Gly Gly Leu Val Gln Pro Gly Gly Ser Leu Arg Leu Ser Cys
    290                 295                 300

Ala Ala Ser Gly Leu Thr Leu Asp Tyr Tyr Ala Leu Gly Trp Phe Arg
305                 310                 315                 320

Gln Ala Pro Gly Lys Glu Arg Glu Gly Val Ser Cys Ile Ser Ser Ser
                325                 330                 335

Asp His Ser Thr Thr Tyr Thr Asp Ser Val Lys Gly Arg Phe Thr Ile
            340                 345                 350

Ser Trp Asp Asn Ala Lys Asn Thr Leu Tyr Leu Gln Met Asn Ser Leu
        355                 360                 365

Lys Pro Gly Asp Thr Ala Val Tyr Tyr Cys Ala Ala Asp Pro Ala Leu
    370                 375                 380

Gly Cys Tyr Ser Gly Ser Tyr Tyr Pro Arg Tyr Asp Tyr Trp Gly Gln
385                 390                 395                 400

Gly Thr Gln Val Thr Val Ser Ser
                405
```

<210> SEQ ID NO 70
<211> LENGTH: 408
<212> TYPE: PRT
<213> ORGANISM: Artificial Sequence
<220> FEATURE:
<223> OTHER INFORMATION: Nanobody sequence

<400> SEQUENCE: 70

Glu Val Gln Leu Val Glu Ser Gly Gly Gly Leu Val Gln Ala Gly Gly

```
            1               5                   10                  15
        Ser Leu Ser Ile Ser Cys Ala Ala Ser Gly Gly Ser Leu Ser Asn Tyr
                        20                  25                  30

Val Leu Gly Trp Phe Arg Gln Ala Pro Gly Lys Glu Arg Glu Phe Val
                        35                  40                  45

Ala Ala Ile Asn Trp Arg Gly Asp Ile Thr Ile Gly Pro Pro Asn Val
                50                  55                  60

Glu Gly Arg Phe Thr Ile Ser Arg Asp Asn Ala Lys Asn Thr Gly Tyr
        65                  70                  75                  80

Leu Gln Met Asn Ser Leu Ala Pro Asp Thr Ala Val Tyr Tyr Cys
                        85                  90                  95

Gly Ala Gly Thr Pro Leu Asn Pro Gly Ala Tyr Ile Tyr Asp Trp Ser
                        100                 105                 110

Tyr Asp Tyr Trp Gly Arg Gly Thr Gln Val Thr Val Ser Ser Gly Gly
                        115                 120                 125

Gly Gly Ser Gly Gly Gly Ser Gly Gly Gly Ser Glu Val Gln
                        130                 135                 140

Leu Val Glu Ser Gly Gly Gly Leu Val Gln Pro Gly Gly Ser Leu Arg
        145                 150                 155                 160

Leu Ser Cys Ala Ala Ser Gly Leu Thr Leu Asp Tyr Tyr Ala Leu Gly
                        165                 170                 175

Trp Phe Arg Gln Ala Pro Gly Lys Glu Arg Glu Gly Val Ser Cys Ile
                        180                 185                 190

Ser Ser Ser Asp His Ser Thr Thr Tyr Thr Asp Ser Val Lys Gly Arg
                        195                 200                 205

Phe Thr Ile Ser Trp Asp Asn Ala Lys Asn Thr Leu Tyr Leu Gln Met
                210                 215                 220

Asn Ser Leu Lys Pro Gly Asp Thr Ala Val Tyr Tyr Cys Ala Ala Asp
        225                 230                 235                 240

Pro Ala Leu Gly Cys Tyr Ser Gly Ser Tyr Tyr Pro Arg Tyr Asp Tyr
                        245                 250                 255

Trp Gly Gln Gly Thr Gln Val Thr Val Ser Ser Gly Gly Gly Gly Ser
                        260                 265                 270

Gly Gly Gly Gly Ser Gly Gly Gly Ser Glu Val Gln Leu Val Glu
                        275                 280                 285

Ser Gly Gly Gly Leu Val Gln Ala Gly Gly Ser Leu Ser Ile Ser Cys
                        290                 295                 300

Ala Ala Ser Gly Gly Ser Leu Ser Asn Tyr Val Leu Gly Trp Phe Arg
        305                 310                 315                 320

Gln Ala Pro Gly Lys Glu Arg Glu Phe Val Ala Ala Ile Asn Trp Arg
                        325                 330                 335

Gly Asp Ile Thr Ile Gly Pro Pro Asn Val Glu Gly Arg Phe Thr Ile
                        340                 345                 350

Ser Arg Asp Asn Ala Lys Asn Thr Gly Tyr Leu Gln Met Asn Ser Leu
                        355                 360                 365

Ala Pro Asp Asp Thr Ala Val Tyr Tyr Cys Gly Ala Gly Thr Pro Leu
        370                 375                 380

Asn Pro Gly Ala Tyr Ile Tyr Asp Trp Ser Tyr Asp Tyr Trp Gly Arg
        385                 390                 395                 400

Gly Thr Gln Val Thr Val Ser Ser
                        405

<210> SEQ ID NO 71
```

<211> LENGTH: 408
<212> TYPE: PRT
<213> ORGANISM: Artificial Sequence
<220> FEATURE:
<223> OTHER INFORMATION: Nanobody sequence

<400> SEQUENCE: 71

```
Asp Val Gln Leu Val Glu Ser Gly Gly Gly Leu Val Gln Ala Gly Gly
1               5                   10                  15

Ser Leu Ser Ile Ser Cys Ala Ala Ser Gly Gly Ser Leu Ser Asn Tyr
            20                  25                  30

Val Leu Gly Trp Phe Arg Gln Ala Pro Gly Lys Glu Arg Glu Phe Val
        35                  40                  45

Ala Ala Ile Asn Trp Arg Gly Asp Ile Thr Ile Gly Pro Pro Asn Val
50                  55                  60

Glu Gly Arg Phe Thr Ile Ser Arg Asp Asn Ala Lys Asn Thr Gly Tyr
65                  70                  75                  80

Leu Gln Met Asn Ser Leu Ala Pro Asp Asp Thr Ala Val Tyr Tyr Cys
                85                  90                  95

Gly Ala Gly Thr Pro Leu Asn Pro Gly Ala Tyr Ile Tyr Asp Trp Ser
            100                 105                 110

Tyr Asp Tyr Trp Gly Arg Gly Thr Gln Val Thr Val Ser Ser Gly Gly
        115                 120                 125

Gly Gly Ser Gly Gly Gly Ser Gly Gly Gly Ser Glu Val Gln
130                 135                 140

Leu Val Glu Ser Gly Gly Gly Leu Val Gln Ala Gly Gly Ser Leu Ser
145                 150                 155                 160

Ile Ser Cys Ala Ala Ser Gly Gly Ser Leu Ser Asn Tyr Val Leu Gly
            165                 170                 175

Trp Phe Arg Gln Ala Pro Gly Lys Glu Arg Glu Phe Val Ala Ala Ile
        180                 185                 190

Asn Trp Arg Gly Asp Ile Thr Ile Gly Pro Pro Asn Val Glu Gly Arg
    195                 200                 205

Phe Thr Ile Ser Arg Asp Asn Ala Lys Asn Thr Gly Tyr Leu Gln Met
210                 215                 220

Asn Ser Leu Ala Pro Asp Asp Thr Ala Val Tyr Tyr Cys Gly Ala Gly
225                 230                 235                 240

Thr Pro Leu Asn Pro Gly Ala Tyr Ile Tyr Asp Trp Ser Tyr Asp Tyr
            245                 250                 255

Trp Gly Arg Gly Thr Gln Val Thr Val Ser Ser Gly Gly Gly Gly Ser
        260                 265                 270

Gly Gly Gly Gly Ser Gly Gly Gly Ser Glu Val Gln Leu Val Glu
    275                 280                 285

Ser Gly Gly Gly Leu Val Gln Ala Gly Gly Ser Leu Ser Ile Ser Cys
290                 295                 300

Ala Ala Ser Gly Gly Ser Leu Ser Asn Tyr Val Leu Gly Trp Phe Arg
305                 310                 315                 320

Gln Ala Pro Gly Lys Glu Arg Glu Phe Val Ala Ala Ile Asn Trp Arg
            325                 330                 335

Gly Asp Ile Thr Ile Gly Pro Pro Asn Val Glu Gly Arg Phe Thr Ile
        340                 345                 350

Ser Arg Asp Asn Ala Lys Asn Thr Gly Tyr Leu Gln Met Asn Ser Leu
    355                 360                 365

Ala Pro Asp Asp Thr Ala Val Tyr Tyr Cys Gly Ala Gly Thr Pro Leu
370                 375                 380
```

Asn Pro Gly Ala Tyr Ile Tyr Asp Trp Ser Tyr Asp Tyr Trp Gly Arg
385                 390                 395                 400

Gly Thr Gln Val Thr Val Ser Ser
            405

<210> SEQ ID NO 72
<211> LENGTH: 408
<212> TYPE: PRT
<213> ORGANISM: Artificial Sequence
<220> FEATURE:
<223> OTHER INFORMATION: Nanobody sequence

<400> SEQUENCE: 72

Glu Val Gln Leu Leu Glu Ser Gly Gly Gly Leu Val Gln Pro Gly Gly
1               5                   10                  15

Ser Leu Arg Ile Ser Cys Ala Ala Ser Gly Gly Ser Leu Ser Asn Tyr
            20                  25                  30

Val Leu Gly Trp Phe Arg Gln Ala Pro Gly Lys Gly Arg Glu Phe Val
        35                  40                  45

Ala Ala Ile Asn Trp Arg Gly Asp Ile Thr Ile Gly Pro Pro Asn Val
    50                  55                  60

Glu Gly Arg Phe Thr Ile Ser Arg Asp Asn Ser Lys Asn Thr Leu Tyr
65                  70                  75                  80

Leu Gln Met Asn Ser Leu Arg Pro Glu Asp Thr Ala Val Tyr Tyr Cys
                85                  90                  95

Gly Ala Gly Thr Pro Leu Asn Pro Gly Ala Tyr Ile Tyr Asp Trp Ser
            100                 105                 110

Tyr Asp Tyr Trp Gly Gln Gly Thr Leu Val Thr Val Ser Ser Gly Gly
        115                 120                 125

Gly Gly Ser Gly Gly Gly Ser Gly Gly Gly Ser Glu Val Gln
    130                 135                 140

Leu Leu Glu Ser Gly Gly Gly Leu Val Gln Pro Gly Gly Ser Leu Arg
145                 150                 155                 160

Ile Ser Cys Ala Ala Ser Gly Gly Ser Leu Ser Asn Tyr Val Leu Gly
                165                 170                 175

Trp Phe Arg Gln Ala Pro Gly Lys Gly Arg Glu Phe Val Ala Ala Ile
            180                 185                 190

Asn Trp Arg Gly Asp Ile Thr Ile Gly Pro Pro Asn Val Glu Gly Arg
        195                 200                 205

Phe Thr Ile Ser Arg Asp Asn Ser Lys Asn Thr Leu Tyr Leu Gln Met
    210                 215                 220

Asn Ser Leu Arg Pro Glu Asp Thr Ala Val Tyr Tyr Cys Gly Ala Gly
225                 230                 235                 240

Thr Pro Leu Asn Pro Gly Ala Tyr Ile Tyr Asp Trp Ser Tyr Asp Tyr
                245                 250                 255

Trp Gly Gln Gly Thr Leu Val Thr Val Ser Ser Gly Gly Gly Gly Ser
            260                 265                 270

Gly Gly Gly Gly Ser Gly Gly Gly Ser Glu Val Gln Leu Leu Glu
        275                 280                 285

Ser Gly Gly Gly Leu Val Gln Pro Gly Gly Ser Leu Arg Ile Ser Cys
    290                 295                 300

Ala Ala Ser Gly Gly Ser Leu Ser Asn Tyr Val Leu Gly Trp Phe Arg
305                 310                 315                 320

Gln Ala Pro Gly Lys Gly Arg Glu Phe Val Ala Ala Ile Asn Trp Arg
                325                 330                 335

```
Gly Asp Ile Thr Ile Gly Pro Pro Asn Val Glu Gly Arg Phe Thr Ile
            340                 345                 350

Ser Arg Asp Asn Ser Lys Asn Thr Leu Tyr Leu Gln Met Asn Ser Leu
            355                 360                 365

Arg Pro Glu Asp Thr Ala Val Tyr Tyr Cys Gly Ala Gly Thr Pro Leu
370                 375                 380

Asn Pro Gly Ala Tyr Ile Tyr Asp Trp Ser Tyr Asp Tyr Trp Gly Gln
385                 390                 395                 400

Gly Thr Leu Val Thr Val Ser Ser
                405

<210> SEQ ID NO 73
<211> LENGTH: 408
<212> TYPE: PRT
<213> ORGANISM: Artificial Sequence
<220> FEATURE:
<223> OTHER INFORMATION: Nanobody sequence

<400> SEQUENCE: 73

Asp Val Gln Leu Leu Glu Ser Gly Gly Gly Leu Val Gln Pro Gly Gly
1               5                   10                  15

Ser Leu Arg Ile Ser Cys Ala Ala Ser Gly Gly Ser Leu Ser Asn Tyr
            20                  25                  30

Val Leu Gly Trp Phe Arg Gln Ala Pro Gly Lys Gly Arg Glu Phe Val
        35                  40                  45

Ala Ala Ile Asn Trp Arg Gly Asp Ile Thr Ile Gly Pro Pro Asn Val
    50                  55                  60

Glu Gly Arg Phe Thr Ile Ser Arg Asp Asn Ser Lys Asn Thr Leu Tyr
65                  70                  75                  80

Leu Gln Met Asn Ser Leu Arg Pro Glu Asp Thr Ala Val Tyr Tyr Cys
                85                  90                  95

Gly Ala Gly Thr Pro Leu Asn Pro Gly Ala Tyr Ile Tyr Asp Trp Ser
            100                 105                 110

Tyr Asp Tyr Trp Gly Gln Gly Thr Leu Val Thr Val Ser Ser Gly Gly
        115                 120                 125

Gly Gly Ser Gly Gly Gly Ser Gly Gly Gly Ser Glu Val Gln
    130                 135                 140

Leu Leu Glu Ser Gly Gly Gly Leu Val Gln Pro Gly Gly Ser Leu Arg
145                 150                 155                 160

Ile Ser Cys Ala Ala Ser Gly Gly Ser Leu Ser Asn Tyr Val Leu Gly
                165                 170                 175

Trp Phe Arg Gln Ala Pro Gly Lys Gly Arg Glu Phe Val Ala Ala Ile
            180                 185                 190

Asn Trp Arg Gly Asp Ile Thr Ile Gly Pro Pro Asn Val Glu Gly Arg
        195                 200                 205

Phe Thr Ile Ser Arg Asp Asn Ser Lys Asn Thr Leu Tyr Leu Gln Met
    210                 215                 220

Asn Ser Leu Arg Pro Glu Asp Thr Ala Val Tyr Tyr Cys Gly Ala Gly
225                 230                 235                 240

Thr Pro Leu Asn Pro Gly Ala Tyr Ile Tyr Asp Trp Ser Tyr Asp Tyr
                245                 250                 255

Trp Gly Gln Gly Thr Leu Val Thr Val Ser Ser Gly Gly Gly Gly Ser
            260                 265                 270

Gly Gly Gly Gly Ser Gly Gly Gly Ser Glu Val Gln Leu Leu Glu
        275                 280                 285
```

```
Ser Gly Gly Gly Leu Val Gln Pro Gly Gly Ser Leu Arg Ile Ser Cys
    290                 295                 300

Ala Ala Ser Gly Gly Ser Leu Ser Asn Tyr Val Leu Gly Trp Phe Arg
305                 310                 315                 320

Gln Ala Pro Gly Lys Gly Arg Glu Phe Val Ala Ala Ile Asn Trp Arg
                325                 330                 335

Gly Asp Ile Thr Ile Gly Pro Pro Asn Val Glu Gly Arg Phe Thr Ile
                340                 345                 350

Ser Arg Asp Asn Ser Lys Asn Thr Leu Tyr Leu Gln Met Asn Ser Leu
                355                 360                 365

Arg Pro Glu Asp Thr Ala Val Tyr Tyr Cys Gly Ala Gly Thr Pro Leu
    370                 375                 380

Asn Pro Gly Ala Tyr Ile Tyr Asp Trp Ser Tyr Asp Tyr Trp Gly Gln
385                 390                 395                 400

Gly Thr Leu Val Thr Val Ser Ser
                405

<210> SEQ ID NO 74
<211> LENGTH: 408
<212> TYPE: PRT
<213> ORGANISM: Artificial Sequence
<220> FEATURE:
<223> OTHER INFORMATION: Nanobody sequence

<400> SEQUENCE: 74

Glu Val Gln Leu Leu Glu Ser Gly Gly Gly Leu Val Gln Pro Gly Gly
1               5                   10                  15

Ser Leu Arg Leu Ser Cys Ala Ala Ser Gly Gly Ser Leu Ser Asn Tyr
                20                  25                  30

Val Leu Gly Trp Phe Arg Gln Ala Pro Gly Lys Gly Arg Glu Phe Val
            35                  40                  45

Ala Ala Ile Asn Trp Arg Asp Asp Ile Thr Ile Gly Pro Pro Asn Val
        50                  55                  60

Glu Gly Arg Phe Thr Ile Ser Arg Asp Asn Ala Lys Asn Thr Leu Tyr
65                  70                  75                  80

Leu Gln Met Asn Ser Leu Arg Pro Glu Asp Thr Ala Val Tyr Tyr Cys
                85                  90                  95

Gly Ala Gly Thr Pro Leu Asn Pro Gly Ala Tyr Ile Tyr Asp Trp Ser
            100                 105                 110

Tyr Asp Tyr Trp Gly Gln Gly Thr Leu Val Thr Val Ser Ser Gly Gly
        115                 120                 125

Gly Gly Ser Gly Gly Gly Gly Ser Gly Gly Gly Gly Ser Glu Val Gln
    130                 135                 140

Leu Leu Glu Ser Gly Gly Gly Leu Val Gln Pro Gly Gly Ser Leu Arg
145                 150                 155                 160

Leu Ser Cys Ala Ala Ser Gly Gly Ser Leu Ser Asn Tyr Val Leu Gly
                165                 170                 175

Trp Phe Arg Gln Ala Pro Gly Lys Gly Arg Glu Phe Val Ala Ala Ile
            180                 185                 190

Asn Trp Arg Asp Asp Ile Thr Ile Gly Pro Pro Asn Val Glu Gly Arg
        195                 200                 205

Phe Thr Ile Ser Arg Asp Asn Ala Lys Asn Thr Leu Tyr Leu Gln Met
    210                 215                 220

Asn Ser Leu Arg Pro Glu Asp Thr Ala Val Tyr Tyr Cys Gly Ala Gly
225                 230                 235                 240
```

```
Thr Pro Leu Asn Pro Gly Ala Tyr Ile Tyr Asp Trp Ser Tyr Asp Tyr
                245                 250                 255

Trp Gly Gln Gly Thr Leu Val Thr Val Ser Ser Gly Gly Gly Gly Ser
            260                 265                 270

Gly Gly Gly Gly Ser Gly Gly Gly Ser Glu Val Gln Leu Leu Glu
        275                 280                 285

Ser Gly Gly Gly Leu Val Gln Pro Gly Gly Ser Leu Arg Leu Ser Cys
290                 295                 300

Ala Ala Ser Gly Gly Ser Leu Ser Asn Tyr Val Leu Gly Trp Phe Arg
305                 310                 315                 320

Gln Ala Pro Gly Lys Gly Arg Glu Phe Val Ala Ile Asn Trp Arg
                325                 330                 335

Asp Asp Ile Thr Ile Gly Pro Pro Asn Val Glu Gly Arg Phe Thr Ile
            340                 345                 350

Ser Arg Asp Asn Ala Lys Asn Thr Leu Tyr Leu Gln Met Asn Ser Leu
        355                 360                 365

Arg Pro Glu Asp Thr Ala Val Tyr Tyr Cys Gly Ala Gly Thr Pro Leu
    370                 375                 380

Asn Pro Gly Ala Tyr Ile Tyr Asp Trp Ser Tyr Asp Tyr Trp Gly Gln
385                 390                 395                 400

Gly Thr Leu Val Thr Val Ser Ser
                405

<210> SEQ ID NO 75
<211> LENGTH: 408
<212> TYPE: PRT
<213> ORGANISM: Artificial Sequence
<220> FEATURE:
<223> OTHER INFORMATION: Nanobody sequence

<400> SEQUENCE: 75

Asp Val Gln Leu Leu Glu Ser Gly Gly Gly Leu Val Gln Pro Gly Gly
1               5                   10                  15

Ser Leu Arg Leu Ser Cys Ala Ala Ser Gly Gly Ser Leu Ser Asn Tyr
            20                  25                  30

Val Leu Gly Trp Phe Arg Gln Ala Pro Gly Lys Gly Arg Glu Phe Val
        35                  40                  45

Ala Ala Ile Asn Trp Arg Asp Asp Ile Thr Ile Gly Pro Pro Asn Val
    50                  55                  60

Glu Gly Arg Phe Thr Ile Ser Arg Asp Asn Ala Lys Asn Thr Leu Tyr
65                  70                  75                  80

Leu Gln Met Asn Ser Leu Arg Pro Glu Asp Thr Ala Val Tyr Tyr Cys
                85                  90                  95

Gly Ala Gly Thr Pro Leu Asn Pro Gly Ala Tyr Ile Tyr Asp Trp Ser
            100                 105                 110

Tyr Asp Tyr Trp Gly Gln Gly Thr Leu Val Thr Val Ser Ser Gly Gly
        115                 120                 125

Gly Gly Ser Gly Gly Gly Gly Ser Gly Gly Gly Gly Ser Glu Val Gln
    130                 135                 140

Leu Leu Glu Ser Gly Gly Gly Leu Val Gln Pro Gly Gly Ser Leu Arg
145                 150                 155                 160

Leu Ser Cys Ala Ala Ser Gly Gly Ser Leu Ser Asn Tyr Val Leu Gly
                165                 170                 175

Trp Phe Arg Gln Ala Pro Gly Lys Gly Arg Glu Phe Val Ala Ala Ile
            180                 185                 190
```

Asn Trp Arg Asp Asp Ile Thr Ile Gly Pro Pro Asn Val Glu Gly Arg
                195                 200                 205

Phe Thr Ile Ser Arg Asp Asn Ala Lys Asn Thr Leu Tyr Leu Gln Met
    210                 215                 220

Asn Ser Leu Arg Pro Glu Asp Thr Ala Val Tyr Tyr Cys Gly Ala Gly
225                 230                 235                 240

Thr Pro Leu Asn Pro Gly Ala Tyr Ile Tyr Asp Trp Ser Tyr Asp Tyr
                245                 250                 255

Trp Gly Gln Gly Thr Leu Val Thr Val Ser Ser Gly Gly Gly Gly Ser
                260                 265                 270

Gly Gly Gly Gly Ser Gly Gly Gly Gly Ser Glu Val Gln Leu Leu Glu
                275                 280                 285

Ser Gly Gly Gly Leu Val Gln Pro Gly Gly Ser Leu Arg Leu Ser Cys
290                 295                 300

Ala Ala Ser Gly Gly Ser Leu Ser Asn Tyr Val Leu Gly Trp Phe Arg
305                 310                 315                 320

Gln Ala Pro Gly Lys Gly Arg Glu Phe Val Ala Ala Ile Asn Trp Arg
                325                 330                 335

Asp Asp Ile Thr Ile Gly Pro Pro Asn Val Glu Gly Arg Phe Thr Ile
                340                 345                 350

Ser Arg Asp Asn Ala Lys Asn Thr Leu Tyr Leu Gln Met Asn Ser Leu
                355                 360                 365

Arg Pro Glu Asp Thr Ala Val Tyr Tyr Cys Gly Ala Gly Thr Pro Leu
                370                 375                 380

Asn Pro Gly Ala Tyr Ile Tyr Asp Trp Ser Tyr Asp Tyr Trp Gly Gln
385                 390                 395                 400

Gly Thr Leu Val Thr Val Ser Ser
                405

<210> SEQ ID NO 76
<211> LENGTH: 408
<212> TYPE: PRT
<213> ORGANISM: Artificial Sequence
<220> FEATURE:
<223> OTHER INFORMATION: Nanobody sequence

<400> SEQUENCE: 76

Glu Val Gln Leu Leu Glu Ser Gly Gly Gly Leu Val Gln Pro Gly Gly
1               5                   10                  15

Ser Leu Arg Leu Ser Cys Ala Ala Ser Gly Gly Ser Leu Ser Asn Tyr
                20                  25                  30

Val Leu Gly Trp Phe Arg Gln Ala Pro Gly Lys Gly Arg Glu Phe Val
            35                  40                  45

Ala Ala Ile Asn Trp Arg Gly Asp Ile Thr Ile Gly Pro Pro Asn Val
        50                  55                  60

Glu Gly Arg Phe Thr Ile Ser Arg Asp Asn Ser Lys Asn Thr Leu Tyr
65                  70                  75                  80

Leu Gln Met Asn Ser Leu Arg Pro Glu Asp Thr Ala Val Tyr Tyr Cys
                85                  90                  95

Gly Ala Gly Thr Pro Leu Asn Pro Gly Ala Tyr Ile Tyr Asp Trp Ser
            100                 105                 110

Tyr Asp Tyr Trp Gly Gln Gly Thr Leu Val Thr Val Ser Ser Gly Gly
        115                 120                 125

Gly Gly Ser Gly Gly Gly Gly Ser Gly Gly Gly Gly Ser Glu Val Gln
    130                 135                 140

Leu Leu Glu Ser Gly Gly Gly Leu Val Gln Pro Gly Gly Ser Leu Arg
145                 150                 155                 160

Leu Ser Cys Ala Ala Ser Gly Gly Ser Leu Ser Asn Tyr Val Leu Gly
                165                 170                 175

Trp Phe Arg Gln Ala Pro Gly Lys Gly Arg Glu Phe Val Ala Ala Ile
            180                 185                 190

Asn Trp Arg Gly Asp Ile Thr Ile Gly Pro Pro Asn Val Glu Gly Arg
            195                 200                 205

Phe Thr Ile Ser Arg Asp Asn Ser Lys Asn Thr Leu Tyr Leu Gln Met
        210                 215                 220

Asn Ser Leu Arg Pro Glu Asp Thr Ala Val Tyr Tyr Cys Gly Ala Gly
225                 230                 235                 240

Thr Pro Leu Asn Pro Gly Ala Tyr Ile Tyr Asp Trp Ser Tyr Asp Tyr
                245                 250                 255

Trp Gly Gln Gly Thr Leu Val Thr Val Ser Ser Gly Gly Gly Gly Ser
            260                 265                 270

Gly Gly Gly Gly Ser Gly Gly Gly Ser Glu Val Gln Leu Leu Glu
                275                 280                 285

Ser Gly Gly Gly Leu Val Gln Pro Gly Gly Ser Leu Arg Leu Ser Cys
290                 295                 300

Ala Ala Ser Gly Gly Ser Leu Ser Asn Tyr Val Leu Gly Trp Phe Arg
305                 310                 315                 320

Gln Ala Pro Gly Lys Gly Arg Glu Phe Val Ala Ala Ile Asn Trp Arg
                325                 330                 335

Gly Asp Ile Thr Ile Gly Pro Pro Asn Val Glu Gly Arg Phe Thr Ile
            340                 345                 350

Ser Arg Asp Asn Ser Lys Asn Thr Leu Tyr Leu Gln Met Asn Ser Leu
        355                 360                 365

Arg Pro Glu Asp Thr Ala Val Tyr Tyr Cys Gly Ala Gly Thr Pro Leu
370                 375                 380

Asn Pro Gly Ala Tyr Ile Tyr Asp Trp Ser Tyr Asp Tyr Trp Gly Gln
385                 390                 395                 400

Gly Thr Leu Val Thr Val Ser Ser
                405

<210> SEQ ID NO 77
<211> LENGTH: 408
<212> TYPE: PRT
<213> ORGANISM: Artificial Sequence
<220> FEATURE:
<223> OTHER INFORMATION: Nanobody sequence

<400> SEQUENCE: 77

Asp Val Gln Leu Leu Glu Ser Gly Gly Gly Leu Val Gln Pro Gly Gly
1               5                   10                  15

Ser Leu Arg Leu Ser Cys Ala Ala Ser Gly Gly Ser Leu Ser Asn Tyr
            20                  25                  30

Val Leu Gly Trp Phe Arg Gln Ala Pro Gly Lys Gly Arg Glu Phe Val
        35                  40                  45

Ala Ala Ile Asn Trp Arg Gly Asp Ile Thr Ile Gly Pro Pro Asn Val
    50                  55                  60

Glu Gly Arg Phe Thr Ile Ser Arg Asp Asn Ser Lys Asn Thr Leu Tyr
65                  70                  75                  80

Leu Gln Met Asn Ser Leu Arg Pro Glu Asp Thr Ala Val Tyr Tyr Cys
                85                  90                  95

Gly Ala Gly Thr Pro Leu Asn Pro Gly Ala Tyr Ile Tyr Asp Trp Ser
                100                 105                 110

Tyr Asp Tyr Trp Gly Gln Gly Thr Leu Val Thr Val Ser Ser Gly Gly
            115                 120                 125

Gly Gly Ser Gly Gly Gly Ser Gly Gly Gly Ser Glu Val Gln
130                 135                 140

Leu Leu Glu Ser Gly Gly Gly Leu Val Gln Pro Gly Gly Ser Leu Arg
145                 150                 155                 160

Leu Ser Cys Ala Ala Ser Gly Gly Ser Leu Ser Asn Tyr Val Leu Gly
                165                 170                 175

Trp Phe Arg Gln Ala Pro Gly Lys Gly Arg Glu Phe Val Ala Ala Ile
            180                 185                 190

Asn Trp Arg Gly Asp Ile Thr Ile Gly Pro Pro Asn Val Glu Gly Arg
            195                 200                 205

Phe Thr Ile Ser Arg Asp Asn Ser Lys Asn Thr Leu Tyr Leu Gln Met
210                 215                 220

Asn Ser Leu Arg Pro Glu Asp Thr Ala Val Tyr Tyr Cys Gly Ala Gly
225                 230                 235                 240

Thr Pro Leu Asn Pro Gly Ala Tyr Ile Tyr Asp Trp Ser Tyr Asp Tyr
                245                 250                 255

Trp Gly Gln Gly Thr Leu Val Thr Val Ser Ser Gly Gly Gly Gly Ser
            260                 265                 270

Gly Gly Gly Gly Ser Gly Gly Gly Ser Glu Val Gln Leu Leu Glu
            275                 280                 285

Ser Gly Gly Gly Leu Val Gln Pro Gly Gly Ser Leu Arg Leu Ser Cys
290                 295                 300

Ala Ala Ser Gly Gly Ser Leu Ser Asn Tyr Val Leu Gly Trp Phe Arg
305                 310                 315                 320

Gln Ala Pro Gly Lys Gly Arg Glu Phe Val Ala Ala Ile Asn Trp Arg
            325                 330                 335

Gly Asp Ile Thr Ile Gly Pro Pro Asn Val Glu Gly Arg Phe Thr Ile
            340                 345                 350

Ser Arg Asp Asn Ser Lys Asn Thr Leu Tyr Leu Gln Met Asn Ser Leu
            355                 360                 365

Arg Pro Glu Asp Thr Ala Val Tyr Tyr Cys Gly Ala Gly Thr Pro Leu
370                 375                 380

Asn Pro Gly Ala Tyr Ile Tyr Asp Trp Ser Tyr Asp Tyr Trp Gly Gln
385                 390                 395                 400

Gly Thr Leu Val Thr Val Ser Ser
                405

<210> SEQ ID NO 78
<211> LENGTH: 408
<212> TYPE: PRT
<213> ORGANISM: Artificial Sequence
<220> FEATURE:
<223> OTHER INFORMATION: Nanobody sequence

<400> SEQUENCE: 78

Glu Val Gln Leu Leu Glu Ser Gly Gly Gly Leu Val Gln Pro Gly Gly
1               5                   10                  15

Ser Leu Arg Leu Ser Cys Ala Ala Ser Gly Gly Ser Leu Ser Asn Tyr
            20                  25                  30

Val Leu Gly Trp Phe Arg Gln Ala Pro Gly Lys Gly Arg Glu Phe Val
        35                  40                  45

Ala Ala Ile Asn Trp Arg Asp Asp Ile Thr Ile Gly Pro Pro Asn Val
 50                  55                  60

Glu Gly Arg Phe Thr Ile Ser Arg Asp Asn Ser Lys Asn Thr Leu Tyr
 65                  70                  75                  80

Leu Gln Met Asn Ser Leu Arg Pro Glu Asp Thr Ala Val Tyr Tyr Cys
             85                  90                  95

Gly Ala Gly Thr Pro Leu Asn Pro Gly Ala Tyr Ile Tyr Asp Trp Ser
            100                 105                 110

Tyr Asp Tyr Trp Gly Gln Gly Thr Leu Val Thr Val Ser Ser Gly Gly
        115                 120                 125

Gly Gly Ser Gly Gly Gly Ser Gly Gly Gly Ser Glu Val Gln
    130                 135                 140

Leu Leu Glu Ser Gly Gly Gly Leu Val Gln Pro Gly Gly Ser Leu Arg
145                 150                 155                 160

Leu Ser Cys Ala Ala Ser Gly Gly Ser Leu Ser Asn Tyr Val Leu Gly
                165                 170                 175

Trp Phe Arg Gln Ala Pro Gly Lys Gly Arg Glu Phe Val Ala Ala Ile
            180                 185                 190

Asn Trp Arg Asp Asp Ile Thr Ile Gly Pro Pro Asn Val Glu Gly Arg
        195                 200                 205

Phe Thr Ile Ser Arg Asp Asn Ser Lys Asn Thr Leu Tyr Leu Gln Met
    210                 215                 220

Asn Ser Leu Arg Pro Glu Asp Thr Ala Val Tyr Tyr Cys Gly Ala Gly
225                 230                 235                 240

Thr Pro Leu Asn Pro Gly Ala Tyr Ile Tyr Asp Trp Ser Tyr Asp Tyr
                245                 250                 255

Trp Gly Gln Gly Thr Leu Val Thr Val Ser Ser Gly Gly Gly Gly Ser
            260                 265                 270

Gly Gly Gly Gly Ser Gly Gly Gly Ser Glu Val Gln Leu Leu Glu
        275                 280                 285

Ser Gly Gly Gly Leu Val Gln Pro Gly Gly Ser Leu Arg Leu Ser Cys
    290                 295                 300

Ala Ala Ser Gly Gly Ser Leu Ser Asn Tyr Val Leu Gly Trp Phe Arg
305                 310                 315                 320

Gln Ala Pro Gly Lys Gly Arg Glu Phe Val Ala Ala Ile Asn Trp Arg
                325                 330                 335

Asp Asp Ile Thr Ile Gly Pro Pro Asn Val Glu Gly Arg Phe Thr Ile
            340                 345                 350

Ser Arg Asp Asn Ser Lys Asn Thr Leu Tyr Leu Gln Met Asn Ser Leu
        355                 360                 365

Arg Pro Glu Asp Thr Ala Val Tyr Tyr Cys Gly Ala Gly Thr Pro Leu
    370                 375                 380

Asn Pro Gly Ala Tyr Ile Tyr Asp Trp Ser Tyr Asp Tyr Trp Gly Gln
385                 390                 395                 400

Gly Thr Leu Val Thr Val Ser Ser
                405

<210> SEQ ID NO 79
<211> LENGTH: 408
<212> TYPE: PRT
<213> ORGANISM: Artificial Sequence
<220> FEATURE:
<223> OTHER INFORMATION: Nanobody sequence

<400> SEQUENCE: 79

Asp Val Gln Leu Leu Glu Ser Gly Gly Gly Leu Val Gln Pro Gly Gly
1               5                   10                  15

Ser Leu Arg Leu Ser Cys Ala Ala Ser Gly Gly Ser Leu Ser Asn Tyr
            20                  25                  30

Val Leu Gly Trp Phe Arg Gln Ala Pro Gly Lys Gly Arg Glu Phe Val
            35                  40                  45

Ala Ala Ile Asn Trp Arg Asp Asp Ile Thr Ile Gly Pro Pro Asn Val
50                  55                  60

Glu Gly Arg Phe Thr Ile Ser Arg Asp Asn Ser Lys Asn Thr Leu Tyr
65                  70                  75                  80

Leu Gln Met Asn Ser Leu Arg Pro Glu Asp Thr Ala Val Tyr Tyr Cys
                85                  90                  95

Gly Ala Gly Thr Pro Leu Asn Pro Gly Ala Tyr Ile Tyr Asp Trp Ser
            100                 105                 110

Tyr Asp Tyr Trp Gly Gln Gly Thr Leu Val Thr Val Ser Ser Gly Gly
        115                 120                 125

Gly Gly Ser Gly Gly Gly Ser Gly Gly Gly Ser Glu Val Gln
            130                 135                 140

Leu Leu Glu Ser Gly Gly Gly Leu Val Gln Pro Gly Gly Ser Leu Arg
145                 150                 155                 160

Leu Ser Cys Ala Ala Ser Gly Gly Ser Leu Ser Asn Tyr Val Leu Gly
                165                 170                 175

Trp Phe Arg Gln Ala Pro Gly Lys Gly Arg Glu Phe Val Ala Ala Ile
            180                 185                 190

Asn Trp Arg Asp Asp Ile Thr Ile Gly Pro Pro Asn Val Glu Gly Arg
        195                 200                 205

Phe Thr Ile Ser Arg Asp Asn Ser Lys Asn Thr Leu Tyr Leu Gln Met
    210                 215                 220

Asn Ser Leu Arg Pro Glu Asp Thr Ala Val Tyr Tyr Cys Gly Ala Gly
225                 230                 235                 240

Thr Pro Leu Asn Pro Gly Ala Tyr Ile Tyr Asp Trp Ser Tyr Asp Tyr
                245                 250                 255

Trp Gly Gln Gly Thr Leu Val Thr Val Ser Ser Gly Gly Gly Gly Ser
            260                 265                 270

Gly Gly Gly Gly Ser Gly Gly Gly Ser Glu Val Gln Leu Leu Glu
        275                 280                 285

Ser Gly Gly Gly Leu Val Gln Pro Gly Gly Ser Leu Arg Leu Ser Cys
    290                 295                 300

Ala Ala Ser Gly Gly Ser Leu Ser Asn Tyr Val Leu Gly Trp Phe Arg
305                 310                 315                 320

Gln Ala Pro Gly Lys Gly Arg Glu Phe Val Ala Ala Ile Asn Trp Arg
                325                 330                 335

Asp Asp Ile Thr Ile Gly Pro Pro Asn Val Glu Gly Arg Phe Thr Ile
            340                 345                 350

Ser Arg Asp Asn Ser Lys Asn Thr Leu Tyr Leu Gln Met Asn Ser Leu
        355                 360                 365

Arg Pro Glu Asp Thr Ala Val Tyr Tyr Cys Gly Ala Gly Thr Pro Leu
    370                 375                 380

Asn Pro Gly Ala Tyr Ile Tyr Asp Trp Ser Tyr Asp Tyr Trp Gly Gln
385                 390                 395                 400

Gly Thr Leu Val Thr Val Ser Ser
                405

```
<210> SEQ ID NO 80
<211> LENGTH: 408
<212> TYPE: PRT
<213> ORGANISM: Artificial Sequence
<220> FEATURE:
<223> OTHER INFORMATION: Nanobody sequence

<400> SEQUENCE: 80

Glu Val Gln Leu Val Glu Ser Gly Gly Gly Leu Val Gln Pro Gly Gly
1               5                   10                  15

Ser Leu Arg Leu Ser Cys Ala Ala Ser Gly Gly Ser Leu Ser Asn Tyr
            20                  25                  30

Val Leu Gly Trp Phe Arg Gln Ala Pro Gly Lys Glu Arg Glu Phe Val
        35                  40                  45

Ala Ala Ile Asn Trp Arg Gly Asp Ile Thr Ile Gly Pro Pro Asn Val
    50                  55                  60

Glu Gly Arg Phe Thr Ile Ser Arg Asp Asn Ala Lys Asn Thr Gly Tyr
65                  70                  75                  80

Leu Gln Met Asn Ser Leu Arg Pro Asp Asp Thr Ala Val Tyr Tyr Cys
                85                  90                  95

Gly Ala Gly Thr Pro Leu Asn Pro Gly Ala Tyr Ile Tyr Asp Trp Ser
            100                 105                 110

Tyr Asp Tyr Trp Gly Gln Gly Thr Leu Val Thr Val Ser Ser Gly Gly
        115                 120                 125

Gly Gly Ser Gly Gly Gly Gly Ser Gly Gly Gly Gly Ser Glu Val Gln
    130                 135                 140

Leu Val Glu Ser Gly Gly Gly Leu Val Gln Pro Gly Gly Ser Leu Arg
145                 150                 155                 160

Leu Ser Cys Ala Ala Ser Gly Gly Ser Leu Ser Asn Tyr Val Leu Gly
                165                 170                 175

Trp Phe Arg Gln Ala Pro Gly Lys Glu Arg Glu Phe Val Ala Ala Ile
            180                 185                 190

Asn Trp Arg Gly Asp Ile Thr Ile Gly Pro Pro Asn Val Glu Gly Arg
        195                 200                 205

Phe Thr Ile Ser Arg Asp Asn Ala Lys Asn Thr Gly Tyr Leu Gln Met
    210                 215                 220

Asn Ser Leu Arg Pro Asp Asp Thr Ala Val Tyr Tyr Cys Gly Ala Gly
225                 230                 235                 240

Thr Pro Leu Asn Pro Gly Ala Tyr Ile Tyr Asp Trp Ser Tyr Asp Tyr
                245                 250                 255

Trp Gly Gln Gly Thr Leu Val Thr Val Ser Ser Gly Gly Gly Gly Ser
            260                 265                 270

Gly Gly Gly Gly Ser Gly Gly Gly Gly Ser Glu Val Gln Leu Val Glu
        275                 280                 285

Ser Gly Gly Gly Leu Val Gln Pro Gly Gly Ser Leu Arg Leu Ser Cys
    290                 295                 300

Ala Ala Ser Gly Gly Ser Leu Ser Asn Tyr Val Leu Gly Trp Phe Arg
305                 310                 315                 320

Gln Ala Pro Gly Lys Glu Arg Glu Phe Val Ala Ala Ile Asn Trp Arg
                325                 330                 335

Gly Asp Ile Thr Ile Gly Pro Pro Asn Val Glu Gly Arg Phe Thr Ile
            340                 345                 350

Ser Arg Asp Asn Ala Lys Asn Thr Gly Tyr Leu Gln Met Asn Ser Leu
        355                 360                 365
```

```
Arg Pro Asp Asp Thr Ala Val Tyr Tyr Cys Gly Ala Gly Thr Pro Leu
370                 375                 380

Asn Pro Gly Ala Tyr Ile Tyr Asp Trp Ser Tyr Asp Tyr Trp Gly Gln
385                 390                 395                 400

Gly Thr Leu Val Thr Val Ser Ser
                405

<210> SEQ ID NO 81
<211> LENGTH: 408
<212> TYPE: PRT
<213> ORGANISM: Artificial Sequence
<220> FEATURE:
<223> OTHER INFORMATION: Nanobody sequence

<400> SEQUENCE: 81

Asp Val Gln Leu Val Glu Ser Gly Gly Gly Leu Val Gln Pro Gly Gly
1               5                   10                  15

Ser Leu Arg Leu Ser Cys Ala Ala Ser Gly Gly Ser Leu Ser Asn Tyr
            20                  25                  30

Val Leu Gly Trp Phe Arg Gln Ala Pro Gly Lys Glu Arg Glu Phe Val
        35                  40                  45

Ala Ala Ile Asn Trp Arg Gly Asp Ile Thr Ile Gly Pro Pro Asn Val
50                  55                  60

Glu Gly Arg Phe Thr Ile Ser Arg Asp Asn Ala Lys Asn Thr Gly Tyr
65                  70                  75                  80

Leu Gln Met Asn Ser Leu Arg Pro Asp Asp Thr Ala Val Tyr Tyr Cys
                85                  90                  95

Gly Ala Gly Thr Pro Leu Asn Pro Gly Ala Tyr Ile Tyr Asp Trp Ser
            100                 105                 110

Tyr Asp Tyr Trp Gly Gln Gly Thr Leu Val Thr Val Ser Ser Gly Gly
        115                 120                 125

Gly Gly Ser Gly Gly Gly Ser Gly Gly Gly Ser Glu Val Gln
            130                 135                 140

Leu Val Glu Ser Gly Gly Gly Leu Val Gln Pro Gly Gly Ser Leu Arg
145                 150                 155                 160

Leu Ser Cys Ala Ala Ser Gly Gly Ser Leu Ser Asn Tyr Val Leu Gly
                165                 170                 175

Trp Phe Arg Gln Ala Pro Gly Lys Glu Arg Glu Phe Val Ala Ala Ile
            180                 185                 190

Asn Trp Arg Gly Asp Ile Thr Ile Gly Pro Pro Asn Val Glu Gly Arg
        195                 200                 205

Phe Thr Ile Ser Arg Asp Asn Ala Lys Asn Thr Gly Tyr Leu Gln Met
210                 215                 220

Asn Ser Leu Arg Pro Asp Asp Thr Ala Val Tyr Tyr Cys Gly Ala Gly
225                 230                 235                 240

Thr Pro Leu Asn Pro Gly Ala Tyr Ile Tyr Asp Trp Ser Tyr Asp Tyr
                245                 250                 255

Trp Gly Gln Gly Thr Leu Val Thr Val Ser Ser Gly Gly Gly Gly Ser
            260                 265                 270

Gly Gly Gly Gly Ser Gly Gly Gly Ser Glu Val Gln Leu Val Glu
        275                 280                 285

Ser Gly Gly Gly Leu Val Gln Pro Gly Gly Ser Leu Arg Leu Ser Cys
            290                 295                 300

Ala Ala Ser Gly Gly Ser Leu Ser Asn Tyr Val Leu Gly Trp Phe Arg
305                 310                 315                 320
```

```
Gln Ala Pro Gly Lys Glu Arg Glu Phe Val Ala Ile Asn Trp Arg
            325                 330                 335

Gly Asp Ile Thr Ile Gly Pro Pro Asn Val Glu Gly Arg Phe Thr Ile
            340                 345                 350

Ser Arg Asp Asn Ala Lys Asn Thr Gly Tyr Leu Gln Met Asn Ser Leu
            355                 360                 365

Arg Pro Asp Asp Thr Ala Val Tyr Tyr Cys Gly Ala Gly Thr Pro Leu
        370                 375                 380

Asn Pro Gly Ala Tyr Ile Tyr Asp Trp Ser Tyr Asp Tyr Trp Gly Gln
385                 390                 395                 400

Gly Thr Leu Val Thr Val Ser Ser
                405
```

<210> SEQ ID NO 82
<211> LENGTH: 408
<212> TYPE: PRT
<213> ORGANISM: Artificial Sequence
<220> FEATURE:
<223> OTHER INFORMATION: Nanobody sequence

<400> SEQUENCE: 82

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Gly Ser Leu Ser Asn Tyr
            20                  25                  30

Val Leu Gly Trp Phe Arg Gln Ala Pro Gly Lys Glu Arg Glu Phe Val
        35                  40                  45

Ala Ala Ile Asn Trp Arg Gly Asp Ile Thr Ile Gly Pro Pro Asn Val
    50                  55                  60

Glu Gly Arg Phe Thr Ile Ser Arg Asp Asn Ala Lys Asn Thr Gly Tyr
65                  70                  75                  80

Leu Gln Met Asn Ser Leu Arg Pro Glu Asp Thr Ala Val Tyr Tyr Cys
                85                  90                  95

Gly Ala Gly Thr Pro Leu Asn Pro Gly Ala Tyr Ile Tyr Asp Trp Ser
            100                 105                 110

Tyr Asp Tyr Trp Gly Gln Gly Thr Leu Val Thr Val Ser Ser Gly Gly
        115                 120                 125

Gly Gly Ser Gly Gly Gly Gly Ser Gly Gly Gly Gly Ser Glu Val Gln
    130                 135                 140

Leu Val Glu Ser Gly Gly Gly Leu Val Gln Pro Gly Gly Ser Leu Arg
145                 150                 155                 160

Leu Ser Cys Ala Ala Ser Gly Gly Ser Leu Ser Asn Tyr Val Leu Gly
                165                 170                 175

Trp Phe Arg Gln Ala Pro Gly Lys Glu Arg Glu Phe Val Ala Ala Ile
            180                 185                 190

Asn Trp Arg Gly Asp Ile Thr Ile Gly Pro Pro Asn Val Glu Gly Arg
        195                 200                 205

Phe Thr Ile Ser Arg Asp Asn Ala Lys Asn Thr Gly Tyr Leu Gln Met
    210                 215                 220

Asn Ser Leu Arg Pro Glu Asp Thr Ala Val Tyr Tyr Cys Gly Ala Gly
225                 230                 235                 240

Thr Pro Leu Asn Pro Gly Ala Tyr Ile Tyr Asp Trp Ser Tyr Asp Tyr
                245                 250                 255

Trp Gly Gln Gly Thr Leu Val Thr Val Ser Ser Gly Gly Gly Gly Ser
            260                 265                 270
```

Gly Gly Gly Gly Ser Gly Gly Gly Ser Glu Val Gln Leu Val Glu
                275                 280                 285

Ser Gly Gly Gly Leu Val Gln Pro Gly Gly Ser Leu Arg Leu Ser Cys
290                 295                 300

Ala Ala Ser Gly Gly Ser Leu Ser Asn Tyr Val Leu Gly Trp Phe Arg
305                 310                 315                 320

Gln Ala Pro Gly Lys Glu Arg Glu Phe Val Ala Ala Ile Asn Trp Arg
                325                 330                 335

Gly Asp Ile Thr Ile Gly Pro Pro Asn Val Glu Gly Arg Phe Thr Ile
                340                 345                 350

Ser Arg Asp Asn Ala Lys Asn Thr Gly Tyr Leu Gln Met Asn Ser Leu
                355                 360                 365

Arg Pro Glu Asp Thr Ala Val Tyr Tyr Cys Gly Ala Gly Thr Pro Leu
                370                 375                 380

Asn Pro Gly Ala Tyr Ile Tyr Asp Trp Ser Tyr Asp Tyr Trp Gly Gln
385                 390                 395                 400

Gly Thr Leu Val Thr Val Ser Ser
                405

<210> SEQ ID NO 83
<211> LENGTH: 408
<212> TYPE: PRT
<213> ORGANISM: Artificial Sequence
<220> FEATURE:
<223> OTHER INFORMATION: Nanobody sequence

<400> SEQUENCE: 83

Glu Val Gln Leu Val Glu Ser Gly Gly Gly Leu Val Gln Pro Gly Gly
1               5                   10                  15

Ser Leu Arg Leu Ser Cys Ala Ala Ser Gly Gly Ser Leu Ser Asn Tyr
            20                  25                  30

Val Leu Gly Trp Phe Arg Gln Ala Pro Gly Lys Glu Arg Glu Phe Val
        35                  40                  45

Ala Ala Ile Asn Trp Arg Gly Asp Ile Thr Ile Gly Pro Pro Asn Val
    50                  55                  60

Glu Gly Arg Phe Thr Ile Ser Arg Asp Asn Ala Lys Asn Thr Gly Tyr
65                  70                  75                  80

Leu Gln Met Asn Ser Leu Arg Pro Glu Asp Thr Ala Val Tyr Tyr Cys
                85                  90                  95

Gly Ala Gly Thr Pro Leu Asn Pro Gly Ala Tyr Ile Tyr Asp Trp Ser
            100                 105                 110

Tyr Asp Tyr Trp Gly Arg Gly Thr Leu Val Thr Val Ser Ser Gly Gly
        115                 120                 125

Gly Gly Ser Gly Gly Gly Ser Gly Gly Gly Ser Glu Val Gln
    130                 135                 140

Leu Val Glu Ser Gly Gly Gly Leu Val Gln Pro Gly Gly Ser Leu Arg
145                 150                 155                 160

Leu Ser Cys Ala Ala Ser Gly Gly Ser Leu Ser Asn Tyr Val Leu Gly
                165                 170                 175

Trp Phe Arg Gln Ala Pro Gly Lys Glu Arg Glu Phe Val Ala Ala Ile
            180                 185                 190

Asn Trp Arg Gly Asp Ile Thr Ile Gly Pro Pro Asn Val Glu Gly Arg
        195                 200                 205

Phe Thr Ile Ser Arg Asp Asn Ala Lys Asn Thr Gly Tyr Leu Gln Met
    210                 215                 220

```
Asn Ser Leu Arg Pro Glu Asp Thr Ala Val Tyr Tyr Cys Gly Ala Gly
225                 230                 235                 240

Thr Pro Leu Asn Pro Gly Ala Tyr Ile Tyr Asp Trp Ser Tyr Asp Tyr
                245                 250                 255

Trp Gly Arg Gly Thr Leu Val Thr Val Ser Ser Gly Gly Gly Gly Ser
            260                 265                 270

Gly Gly Gly Gly Ser Gly Gly Gly Ser Glu Val Gln Leu Val Glu
        275                 280                 285

Ser Gly Gly Gly Leu Val Gln Pro Gly Gly Ser Leu Arg Leu Ser Cys
    290                 295                 300

Ala Ala Ser Gly Gly Ser Leu Ser Asn Tyr Val Leu Gly Trp Phe Arg
305                 310                 315                 320

Gln Ala Pro Gly Lys Glu Arg Glu Phe Val Ala Ala Ile Asn Trp Arg
                325                 330                 335

Gly Asp Ile Thr Ile Gly Pro Pro Asn Val Glu Gly Arg Phe Thr Ile
                340                 345                 350

Ser Arg Asp Asn Ala Lys Asn Thr Gly Tyr Leu Gln Met Asn Ser Leu
                355                 360                 365

Arg Pro Glu Asp Thr Ala Val Tyr Tyr Cys Gly Ala Gly Thr Pro Leu
            370                 375                 380

Asn Pro Gly Ala Tyr Ile Tyr Asp Trp Ser Tyr Asp Tyr Trp Gly Arg
385                 390                 395                 400

Gly Thr Leu Val Thr Val Ser Ser
                405

<210> SEQ ID NO 84
<211> LENGTH: 408
<212> TYPE: PRT
<213> ORGANISM: Artificial Sequence
<220> FEATURE:
<223> OTHER INFORMATION: Nanobody sequence

<400> SEQUENCE: 84

Asp Val Gln Leu Val Glu Ser Gly Gly Gly Leu Val Gln Pro Gly Gly
1               5                   10                  15

Ser Leu Arg Leu Ser Cys Ala Ala Ser Gly Gly Ser Leu Ser Asn Tyr
            20                  25                  30

Val Leu Gly Trp Phe Arg Gln Ala Pro Gly Lys Glu Arg Glu Phe Val
        35                  40                  45

Ala Ala Ile Asn Trp Arg Gly Asp Ile Thr Ile Gly Pro Pro Asn Val
    50                  55                  60

Glu Gly Arg Phe Thr Ile Ser Arg Asp Asn Ala Lys Asn Thr Gly Tyr
65                  70                  75                  80

Leu Gln Met Asn Ser Leu Arg Pro Glu Asp Thr Ala Val Tyr Tyr Cys
                85                  90                  95

Gly Ala Gly Thr Pro Leu Asn Pro Gly Ala Tyr Ile Tyr Asp Trp Ser
            100                 105                 110

Tyr Asp Tyr Trp Gly Arg Gly Thr Leu Val Thr Val Ser Ser Gly Gly
        115                 120                 125

Gly Gly Ser Gly Gly Gly Gly Ser Gly Gly Gly Gly Ser Glu Val Gln
    130                 135                 140

Leu Val Glu Ser Gly Gly Gly Leu Val Gln Pro Gly Gly Ser Leu Arg
145                 150                 155                 160

Leu Ser Cys Ala Ala Ser Gly Gly Ser Leu Ser Asn Tyr Val Leu Gly
                165                 170                 175
```

```
Trp Phe Arg Gln Ala Pro Gly Lys Glu Arg Glu Phe Val Ala Ala Ile
            180                 185                 190

Asn Trp Arg Gly Asp Ile Thr Ile Gly Pro Pro Asn Val Glu Gly Arg
        195                 200                 205

Phe Thr Ile Ser Arg Asp Asn Ala Lys Asn Thr Gly Tyr Leu Gln Met
    210                 215                 220

Asn Ser Leu Arg Pro Glu Asp Thr Ala Val Tyr Tyr Cys Gly Ala Gly
225                 230                 235                 240

Thr Pro Leu Asn Pro Gly Ala Tyr Ile Tyr Asp Trp Ser Tyr Asp Tyr
                245                 250                 255

Trp Gly Arg Gly Thr Leu Val Thr Val Ser Ser Gly Gly Gly Gly Ser
            260                 265                 270

Gly Gly Gly Gly Ser Gly Gly Gly Ser Glu Val Gln Leu Val Glu
            275                 280                 285

Ser Gly Gly Gly Leu Val Gln Pro Gly Gly Ser Leu Arg Leu Ser Cys
290                 295                 300

Ala Ala Ser Gly Gly Ser Leu Ser Asn Tyr Val Leu Gly Trp Phe Arg
305                 310                 315                 320

Gln Ala Pro Gly Lys Glu Arg Glu Phe Val Ala Ala Ile Asn Trp Arg
                325                 330                 335

Gly Asp Ile Thr Ile Gly Pro Pro Asn Val Glu Gly Arg Phe Thr Ile
            340                 345                 350

Ser Arg Asp Asn Ala Lys Asn Thr Gly Tyr Leu Gln Met Asn Ser Leu
            355                 360                 365

Arg Pro Glu Asp Thr Ala Val Tyr Tyr Cys Gly Ala Gly Thr Pro Leu
    370                 375                 380

Asn Pro Gly Ala Tyr Ile Tyr Asp Trp Ser Tyr Asp Tyr Trp Gly Arg
385                 390                 395                 400

Gly Thr Leu Val Thr Val Ser Ser
            405

<210> SEQ ID NO 85
<211> LENGTH: 408
<212> TYPE: PRT
<213> ORGANISM: Artificial Sequence
<220> FEATURE:
<223> OTHER INFORMATION: Nanobody sequence

<400> SEQUENCE: 85

Asp Val Gln Leu Val Glu Ser Gly Gly Gly Leu Val Gln Pro Gly Gly
1               5                   10                  15

Ser Leu Arg Leu Ser Cys Ala Ala Ser Gly Gly Ser Leu Ser Asn Tyr
            20                  25                  30

Val Leu Gly Trp Phe Arg Gln Ala Pro Gly Lys Glu Arg Glu Phe Val
        35                  40                  45

Ala Ala Ile Asn Trp Arg Gly Asp Ile Thr Ile Gly Pro Pro Asn Val
    50                  55                  60

Glu Gly Arg Phe Thr Ile Ser Arg Asp Asn Ala Lys Asn Thr Gly Tyr
65                  70                  75                  80

Leu Gln Met Asn Ser Leu Arg Pro Glu Asp Thr Ala Val Tyr Tyr Cys
                85                  90                  95

Gly Ala Gly Thr Pro Leu Asn Pro Gly Ala Tyr Ile Tyr Asp Trp Ser
            100                 105                 110

Tyr Asp Tyr Trp Gly Gln Gly Thr Leu Val Thr Val Ser Ser Gly Gly
        115                 120                 125
```

```
Gly Gly Ser Gly Gly Gly Ser Gly Gly Gly Ser Glu Val Gln
        130             135             140
Leu Val Glu Ser Gly Gly Leu Val Gln Pro Gly Gly Ser Leu Arg
145             150             155                 160
Leu Ser Cys Ala Ala Ser Gly Gly Ser Leu Ser Asn Tyr Val Leu Gly
                165             170             175
Trp Phe Arg Gln Ala Pro Gly Lys Glu Arg Glu Phe Val Ala Ala Ile
            180             185             190
Asn Trp Arg Gly Asp Ile Thr Ile Gly Pro Pro Asn Val Glu Gly Arg
            195             200             205
Phe Thr Ile Ser Arg Asp Asn Ala Lys Asn Thr Gly Tyr Leu Gln Met
    210             215             220
Asn Ser Leu Arg Pro Glu Asp Thr Ala Val Tyr Tyr Cys Gly Ala Gly
225             230             235             240
Thr Pro Leu Asn Pro Gly Ala Tyr Ile Tyr Asp Trp Ser Tyr Asp Tyr
                245             250             255
Trp Gly Gln Gly Thr Leu Val Thr Val Ser Ser Gly Gly Gly Ser
            260             265             270
Gly Gly Gly Gly Ser Gly Gly Gly Ser Glu Val Gln Leu Val Glu
        275             280             285
Ser Gly Gly Leu Val Gln Pro Gly Gly Ser Leu Arg Leu Ser Cys
290             295             300
Ala Ala Ser Gly Gly Ser Leu Ser Asn Tyr Val Leu Gly Trp Phe Arg
305             310             315             320
Gln Ala Pro Gly Lys Glu Arg Glu Phe Val Ala Ala Ile Asn Trp Arg
            325             330             335
Gly Asp Ile Thr Ile Gly Pro Pro Asn Val Glu Gly Arg Phe Thr Ile
            340             345             350
Ser Arg Asp Asn Ala Lys Asn Thr Gly Tyr Leu Gln Met Asn Ser Leu
            355             360             365
Arg Pro Glu Asp Thr Ala Val Tyr Tyr Cys Gly Ala Gly Thr Pro Leu
    370             375             380
Asn Pro Gly Ala Tyr Ile Tyr Asp Trp Ser Tyr Asp Tyr Trp Gly Gln
385             390             395             400
Gly Thr Leu Val Thr Val Ser Ser
                405

<210> SEQ ID NO 86
<211> LENGTH: 5
<212> TYPE: PRT
<213> ORGANISM: Artificial Sequence
<220> FEATURE:
<223> OTHER INFORMATION: Linker sequence

<400> SEQUENCE: 86

Gly Gly Gly Gly Ser
1               5

<210> SEQ ID NO 87
<211> LENGTH: 7
<212> TYPE: PRT
<213> ORGANISM: Artificial Sequence
<220> FEATURE:
<223> OTHER INFORMATION: Linker sequence

<400> SEQUENCE: 87

Ser Gly Gly Ser Gly Gly Ser
1               5
```

```
<210> SEQ ID NO 88
<211> LENGTH: 9
<212> TYPE: PRT
<213> ORGANISM: Artificial Sequence
<220> FEATURE:
<223> OTHER INFORMATION: Linker sequence

<400> SEQUENCE: 88

Gly Gly Gly Gly Ser Gly Gly Gly Ser
1               5

<210> SEQ ID NO 89
<211> LENGTH: 9
<212> TYPE: PRT
<213> ORGANISM: Artificial Sequence
<220> FEATURE:
<223> OTHER INFORMATION: Linker sequence

<400> SEQUENCE: 89

Gly Gly Gly Gly Ser Gly Gly Gly Ser
1               5

<210> SEQ ID NO 90
<211> LENGTH: 10
<212> TYPE: PRT
<213> ORGANISM: Artificial Sequence
<220> FEATURE:
<223> OTHER INFORMATION: Linker sequence

<400> SEQUENCE: 90

Gly Gly Gly Gly Ser Gly Gly Gly Gly Ser
1               5                   10

<210> SEQ ID NO 91
<211> LENGTH: 15
<212> TYPE: PRT
<213> ORGANISM: Artificial Sequence
<220> FEATURE:
<223> OTHER INFORMATION: Linker sequence

<400> SEQUENCE: 91

Gly Gly Gly Gly Ser Gly Gly Gly Gly Ser Gly Gly Gly Gly Ser
1               5                   10                  15

<210> SEQ ID NO 92
<211> LENGTH: 18
<212> TYPE: PRT
<213> ORGANISM: Artificial Sequence
<220> FEATURE:
<223> OTHER INFORMATION: Linker sequence

<400> SEQUENCE: 92

Gly Gly Gly Gly Ser Gly Gly Gly Ser Gly Gly Gly Gly Gly
1               5                   10                  15

Gly Ser

<210> SEQ ID NO 93
<211> LENGTH: 20
<212> TYPE: PRT
<213> ORGANISM: Artificial Sequence
<220> FEATURE:
<223> OTHER INFORMATION: Linker sequence

<400> SEQUENCE: 93

Gly Gly Gly Gly Ser Gly Gly Gly Gly Ser Gly Gly Gly Gly Ser Gly
```

```
1               5                   10                  15
Gly Gly Gly Ser
            20

<210> SEQ ID NO 94
<211> LENGTH: 25
<212> TYPE: PRT
<213> ORGANISM: Artificial Sequence
<220> FEATURE:
<223> OTHER INFORMATION: Linker sequence

<400> SEQUENCE: 94

Gly Gly Gly Gly Ser Gly Gly Gly Gly Ser Gly Gly Gly Gly Ser Gly
1               5                   10                  15

Gly Gly Gly Ser Gly Gly Gly Gly Ser
            20                  25

<210> SEQ ID NO 95
<211> LENGTH: 30
<212> TYPE: PRT
<213> ORGANISM: Artificial Sequence
<220> FEATURE:
<223> OTHER INFORMATION: Linker sequence

<400> SEQUENCE: 95

Gly Gly Gly Gly Ser Gly Gly Gly Gly Ser Gly Gly Gly Gly Ser Gly
1               5                   10                  15

Gly Gly Gly Ser Gly Gly Gly Gly Ser Gly Gly Gly Gly Ser
            20                  25                  30

<210> SEQ ID NO 96
<211> LENGTH: 35
<212> TYPE: PRT
<213> ORGANISM: Artificial Sequence
<220> FEATURE:
<223> OTHER INFORMATION: Linker sequence

<400> SEQUENCE: 96

Gly Gly Gly Gly Ser Gly Gly Gly Gly Ser Gly Gly Gly Gly Ser Gly
1               5                   10                  15

Gly Gly Gly Ser Gly Gly Gly Gly Ser Gly Gly Gly Gly Ser Gly Gly
            20                  25                  30

Gly Gly Ser
        35

<210> SEQ ID NO 97
<211> LENGTH: 15
<212> TYPE: PRT
<213> ORGANISM: Artificial Sequence
<220> FEATURE:
<223> OTHER INFORMATION: Linker sequence

<400> SEQUENCE: 97

Glu Pro Lys Ser Cys Asp Lys Thr His Thr Cys Pro Pro Cys Pro
1               5                   10                  15

<210> SEQ ID NO 98
<211> LENGTH: 24
<212> TYPE: PRT
<213> ORGANISM: Artificial Sequence
<220> FEATURE:
<223> OTHER INFORMATION: Linker sequence

<400> SEQUENCE: 98
```

```
Gly Gly Gly Gly Ser Gly Gly Gly Ser Glu Pro Lys Ser Cys Asp Lys
1               5                   10                  15

Thr His Thr Cys Pro Pro Cys Pro
            20

<210> SEQ ID NO 99
<211> LENGTH: 12
<212> TYPE: PRT
<213> ORGANISM: Artificial Sequence
<220> FEATURE:
<223> OTHER INFORMATION: Linker sequence

<400> SEQUENCE: 99

Glu Pro Lys Thr Pro Lys Pro Gln Pro Ala Ala Ala
1               5                   10

<210> SEQ ID NO 100
<211> LENGTH: 62
<212> TYPE: PRT
<213> ORGANISM: Artificial Sequence
<220> FEATURE:
<223> OTHER INFORMATION: Linker sequence

<400> SEQUENCE: 100

Glu Leu Lys Thr Pro Leu Gly Asp Thr Thr His Thr Cys Pro Arg Cys
1               5                   10                  15

Pro Glu Pro Lys Ser Cys Asp Thr Pro Pro Pro Cys Pro Arg Cys Pro
                20                  25                  30

Glu Pro Lys Ser Cys Asp Thr Pro Pro Pro Cys Pro Arg Cys Pro Glu
            35                  40                  45

Pro Lys Ser Cys Asp Thr Pro Pro Pro Cys Pro Arg Cys Pro
        50                  55                  60

<210> SEQ ID NO 101
<211> LENGTH: 3
<212> TYPE: PRT
<213> ORGANISM: Artificial Sequence
<220> FEATURE:
<223> OTHER INFORMATION: Linker sequence

<400> SEQUENCE: 101

Ala Ala Ala
1
```